United States Patent [19]
Ohno et al.

[11] Patent Number: 5,853,998
[45] Date of Patent: Dec. 29, 1998

[54] PROBE FOR DIAGNOSING *ENTEROCOCCUS FAECALIS*

[75] Inventors: Tsuneya Ohno, 15-16, Kita-Aoyama 3 chome, Minato-ku, Tokyo 107, Japan; Akio Matsuhisa, Nara, Japan; Hirotsugu Uehara, Kobe, Japan; Soji Eda, Osaka, Japan

[73] Assignees: Tsuneya Ohno, Tokyo; Fuso Pharmaceutical Industries, Ltd., Osaka, both of Japan

[21] Appl. No.: 920,828

[22] Filed: Aug. 29, 1997

Related U.S. Application Data

[62] Division of Ser. No. 362,577, filed as PCT/JP93/00936 Jul. 7, 1993.

[30] Foreign Application Priority Data

Jul. 7, 1992 [JP] Japan .................................. 4-179719

[51] Int. Cl.$^6$ .............................. C12Q 1/68; C07H 21/04
[52] U.S. Cl. ............................ 435/6; 536/23.1; 536/23.7; 536/24.32; 935/8; 935/9; 935/78
[58] Field of Search ............................. 435/6; 536/24.32, 536/23.1, 23.7; 935/78, 8, 9

[56] References Cited

PUBLICATIONS

Alberts et al., *Molecular Biology of the Cell*, Second Edition, Garland Publishing Inc., New York, NY, pp. 182 and 188–193 (1989).
Bell, et al., "The Nucleotide Sequences of the rbsD, rbsA, and rbsC Genes of *Escherichia coli* K12", *The Journal of Biological Chemistry* 261(17):7652–7658 (Jun. 1986).
Betzl, et al., "Identification of Lactococci and Enterococci by Colony Hybridization with 23S rRNA–Targeted Oligonucleotide Probes", *Applied and Environmental Microbiology*: 56(9):2927–2929 (Sep. 1990).
Buckel, et al., "An Analysis of the Structure of the Product of the rbsA Gene of *Escherichia coli* D12", *The Journal of Biological Chemistry* 261(17): 7659–7662 (Jun. 1986).
Cano et al., *Microbiology*, West Publishing Company, Minneapolis, MN, pp. 264–268, 279, 293, 296, 297, and 801 (1986).
Davis, et al., "Direct Identification of Bacterial Isolates in Blood Cultures by Using a DNA Probe", *Journal of Clinical Microbiology* 29(10):2193–2196 (Oct. 1991).
De Buyser, et al., "Evaluation of a ribosomal RNA gene probe for the identification of species and subspecies within the genus Staphylococcus", *Journal of General Microbiology* 138:889–899 (1992).
Gerberding et al. Antimicrobial Agents and Chemotherapy 35(12):2574–2579 (1991).
Groarke, et al., "The Amino Acid Sequence of D–Ribose––binding Protein from *Escherichia coli* K12", *The Journal of Biological Chemistry* 258(21):12952–12956 (Jun. 1983).
Hall, et al., "Typing of Enterococcus Species by DNA Restriction Fragment Analysis", *Journal of Clinical Microbiology* 30(4):915–919, (Apr. 1992).
Hope, et al., "Ribokinase from *Escherichia coli* K12", *The Journal of Biological Chemistry* 261(17):7663–7668 (Jun. 1986).
Joffee, et al., "Epidemiologic Studies of Nosocomial Infections with *Pseudomonas aeruginosa* Using a DNA Probe", *Abstracts of the Annual Meeting*:485 (1989).
Lehninger, A.L., *Principles of Biochemistry*, Worth Publishers, Inc., New York, pp. 809–811 (1982).

(List continued on next page.)

*Primary Examiner*—Carla J. Myers
*Attorney, Agent, or Firm*—Marshall, O'Toole, Gerstein, Murray & Borun

[57] ABSTRACT

DNA probes for diagnosing infectious diseases involving *Enterococcus faecalis* and methods of using such probes are provided.

2 Claims, 6 Drawing Sheets

OTHER PUBLICATIONS

Maniatis et al., *Molecular Cloning: A Laboratory Manual*, Cold Spring Harbor Laboratory, Cold Spring Harbor, NY, pp. 309–330, 374 and 375 (1982).

Sambrook et al., *Molecular Cloning: A Laboratory Manual*, Second Edition, Cold Spring Harbor Laboratory Press, Cold Spring Harbor, NY, pp. 5.10, 5.11, and 12.21–12.23 (1989).

Smith eet al., *Principles of Biochemistry: General Aspects*, Seventh Edition, McGraw–Hill Book Company, New York, NY, p. 723 (1983).

Tredget, et al., "Epidemiology of Infections with *Pseudomonas aeruginose* in Burn Patients: The Role of Hydrotherapy", *Clinical Infectious Diseases* 15:941–949, (1992).

Watson et al., *Molecular Biology of the Gene*, Fourth Edition, The Benjamin/Cummings Publishing Company, Inc., Menlo Park, CA, pp. 89, 208–210, and 608 (1987).

Watson et al., *Recombinant DNA: A Short Course*, Scientific American Books, USA, pp. 58–60 (1983).

Weems et al., Journal of Antimicrobial Chemotherapy 1989 24:121–130.

PROBE FOR DIAGNOSING *ENTEROCOCCUS FAECALIS*

This is a Divisional of U.S. application Ser. No. 08/362,577, filed Mar. 27, 1995

[TECHNICAL FIELD]

The present invention relates to probes, prepared by making use of causative bacteria of infectious diseases, which are useful for detecting and identifying the causative bacteria.

[BACKGROUND ART]

In pathology, infection is defined as invasion and establishment of a foothold for growth in an organism by a pathogenic organism (hereinafter referred to as "bacteria"), then the outbreak of disease depends upon the interrelationship between the resistance of host and the virulence of bacteria.

In the infectious diseases, improvement in treatment methods of bateremia have been raised as an important issue. That is to say, bacteremia is not a disease caused by a particular bacterium, but is caused by emergence and habitancy of the various bacteria in blood, then onset thereof is clinically suspected when fever of about 40° C. persists for two or more days. If a patient is an infant or is suffering from terminal cancer with weakened resistance, the patient may die in one or two days, therefore, the bacteremia is a serious and urgent disease, and the improvement in treatment methods thereof have been awaited.

In the infectious disease, phagocytes including neutrophils, monocytes and macrophages primarily work in defense of the body. Emergence of bacteria in the blood is thought as invasion of predominant bacteria which have emerged from the tissue of the phagocyte.

Bacteremia is a state wherein the bacteria is emerged into the blood, and a large amount of antibiotic is administrated to treat it wherein the causative bacteria is sensitive to the antibiotic. Generally, since antibiotics lower the functions of the internal organs such as liver, it is necessary to pay an attention to reduce an administration of an ineffective antibiotic to a patient in a serious state.

When bacteremia is defined as a case wherein phagocytesis of cells can not overcome the virulence of bacteria, then the bacteria spread in the body through the blood, bacteremia with serious symptoms due to toxins produced by the bacteria is called as sepsis. Proof of sepsis, in the other word, establishment of the diagnosis requires a check on the items of 1) clinical symptoms, 2) culturing of specimen, 3) gram-staining of the bacteria contained in the specimen, and 4) shock state, then, upon completing the check of these items, the treatment method is determined. Accordingly, to quickly and reliably identify the bacteria have been awaited in the art.

In the present method for detecting and identifying bacteria in a bacteremia-specimen, it is a common procedure to identify in selective medium a specimen which have positive signal in a routine process of culture bottle. However, to successfuly culture the bacteria from these blood specimen is quite difficult, then, if a large dose of antibiotics is administrated when bacteremia was suspected, bacteria in the blood will not be cultured and grown in many cases, therefore, the rate of culture bottle positive case become extremely low.

Although available sub-routine methods include instrumental analysis of constituents and metabolic products of bacteria (Yoshimi Benno, "Quick identification of bacteria with gas chromatography", Rinsho Kensa, Vol. 29, No.12, Nov. 1985, Igaku Shoin ed.), a method utilizing specific antibody (Japanese Patent Provisional Publication No. 60-224068), and a hybridization method utilizing specificity of DNA (Japanese Phase Patent Provisional Publication No. 61-502376) have been developed, any of which are required to separate the bacteria and culture it. On the other hand, as a method established based on the function of phagocytes in infectious diseases, there is a method to examine, under an optical microscope, a stained smear of buffy coat wherein leukocyte of the blood sample is concentrated. Generally speaking, although the rate of detection of bacteria in buffy coat specimens from adult bacteremia patients is 30% at most, which is similar to that in earlobe blood specimens, it was reported that bacteria had been detected in seven cases of ten cases (70%) in newborn patients, therefore, an information concerning the presence of a bacteria in peripheral blood to be obtained by microscope examination on smear is an important for treatment.

Since the conventional methods necessiate the pretreatment which requires at least three to four days in total containing one to two day(s) for selective isolation of bacteria from a specimen, one day for cultivation, and one or more day(s) for fixation, and the culture thereof is continued in practice until the bacteria grow, the culture will needs one week or more even for C.B.-positive cases, therefore, this was a factor in high mortality of C.B.-positive patients being treated by the conventional methods. For example, according to the a report published in "The Journal of the Japanese Association for Infectious Diseases", Vol.58, No.2, p.122, 1984, even though the blood culture positive rate was 28.6% (163 cases/569 cases), the mortality was as high as 84.6% (138 cases/163 cases). Further, it may be impossible to distinguish contamination at the cultivation by indigenous bacteria. For example, *Staphylococcus epidermides*, which is one of Staphylococci and is the causative bacterium of bacteremia, stayed in the skin of the normal person, then, there is a risk on contamination of a specimen with this bacterium when a needle is inserted into the skin.

As an important matter, under such circumstances above, since many bacteria in a specimen to be cultured have been incorporated into said phagocyte and are dead or stationary immobilized, the number of growable bacteria is small even under appropriate conditions for cultivation, thereby, the actual detection rate of bacteria through culture specimen is as low as about 10%. In the other word, at this moment, 90% of the examined blood, which have been cultured for further one or more day(s), of the patient suspected clinically as suffering with bacteremia can not clarify the presence of bacteria.

In light of the situation above, the present practice depends on a treatment to be started when bacteremia is clinically suspected without awaiting the detection results, that is to say, a trial and error method wherein an antibiotic having broad spectrum is administrated first, and if the antibiotic is not effective after one or two day(s), another antibiotic will be tried.

According to the method to stain the bacteria in the specimen, the constituents of the living body are also stained together with bacteria, therefore, experience to quickly identify bacteria according to thier image through microscope is required, then there may be cases that can be hardly diagnosed as bacteremia.

Although bacteremia is a disease wherein a rapid and exact diagnosis have been required, the conventional diagnosis method can not respond to such requirements.

[DISCLOSURE OF INVENTION]

The present invention was established in view of the problems in the art, and is directed to a probe having a specific reactivity with DNA or RNA obtained from primary causative bacteria of the infectious diseases, then provide a genetic information by analyzing the base sequence of DNA in the probe.

By the probe of the present invention, for example, a causative bacteria of the infectious diseases is detected rapidly and exactly, without cultivating/proliferating the bacteria, through a detection of DNA held in the causative bacteria digested and incorporated gradually with the phagocyte. Then, if primers are designed by referring to an information on base sequence of these probes, causative bacteria can identify, without the hybridization, by amplifying the DNA with PCR technique.

When non-radioactive probe, for example, biotinylated probe is used for hybridization, since such probe can be detected with an optical microscope in a conventional laboratory without radio isotope handling facilities, the detection process would be rapid and simple.

[BEST MODE FOR CARRYING OUT THE INVENTION]

Figure 1:
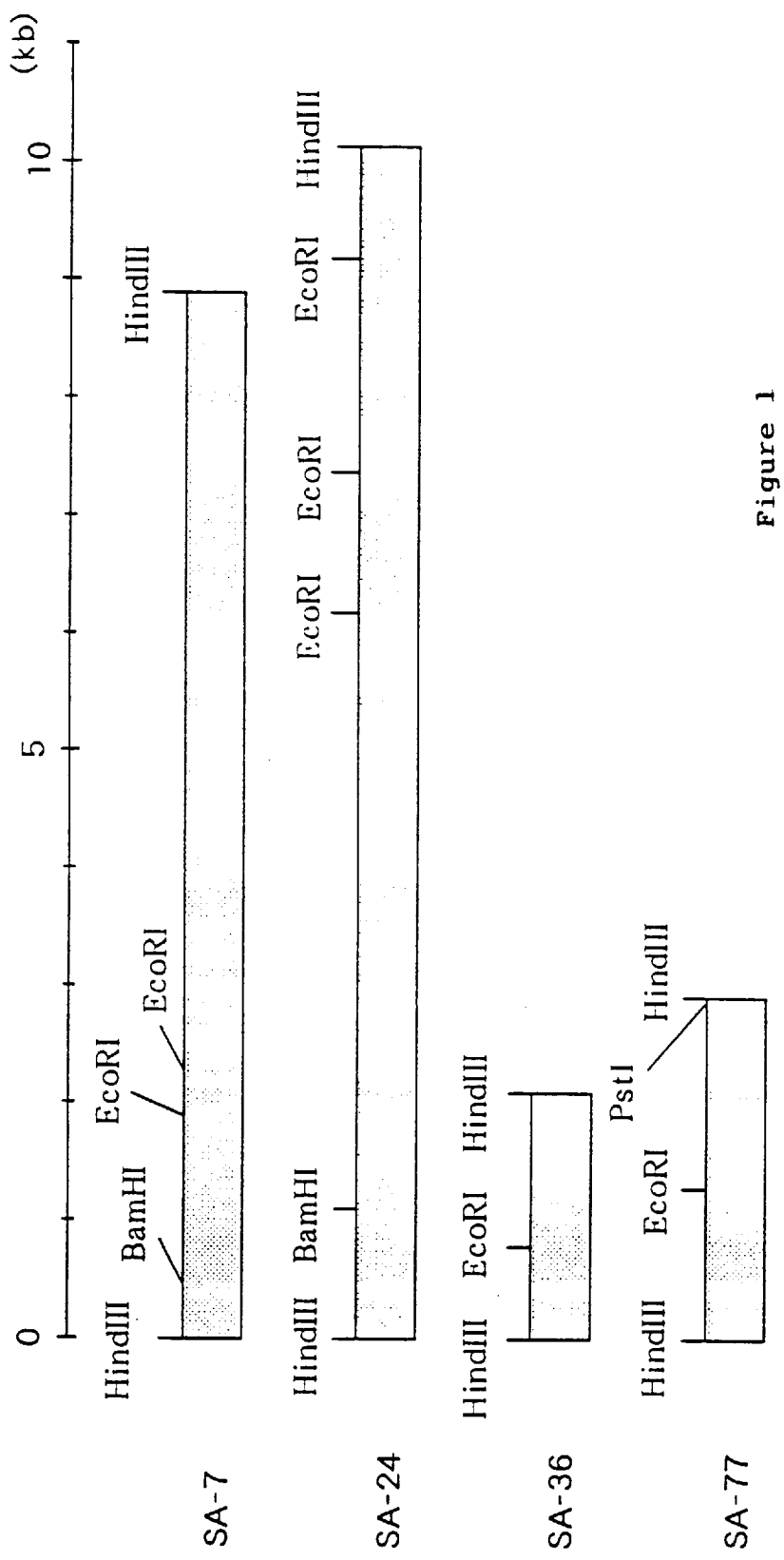
FIG. 1 is a restriction enzyme map of HindIII fragment on probe for detecting *Staphylococcus aureus*.

Examples on probes prepared from *Staphylococcus aureus, Staphylococcus epidermidis, Enterococcus faecalis, Pseudomonas aeruginosa, Escherichia coli, Klebsiella pneumoniae* and *Enterobacter cloacae* (J. Infection, vol. 26, pp.159–170 (1993), J. Clin. Microbiol., vol.31., pp.552–557 (1993)), respectively listed as relatively popular causative bacteria of the infectious diseases, especially bacteremia were described as follows.

Example 1
Preparation of DNA Probe from Causative Bacteria of Infectious Diseases (1) isolation of Causative Bacteria of Infectious Diseases Blood collected from the patient who have been suffered with targeted diseases were applied to Blood Culture Method (BBC System: Blood Culture System; Roche) and to a conventional identification kit (Api 20, Apistaf, Apistlep 20: Bio-Meryu), and the each causative bacterium was isolated and identified according to the manual of said kit.

(2) Extraction and Purification of Genomic DNA from Isolated Strain

Strains isolated in the above (1) was cultivated overnight in BHI (Brain Heart Infusion) medium, collected the cultivated bacteria, added thereto achromopeptidase in stead of lysozvme, then, Genomic DNA was extracted according to Saito-Miura Method ("Preparation of Transforming Deoxyribonucleic Acid by Phenol Treatment", Biochem. Biophys. Acta. vol. 72, pp.619–629), and extracted DNA was digested with restriction enzyme HindIII and was random cloned into vector pBR322.

(3) Selection of Probe having Specificity to Species of Origin Bacteria

*Escherichia coli* containing each clone prepared according to Manual of Maniatis (T. Maniatis, et al., "Molecular Cloning (A Laboratory Manual)", Cold Spring Harbour Laboratory (1982)) was cultivated with small scale culture, and obtained plasmids containing each clone.

These plasmids were digested with restriction enzyme HindIII, thereby inserts were separated completely from plasmids with 1% agarose-gel electrophoresis (Myupid: Cosmo-Bio), then, were transcribed to nylon membrane with Southern-Transfer Technique (Paul Biodine A: Paul), and were cross-hybridized with a probe prepared by labelling $^{32}$P-dCTP (Amersham) through nick-translation to chromosome DNA from each bacteria species aforelisted.

In this hybridization, a probe which did not cross-react with any insert except for a probe prepared from the origin species thereof was selected as a probe containing DNA fragment which is specific to causative bacteria of the infectious diseases.

With regard to probes prepared from *Escherichia coli, Klebsiella pneumoniae, Enterobacter cloacae*, since these bacteria are belonged to the same group (enteric bacteria; Gram negative aerobic bacillus) as a causative bacteria of bacteremia (See, J. Infection, vol. 26, pp.159–170 (1993), J. Clin. Microbiol., vol.31., pp. 552–557 (1993), supra), and the cross-reaction had been confirmed among said three bacteria in the foregoing series experiments on the specificity, each probe prepared from one of said three bacteria was designated as a probe for detecting all these bacteria as a relevant bacteria.

Probes (denotation) selected from each species through the foregoing methods are listed in the following Table 1.

TABLE 1

| SPECIES | DENOTATION |
|---|---|
| Staphylococcus aureus | SA-7, SA-24, SA-36, SA-77 |
| Staphylococcus epidermidis | SE-3, SE-22, SE-32, SE-37 |
| Enterococcus faecalis | S2-1, S2-3, S2-7, S2-27 |
| Pseudomonas aeruginosa | P2-2, P2-7, P2-17, P4-5 |
| Escherichia coli | EC-24, EC-34, EC-39, EC-625 |
| Klebsiella pneumoniae | KI-50 |
| Enterobacter cloacae | ET-12, ET-49 |

Figure 2:
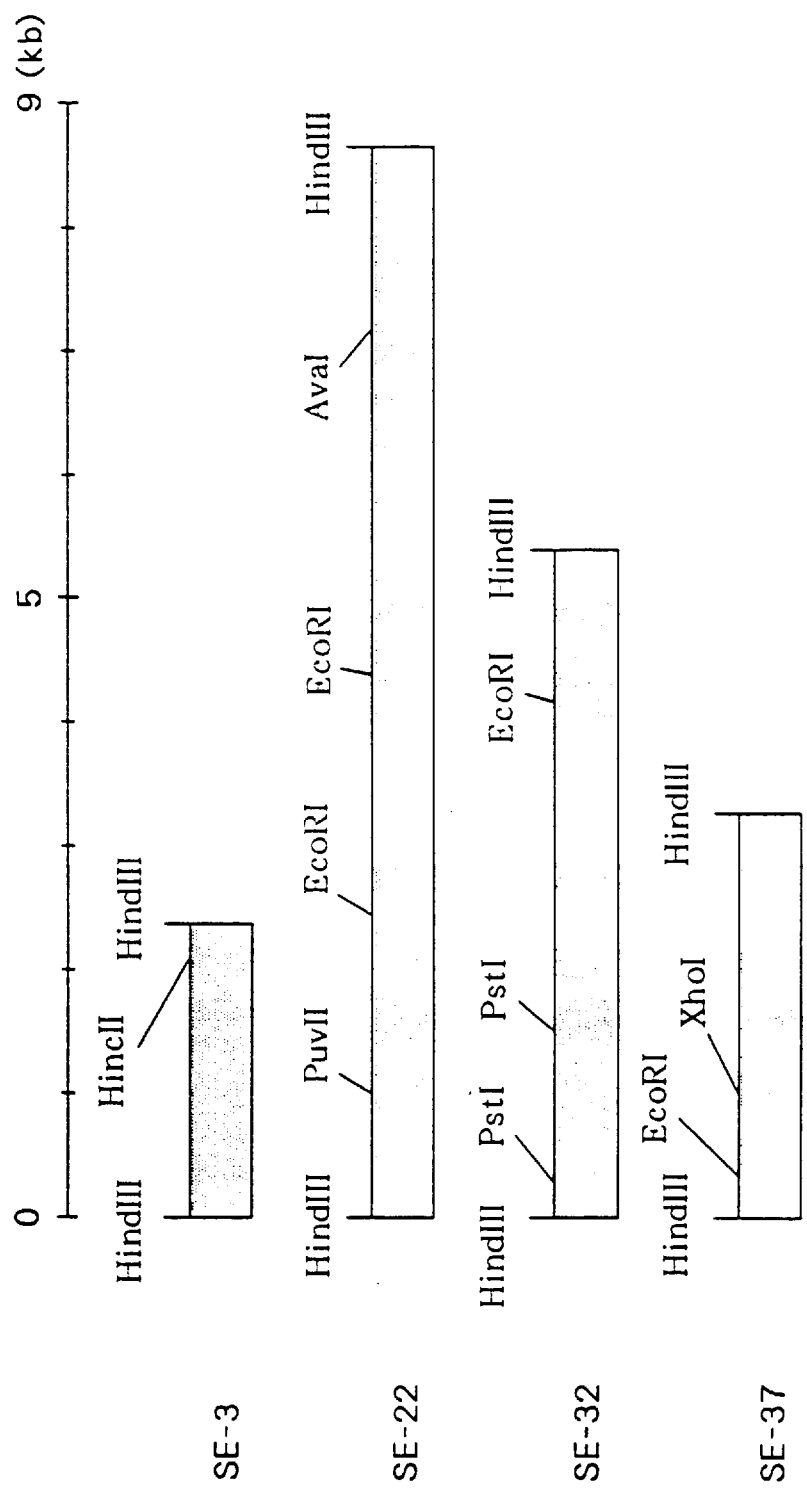
FIG. 2 is a restriction enzyme map of HindIII fragment on probe for detecting *Staphylococcus epidermidis*.
Figure 3:
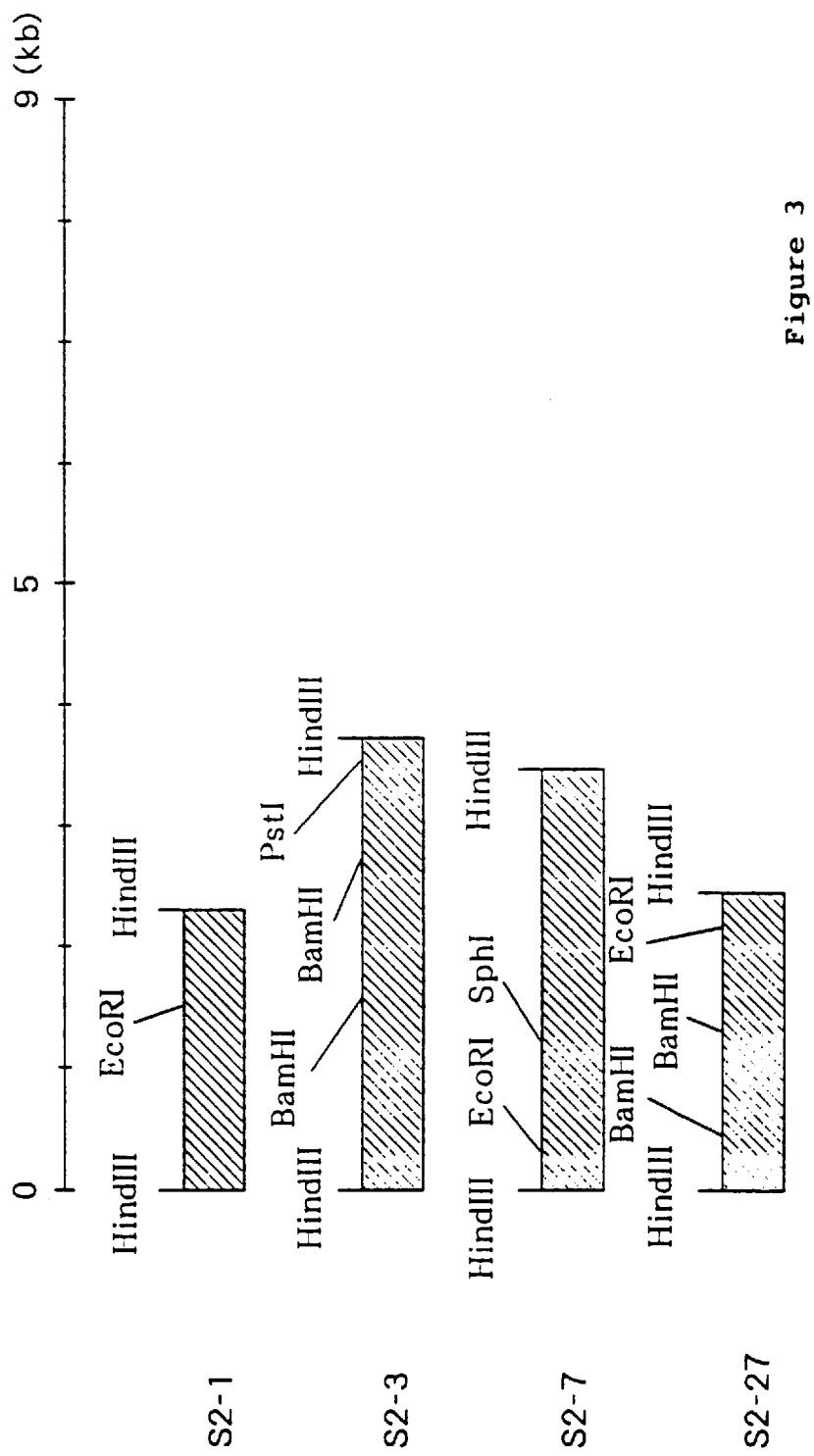
FIG. 3 is a restriction enzyme map of HindIII fragment on probe for detecting *Enterococcus faecalis*.
Figure 4:
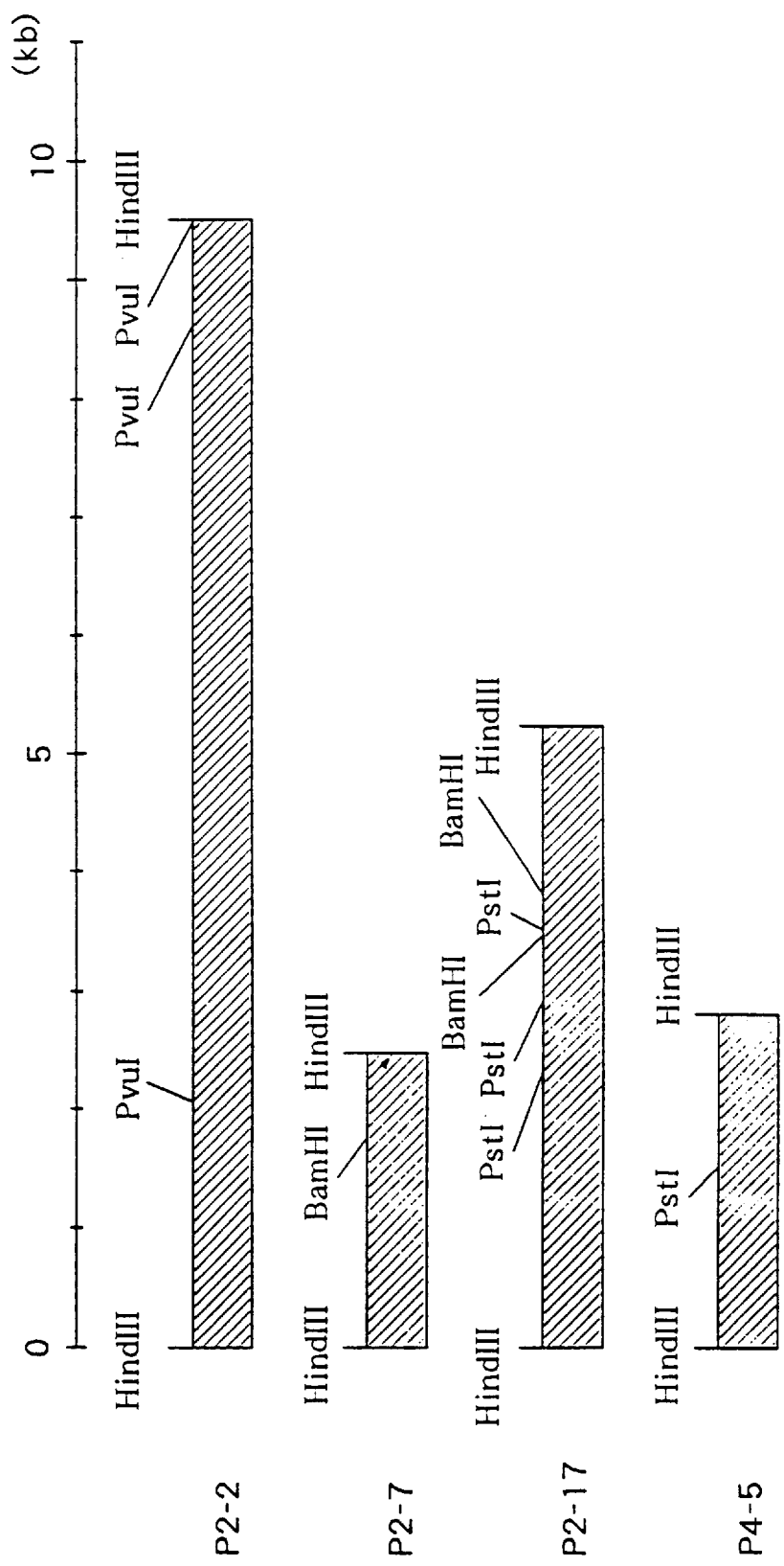
FIG. 4 is a restriction enzyme map of HindIII fragment on probe for detecting *Pseudomonas aeruginosa*.
Figure 5:
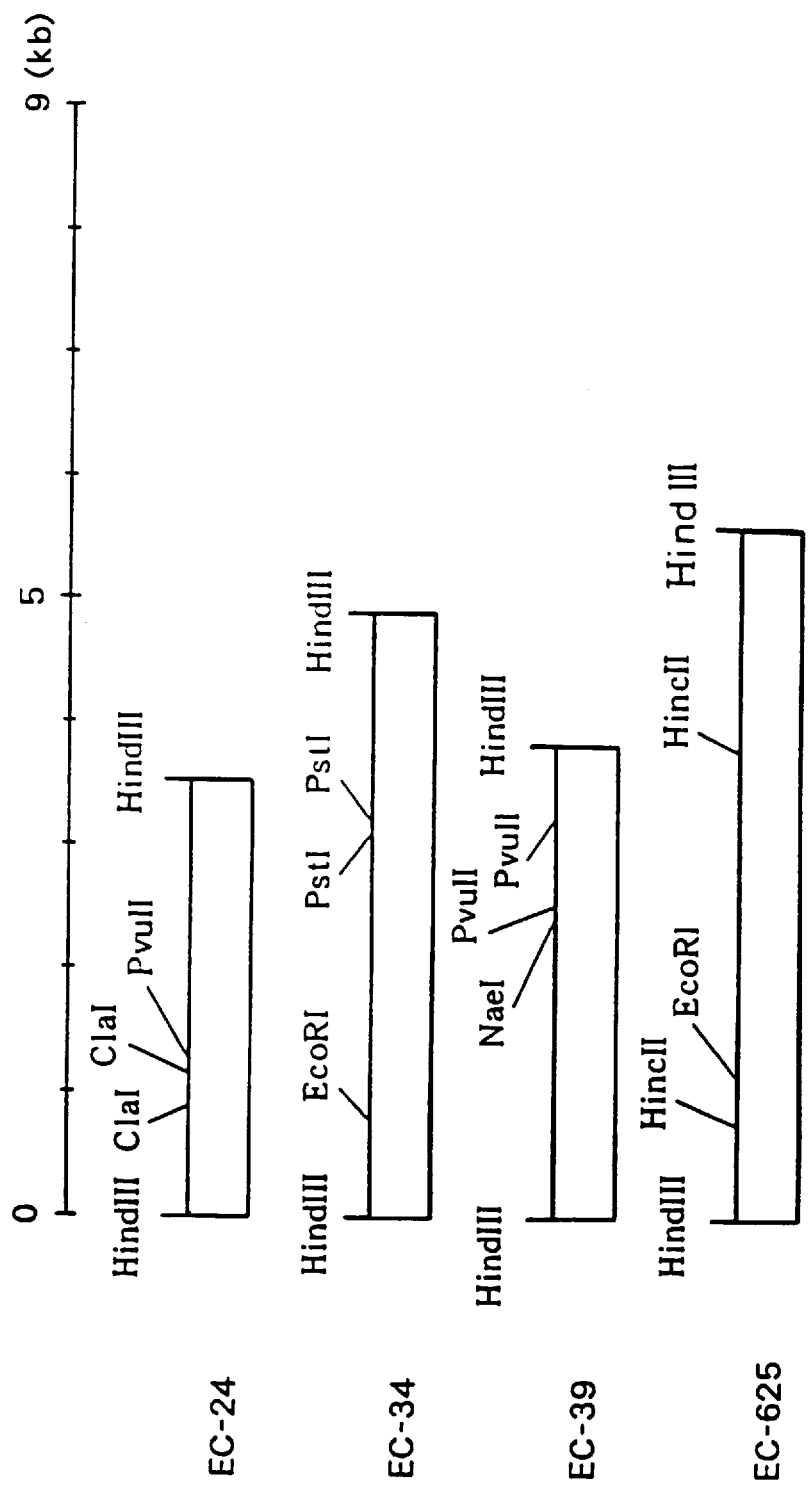
FIG. 5 is a restriction enzyme map of HindIII fragment on probe for detecting *Escherichia coli*.
Figure 6:
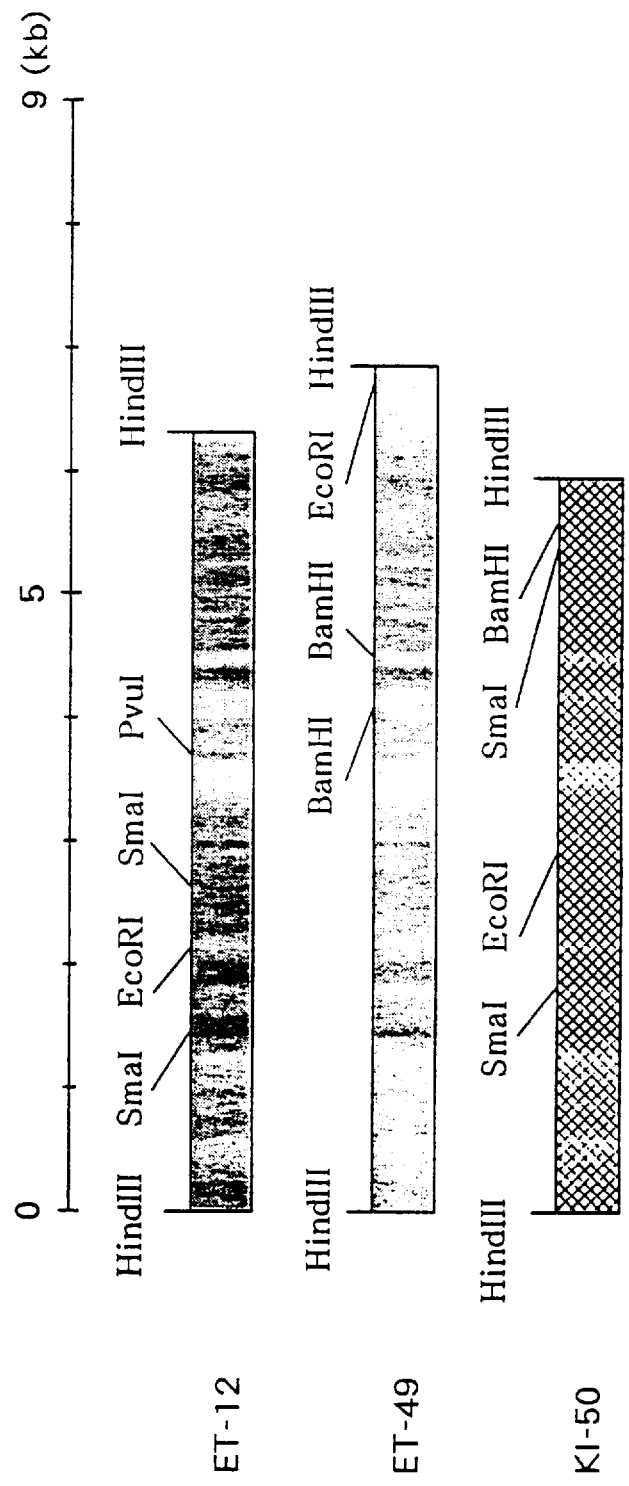
FIG. 6 is a restriction enzyme map of HindIII fragment on probe for detecting *Enterobacter cloacae* and *Klebsiella pneumonia*.

Restriction enzyme maps of each probe were also illustrated in FIGS. 1–6 respectively.

Example 2
Evaluation on Species-Specificity of Each DNA Probe

Reactivity between each probe and DNA from causative bacteria of infectious diseases were examined acooding to the following method.

First of all, as subject strains for an examination, clinical isolates of *Staphylococcus aureus, Staphylococcus epidermidis, Enterococcus faecalis, Pseudomonas aeruginosa, Escherichia coli, Klebsiella pneumoniae,* and *Enterobacter cloacae* were isolated according to the method of Example 1 (1) above.

Then, DNA of each clinical isolate were extracted according to the method of Example 1 (2), and samples for dot-blot-hybridization were obtained by spotting certain amount (e.g., 5 $\mu$l) of DNA to nylon filter and selecting the isolates denatured with alkaline. Hybridization on DNA probes prepared from each subjected bacterium and labelled with biotin (Bio-dUTP; BRL) were performed overnignt according to Manual of Maniatis, supra, under the condition of 45% formamide, 5×SSC, 42 ° C.

Samples obtained through overnight hybridization were washed twice with 0.1×SSC, 0.1% SDS for 20 minutes at 55° C., then, were detected the color reaction with Streptavidin-ALP conjugates (BRL), and evaluated the hybridization.

Experimental results on reactivity between each probe and DNA of each clinical isolate are illustrated in the following table 2 (i)–(vi). With regard to a denotation in the tables, denotation of "+" refers to the presence of a signal on hybridization, while that of "−" refers to the absence of a signal on hybridization.

TABLE 2 (i)

|  | SA-7 | SA-24 | SA-36 | SA-77 |
|---|---|---|---|---|
| Staphylococcus aureus | + | + | + | + |
| Staphylococcus epidermidis | − | − | − | − |
| Enterococcus faecalis | − | − | − | − |
| Pseudomonas aeruginosa | − | − | − | − |
| Escherichia coli | − | − | − | − |
| Klebsiella pneumoniae | − | − | − | − |
| Enterobacter cloacae | − | − | − | − |

TABLE 2 (ii)

|  | SE-3 | SE-22 | SE-32 | SE-37 |
|---|---|---|---|---|
| Staphylococcus aureus | − | − | − | − |
| Staphylococcus epidermidis | + | + | + | + |
| Enterococcus faecalis | − | − | − | − |
| Pseudomonas aeruginosa | − | − | − | − |
| Escherichia coli | − | − | − | − |
| Klebsiella pneumoniae | − | − | − | − |
| Enterobacter cloacae | − | − | − | − |

TABLE 2 (iii)

|  | S2-1 | S2-3 | S2-7 | S2-27 |
|---|---|---|---|---|
| Staphylococcus aureus | − | − | − | − |
| Staphylococcus epidermidis | − | − | − | − |
| Enterococcus faecalis | + | + | + | + |
| Pseudomonas aeruginosa | − | − | − | − |
| Escherichia coli | − | − | − | − |
| Klebsiella pneumoniae | − | − | − | − |
| Enterobacter cloacae | − | − | − | − |

TABLE 2 (iv)

|  | P2-2 | P2-7 | P2-17 | P4-5 |
|---|---|---|---|---|
| Staphylococcus aureus | − | − | − | − |
| Staphylococcus epidermidis | − | − | − | − |
| Enterococcus faecalis | − | − | − | − |
| Pseudomonas aeruginosa | + | + | + | + |
| Escherichia coli | − | − | − | − |
| Klebsiella pneumoniae | − | − | − | − |
| Enterobacter cloacae | − | − | − | − |

TABLE 2 (v)

|  | EC-24 | EC-34 | EC-39 | EC-625 |
|---|---|---|---|---|
| Staphylococcus aureus | − | − | − | − |
| Staphylococcus epidermidis | − | − | − | − |
| Enterococcus faecalis | − | − | − | − |
| Pseudomonas aeruginosa | − | − | − | − |
| Escherichia coli | + | + | + | + |
| Klebsiella pneumoniae | + | + | + | + |
| Enterobacter cloacae | + | + | + | + |

TABLE 2 (vi)

|  | ET-12 | ET-49 | KI-50 |
|---|---|---|---|
| Staphylococcus aureus | − | − | − |
| Staphylococcus epidermidis | − | − | − |
| Enterococcus faecalis | − | − | − |
| Pseudomonas aeruginosa | − | − | − |
| Escherichia coli | + | + | + |
| Klebsiella pneumoniae | + | + | + |
| Enterobacter cloacae | + | + | + |

Apparently from Table 2 above, each probe have reacted only with DNA obtained from origin strain (or relative strain thereof) and not reacted (hybridized) with any DNA obtained from strains except for strains from the origin strain, therefore, their specificity have been confirmed.

Example 3

Analysis of Base Sequence

Base sequence of DNA probes (total 23 probes) of the present invention, which have been confirmed their specificity to the origin species in the Examples 1 and 2, were sequenced according to the following method.

(1) Preparation of Plasmid DNA

*Escherichia coli* K-12, JM109 transformants, wherein the subcloned insert fragments (to be seqeuenced) is contained in pGem-3Z (Promega), was inoculated in 5ml of Luria-Bactani Medium (bacto-tryptone, 10 g/1 L: bacto-yeast extract, 5 g/1 L; NaCl, 10 g/1 L; adjusted pH to 7.0 with 5 N NaOH) and cultivated overnight.

Culture liquid was centrifuged (5,000 rpm, 5 min.) and collected the bacteria. 100 µl of solution of 50 mM glucose/50 mM Tris-HCI (pH8.0)/10 mM EDTA containing 2.5mg/ml of lysozyme (Sigma) was added to precipitate, and left at room temperature for five minutes. 0.2M NaOH solution containing 1% of sodium dodecyl sulfate (Sigma) was added to the suspension so obtained and mixed therewith. 150 µl of 5M pottasium acetate solution (pH 4.8) was further added thereto and mixed therewith, then iced for 15 minutes.

Supernatant obtained by centrifugation (15,000 rpm, 15 min.) was treated with phenol/CHCl$_3$ and added thereto ethanol of two times volume, then precipitate was obtained by centrifugation (12,000 rpm, 5 min.). This precipitate was dissolved in 100 µl of solution of 10 mM Tris-HCI (pH 7.5)/0.1 mM EDTA and added thereto 10 mg/ml RNaseA (Sigma) solution, then left it at room temperature for 15 minutes.

300 µl of 0.1M sodium acetate solution (pH 4.8) was added to this preparation and treated with phenol/CHCl$_3$, then precipitate was obtained by adding ethanol to supernatant. DNA samples were prepared by drying this precipitate and dissolving in 10 µl distilled water.

(2) Pretreatment for Sequencing

Pretreatment for sequencing was performed with Auto-Read™ Sequencing Kit (Pharmasia).

Concentration of DNA to become a template was adjusted to 5–10 µg in 32 µl. 32 µl of template DNA was transferred to 1.5 ml mini-tube (Eppendolf), and added thereto 8 μl of 2M NaOH solution, then mixed gently therewith. After instant centrifugation, it was left at room temperature for 10 minutes.

7 μl of 3M sodium acetate (pH 4.8) and 4 μl of distilled water, then 120 μl of ethanol were added thereto then mixed therewith, and left for 15 minutes on dry ice. DNA which have been precipitated by centrifugation for 15 minutes were collected, and supernatant was removed carefully. The precipitate so obtained were washed with 70% ethanol and centrifuged for 10 minutes. Then, the supernatant was removed carefully again and dried the precipitate under the reduced pressure.

The precipitate was dissolved in 10 μl of distilled water, then 2 μl of fluorescent primer (0.42 $A_{260}$ unit/10 ml, 4–6pmol) [M13 Universal Primer; 5'-Fluorescein-d [CGACGTTGTAAAACGACGGCCAGT]-3'(SEQ. ID. NO:24)(1.6 pmol/μL; 0.42 $A_{260}$ unit/ml); M13 Reverse Primer, 5'-Fluorescein-d[CAGGAAACAG CTATGAC]-3' (SEQ. ID. NO:25)(2.1 pmol/μl; 0.42 $A_{260}$ unit/ml)] and 2 μl of saline for annealing were added thereto, and mixed gently.

After instant centrifugation, they were heat-treated at 65° C. for 5 minutes and rapidly transferred it to a circumstance of 37° C. and kept the temperature for 10 minutes. After keeping the temperature, it was left at room temperature for 10 minutes or more and centrifugated instantly. Then, samples were prepared by adding thereto 1 μl of an elongation saline and 3 μl of dimethyl sulfoxide.

Four mini-tubes have been identified with one of marks of "A", "C", "G" and "T", and, according to the mark, 2.5 μl of A Mix (dissolved ddATP with dATP, dCTP, $c^7$dGTP and dTTP), C Mix (dissolved ddCTP with dATP, dCTP, $c^7$dGTP and dTTP), G Mix (dissolved ddGTP with dATP, dCTP, $c^7$dGTP and dTTP), or T Mix (dissolved ddTTP with dATP, dCTP, $c^7$dGTP and dTTP) were poured into each identified tube. Each solution was preserved in freezed condition, and the solution was heated at 37 ° C. for one minute or more to use it.

2 μl of diluted T7DNA polymerase (Pharmacia; 6–8units/2 μl ) was added to DNA sample, and completely mixed by pipetting or mixing it gently. Immediately after completing the mixing, these mixed solution was poured into 4.5 μl of four-types solution respectively which have kept the certain temperature. Fresh tips were used at the time of pouring.

The solution have been kept for five minutes at 37° C., then 5 μl of termination solution were poured into each reaction-solution. Fresh tips were used for pouring. Immediately after keeping the solution for 2–3 minutes at 90° C., it was cooled on ice. 4–6 μl/lane of the solution was applied to the electrophoresis.

(3) Sequencing on Base Sequence

Sequencing on each base sequence of probes, disclosed in Examples 1 and 2, having the specificity against *Staphylococcus aureus* or *Staphylococcus epidermidis* were performed with A. L. F. DNA Sequencer System (Pharmacia) under an electrophoresis condition of 45° C. for 6 hours. Then, base sequences of the probes (SEQ ID.No.) prepared from each causative bacteria of the infectious diseases and listed in the following table 3 were disclosed in the sequence listing attached hereto.

TABLE 3

| SPECIES | Probes (SEQ ID. No.) | |
|---|---|---|
| *Staphylococcus aureus* | SA-7 (1), | SA-24 (2) |
| | SA-36 (3), | SA-77 (4) |
| *Staphylococcus epidermidis* | SE-3 (5), | SE-22 (6) |
| | SE-32 (7), | SE-37 (8) |
| *Enterococcus faecalis* | S2-1 (9), | S2-3 (10) |
| | S2-7 (11), | S2-27 (12) |
| *Pseudomonas aeruginosa* | P2-2 (13), | S2-7 (14) |
| | P2-17 (15), | P4-5 (16) |
| *Escherichia coli* | EC-24 (17), | EC-34 (18), |
| | EC-39 (19), | EC-625 (20) |
| *Klebsiella pneumoniae* | KI-50 (23) | |
| *Enterobacter cloacae* | ET-12 (21), | ET-49 (22) |

Thereby, genetic information concerning the specific site of each causative bacteria of the infectious diseases (or relative bacteria thereof) have been clarified.

According to probes of the present invention, for example, causative bacteria of the infectious diseases which have incorporated into the phagocyte can be directly detected, and rapidly and exactly identified without proliferating the bacteria. That is to say, according to the diagnosis using the probe of the present invention, identification of the bacteria can be realized with single specimen, then, reduced the necessary time for diagnosis to about one to two day(s), while the conventional method (with low detection rate) required 3–4 days, and improved remarkably the detection rate. Therefore, this invention can provide an objective factors for the treatment of bacteremia, then realize the effective treatment in the early stage of the infectious diseases, and expect to reduce the mortality.

Then, by clarifying the base sequences of probes which specifically react with primary bacteria of the infectious diseases, these probes can be prepared artifically. Further, a part of information on the analyzed base sequences may be used for rapidly diagnosing the causative bacteria by amplifying DNA of causative bacteria of the infectious diseases in the clinical specimen with PCR technique and primers prepared by making use of said information.

Further, by comparing base sequences of Genomic DNA in the clinical specimen with that of the present invention, rapid identification of the species of the causative bacteria of infectious diseases can be realized.

As stated above, the present invention provide desirable probes for diagnosing the infectious diseases, then expect utilities as a factor to prepare primers for PCR and standard sequence for a comparison with Genomic DNA in the clinical specimen, and further expect an effect to provide valuable hints for preparing and developing the other probes which specifically react with causative bacteria of the infectious diseases.

Then, since the base sequences disclosed in the present application was obtained by random-cloning the Genomic DNA of clinical isolates, utilities of the base sequences of the present invention should be extended to the complementary strands thereof.

Further, although it may be thought that DNA obtained from the wild strains contain the mutated portion, apparently from the disclosure of the Examples above, said mutated DNA portion would not affects the utilities to be derived by the present invention comprising the specificity of the probes of the present invention in the hybridization for a diagnosis of the infectious diseases, and an usage of the information on the base sequences disclosed in the present application to design the primers for PCR technique to realize a rapid diagnosis of the infectious diseases.

We claim:

1. A probe composition for detecting *Enterococcus faecalis* wherein the probe composition consists essentially of
(a) the DNA of any one of SEQ ID NOS:9 through 12, or
(b) the complement of (a).

2. A method for detecting the presence of *Enterococcus faecalis* in a sample comprising the steps of contacting nucleic acid from said sample with the probe composition of claim 1 and detecting hybridization of the nucleic acid from said sample with DNA in said probe composition as an indication of the presence of *Enterococcus faecalis*.

\* \* \* \* \*

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 8959 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Staphylococcus aureus
        ( B ) STRAIN: Clinical Isolate SA- 7

( x i ) SEQUENCE DESCRIPTION: SEQ ID NO:1:

```
AAGCTTTATC TGCTGAATAT ACCGCATTTT TTATCTTGTT AATTGTCGGC ACATTTTCTT      60
CAATAGTTAA ACCTGCTTTG TTAGCTTCTT CTAATAATGC TCGAGTTACT GTTTATTAAA     120
TGTTCATTCG CTTTTCAACG ACAACTGACG AACCAGTATC TGTTAGCTTA GACGCAACAG     180
CGTTAATCTT CTGATTCACC TTAAATTCTA CATCTGCTTT TTGAGGCTGC TTACGTAGTG     240
TCCCGGTAAT TTCATGTGTA AACTTAGATG GGATGTAAAT ACCTGCAAAA TATTTACCCA     300
TTTTTATCTC ATGATCAGCT TTCTCTCTAC TTACAAACTG CCAATCAAAA CTTTTATTTT     360
TCTTGAGTGT ATTAACCATC GTATTACCGA CATTAACTTT TTTCCCTCTG ATTGTGTCGC     420
CTTTATCTTC ATTAACGACT GCGACCTTGA TGTGTCCCGT GTTGCCATAT GGATCCCACA     480
TTGCCCATAA GTTAAACCAA GCGTAGAACG ATGGCAAAAT AGCTAAGCCT GCTAAGATAA     540
TCCACACAGC TGGCGTCTTA GCTACTTCT  TCAGATCCAT TTTAAATAAT TTAAATGCGT     600
TCTTCATTGT CACACTCCTA TGTAGGAATT ATTCATATTT TTTATATATT TTTTGTAAAT     660
TAATTTATTT TTGCGTTGTG AATTAGTATA ATCAATTTAC TGGAAGATAT TTAGTCGATT     720
GATACCTATC AACTATTTTC AGCATACGAT AAATTATAAC AAATCATAGT TTATTATCAC     780
ACTTAATTAT TATATTTTTC AAGGGAGAAT ACGAAATATG CCTAAAAATA AAATTTTAAT     840
TTATTTGCTA TCAACTACCC TCGTATTACC TACTTTAGTT TCACCTACCG CTTATGCTGA     900
TACACCTCAA AAAGATACTA CAGCTAAGAC AACATCTCAT GATTCAAAAA AATCTAATGA     960
CGATGAAACT TCTAAGGATA CTACAAGTAA AGATACTGAT AAAGCAGACA ACAATAATAC    1020
AAGTAACCAA GACAATAACG ACAAAAAATT TAAAACTATA GACGACAGCA CTTCAGACTC    1080
TAACAATATC ATTGATTTTA TTTATAAAGA ATTTACCACA AACCAATATA AACCAATTGC    1140
TAACCAAAAA TAAATACGAT GATAATTACT CATTAACAAC TTTAATCCAA AACTTATTCA    1200
ATTTAAATTC GGATATTTCT GATTACGAAC AACCTCGTAA TGGCGAAAAG TCAACAAATG    1260
ATTCGATAAA AACAGTGACA TAGCATCAAA AATGACACTG ATACGCAATC ATCTAAACAA    1320
GATAAAGCAG ACAATCAAAA AGCACCTAAA TCAAACAATA CAAAACCAAG TACATCTAAT    1380
AAGCAACCAA ATTCGCCAAA GCCAACACAA CCTAATCAAT CAAATAGTCA ACCAGCAAGT    1440
GACGATAAAG CAAATCAAAA ATCTTCATCG AAAGATAATC AATCAATGTC AGATTCGGCT    1500
TTAGACTCTA TTTTGGATCA ATACAGTGAA GATGCAAAGA AAACACAAAA AGATTATGCA    1560
TCTCAATCTA AAAAAGACAA AAATGAAAAA TCTAATACAA GAATCCACA  GTTACCAACA    1620
CAAGATGAAT TGAAACATAA ATCTAAACCT GCTCAATCAT TCAATAACGA TGTTAATCAA    1680
```

| | | | | | | |
|---|---|---|---|---|---|---|
| AAGGATACAC | GTGCAACATC | ATTATTCGAA | ACAGATCCTA | GTATATCTAA | CAATGATGAT | 1740 |
| AGCGGACAAT | TTAACGTTGT | TGACTCAAAA | GATACACGTC | AATTTGTCAA | ATCAATTGCT | 1800 |
| AAAGATGCAC | ATCGCATTGG | TCAAGATAAC | GATATTTATG | CGTCTGTCAT | GATTGCCCAA | 1860 |
| GCAATCTTAG | AATCTGACTC | AGGTCGTAGT | GCTTTAGCTA | AGTCACCAAA | CCATAATTTA | 1920 |
| TTCGGTATCA | AAGGTGCTTT | TGAAGGGAAT | TCTGTTCCTT | TTAACACATT | AGAAGCTGAT | 1980 |
| GGTAATAAAT | TGTATAGTAT | TAATGCTGGA | TTCCGAAAAT | ATCCAAGCAC | GAAAGAATCA | 2040 |
| CTAAAAGATT | ACTCTGACCT | TATTAAAAAT | GGTATTGATG | GCAATCGAAC | AATTTATAAA | 2100 |
| CCAACATGGA | AATCGGAAGC | CGATTCTTAT | AAAGATGCAA | CATCACACTT | ATCTAAAACA | 2160 |
| TATGCTACAG | ATCCAAACTA | TGCTAAGAAA | TTAAACAGTA | TTATTAAACA | CTATCAATTA | 2220 |
| ACTCAGTTTG | ACGATGAACG | CATGCCAGAT | TTAGATAAAT | ATGAACGTTC | TATCAAGGAT | 2280 |
| TATGATGATT | CATCAGATGA | ATTCTGTTCC | TTTTAACACA | TTAGAAGCTG | ATGGTAATAA | 2340 |
| ATTGTATAGT | ATTAATGCTG | GATTCCGAAA | ATATCCAAGC | ACGAAAGAAT | CACTAAAAGA | 2400 |
| TTACTCTGAC | CTTATTAAAA | ATGGTATTGA | TGGCAATCGA | ACAATTTATA | AACCAACATG | 2460 |
| GAAATCGGAA | GCCGATTCTT | ATAAAGATGC | AACATCACAC | TTATCTAAAA | CATATGCTAC | 2520 |
| AGATCCAAAC | TATGCTAAGA | AATTAAACAG | TATTATTAAA | CACTATCAAT | TAACTCAGTT | 2580 |
| TGACGATGAA | CGCATGCCAG | ATTTAGATAA | ATATGAACGT | TCTATCAAGG | ATTATGATGA | 2640 |
| TTCATCAGAT | GAATTCAAAC | CTTTCCGCGA | GGTATCTGAT | AGTATGCCAT | ATCCACATGG | 2700 |
| CCAATGTACT | TGGTACGTAT | ATAACCGTAT | GAAACAATTT | GGTACATCTA | TCTCAGGTGA | 2760 |
| TTTAGGTGAT | GCACATAATT | GGAATAATCG | AGCTCAATAC | CGTGATTATC | AAGTAAGTCA | 2820 |
| TACACCAAAA | CGTCATGCTG | CTGTTGTATT | TGAGGCTGGA | CAATTTGGTG | CAGATCAACA | 2880 |
| TTACGGTCAT | GTAGCATTTG | TTGAAAAAGT | TAACAGTGAT | GGTTCTATCG | TTATTTCAGA | 2940 |
| TCAATGTTAA | AGGATTAGGT | ATCATTTCTC | ATAGAACTAT | CAATGCAGCT | GCCGCTGAAG | 3000 |
| AATTATCATA | TATTACAGGT | AAATAAGTAT | TATTAAACCC | GCAAAATTTA | TAAGTATAAA | 3060 |
| CAAGGAGTTC | GGACTTAAAC | ATATTTCTGT | TCATAAGTCC | GATTTCTTAT | TCAATTAAAC | 3120 |
| CCGAGGTATT | CAGTTCGAAC | GCCTCGGGTC | ATTTTATATA | AATATATTAT | TTTATGTTCA | 3180 |
| AATGTTCCTC | ATCATATCCG | TTTCAATTGT | CATCTCACAC | ATTTTATAAA | TATGAGCAAA | 3240 |
| TGTACTTATT | TTCAAACATT | ACTGCCTAGC | TTTAATTGAC | GTTATATTAA | CTATAAACTA | 3300 |
| CTTTTCCATG | ACTCTACGGA | TTCAATGTCA | CATGAGCGTG | ATAAATTTG | TTCAATAATA | 3360 |
| AAGTCATGTT | TATCATCTGA | TCTATCACCA | ACAGCATCTT | CTAAAACAGT | AATATAATAG | 3420 |
| TCTTTATCTA | CACTTTCTAA | TGCCGTGCTC | AATACAGCTC | CACTCGTAGA | GACACCCGTT | 3480 |
| AATACTAAAT | GATTAATATC | ATTTGCACGT | AAATAAACTT | CCAAGTAACT | ACCTGTAAAT | 3540 |
| GCGCTAAAGC | GTCGCTTAGA | AATAATCGGC | TCATCTTCTA | GTGGTGCTAA | ATCTTCAAGT | 3600 |
| ATTCGTGTAG | ATGCATCTGC | TTCAGTAATC | GCATATCCTT | GAGCTTTAAT | TGTTGAAAAC | 3660 |
| ACTTTATTAC | TCGAGGAGAC | ATCATTAAAA | TGCTTATCTA | ACACTAAACG | TATGAAAATG | 3720 |
| ACTGGTATTC | GATGTTGTCT | TGCTGCTTCA | ATTGCTCTCT | GATTCGCTTT | AATAATATTT | 3780 |
| TTTATTCTAG | GTACACTACT | CGCTATACTT | CTTGCATATC | CAAACTAATA | GCGCCGTTTT | 3840 |
| TCGAGACATC | TTCATTCTCC | TTTACTTCTG | TAGTTCTAAG | TCGTTAAATT | CATTATAACG | 3900 |
| TTAAAATGAT | GGACAATCTA | TTCATTGCAT | TTTGCATATA | CTTCACAATA | ATTTAAGGGG | 3960 |
| GAAATAAGAC | GTCTTATATA | CTTAAAAAAA | TATATAGATG | CTCTTCCCCC | AATATAATTA | 4020 |
| TGCTTTATTT | TTCAACTTAT | TGCGTCGTGA | TAACCAAATC | ATTAGTACAC | CCATTGCACC | 4080 |

| | | | | | | |
|---|---|---|---|---|---|---|
| AACAATTACA | GATATCGGCA | ACCAATGTTC | TTTTATCGTT | TCCCCGCTTT | AGGCAAGATA | 4140 |
| CATTACCATC | AGCATTTAAT | AATCCACTTA | ACAATCCATT | ACCTTTACCA | AGTGTTACGT | 4200 |
| CTTTTCTGGC | TTTGGTGTGG | GTATATCTGG | AATACTGTCT | AATAAATTTG | ATCCTTGATT | 4260 |
| CATTAAATTT | GCTAACTTAT | TTAAATCCGT | TGTTTTCCCA | TTTTTATTCA | ATCGATCTAG | 4320 |
| TAAACTTGGA | CGATTACTA | TTGGTGATAA | AATATAGTCT | ATATCTTTTT | TCGTTTGATT | 4380 |
| GAGTCTCTTT | TGTAAATTCA | ATAAATCATC | CGCTTTACCA | TTCAATGCCG | ATTTAACTAA | 4440 |
| ATTAAAATT | TTATTTTGAT | CTGTTTCTAT | TTTAGTAATT | AAATCTGCCA | GTAATTTTGC | 4500 |
| CTTTTGTCTT | TCTATACGTG | TTGCTAAAAT | CGTTTCAATT | GCTTGCTTTT | TATCTTTGGC | 4560 |
| ATTATTCAAA | ATTGCTTTTA | ATATATCATC | TGAAGACGTG | TCGCCAGTTG | ATGCAAAATG | 4620 |
| TTTCTTCAAT | TGGTCAACGA | TTTGGCGATT | TGATAATCCT | TTATTCGTCC | AATCTTTAGC | 4680 |
| CAATTTATCT | GCTTCAGCTT | TTCCTAATTT | CGTTTGTAAG | ATTTGAGAAA | TCAATAGCGA | 4740 |
| CTTATCTTGT | GATTGATCAA | TCAATGACGT | TAATAAATCA | TCACTCGTTG | TCAGAGATAG | 4800 |
| TTGATCAATA | TGACGAGTAA | TTTGATCTGC | AATTTGTTGA | TCTGTTTTAC | CATCAACACG | 4860 |
| TATATCTTTT | AGAATTTTAT | CTGCCTCGTC | TTTATTAAAT | ATACTTCTA | AAATGCTTTG | 4920 |
| TGTAGCATAC | TTTTTATCAT | CAGTACGTGC | AAGTTCTTCC | AAAATAATAT | TCGTTGACT | 4980 |
| TTTTATACGC | TCTTTCGTCT | TATTTACTTC | GCTCATTAAG | TCTGATTTTT | GATTTTAGG | 5040 |
| AAGTTGCGTA | TTTGCAATAC | GTTGATCTAA | AGATTGTAAC | GTATTCAGTT | TATGATATGT | 5100 |
| GTAATGTTGC | GTTGAGGCAT | TACTTTTAGC | CAATTTTTCA | ATCATAGCAT | GATTAATTTT | 5160 |
| ATCGCTTCCT | TGTAATTTAT | CAGTGAGTTG | ATTACTATGG | CTTTGATTCT | CTTCATTTGA | 5220 |
| AAGAAATTTA | TTTAACACAA | CATGTCCAGA | ACCATCATTA | TTTGGCGTTT | TAGCTACTTC | 5280 |
| ATGATTACTA | TCTGTTGTAG | ACACTGCCGG | ATCTTTCGAT | GCATCTTTCA | ATGCATCTTT | 5340 |
| CGATTTGTGT | ATTTGCTGAT | TCAAATGGTC | TAGGTCTTCT | AACGCCTTAT | TTACCATTGC | 5400 |
| TTCATCATTT | TTATCATCTT | TTTCTCCATA | TTTTGTTGTA | GCCGTTTGTG | ACATATCATT | 5460 |
| TTTCATTGCA | TTAAGATCGT | CCTCGCCACT | TTGTTGACCC | CTATCAACAT | TTGAAGAAAC | 5520 |
| CTCATTTAAA | TCTTTAAGCA | ATTGATCTAA | TTTACTGTCT | ATATCACTTT | GACCGTTCAT | 5580 |
| TTCAGTGTGA | GAACTTTTAT | TTTCTTTGCT | ATCCAACTCA | TTAGCTCGTT | TTATGATTTC | 5640 |
| ATCTATTTGC | GATGCTGTTT | TCGCTTCATT | TAGTTGTGCT | TTATAATGTG | CTTTAGATGA | 5700 |
| AGCCGATAAC | TGTTTTAATT | GCTCAATTTG | ACGAATTGCT | TTGTCAACTT | TGTCTAATAA | 5760 |
| ATCTTGCTTA | GATAATATCT | CTTTTGAAAT | TTCAGTATCC | TTTTCAGATG | CAGCTTGGGC | 5820 |
| ATCGTACGGC | AAGATATTCG | TTAAAATGAT | ACTTGACGCC | ATCATTGTCG | AACACGATAA | 5880 |
| CTTTACATAT | AATTGAAACG | GTTTCCCTCG | ATATTTAGCC | ATCAACATAC | TCCTTTCTCA | 5940 |
| CTTACTTCCT | TCAAAGAATT | ACATACTATT | ATATACCTGT | TTACAAGAAA | TTTACACTTA | 6000 |
| TCTATCTAGT | TATTGTTGTT | AGTAATTATC | AACTTATTAC | TTAGCTTATA | TTTAAGTAAA | 6060 |
| CAAAAAGCA | TGACGTAATA | TCATATTGTC | CATGTCGCTA | ACATCATATT | ACGTCAAATC | 6120 |
| TTTTAAATTA | AATGATGCTT | TATTTTAGAC | TGCTTTTTCT | TTTTAGCTTT | CGAGCGCCTG | 6180 |
| TTTAAAAACT | TGCTCGAATT | GTTCACGCGA | GATTTCGTGT | GCATGTGCTT | TTTGTGCTAA | 6240 |
| TAAAGCATCT | CGAAACTGTT | GTTGATCTTT | CAAACTTTCT | AACATTTGTA | TTAATTGGTC | 6300 |
| TTTACTTTCC | ATTGTTATCT | CATCATTATG | CTCAAATAAG | TGCTCTGATA | ATGTTACTTT | 6360 |
| AGCATGGTGT | GCGGTTTGAC | GATAACCTAA | AATCAACAAC | TCATAGTCAA | ACGCTTGTTC | 6420 |
| CACCGCATTT | AAAATTTCAT | TACCCTCATT | GATATCAAGA | TAAATATCAC | ATAACTGGTA | 6480 |

```
TAGTTCATTT ACCCTGTCAA TATAATAGAT GGTATAAGTG CACATTAGCA TATTGATCAA    6540
GTTGCATTAG CTTATCAGAC ATCTCTGTAA TAGCAGCGAT GTGAAAATTA AAATCTGGTA    6600
AAGTTTCAAC CAATACCTTG ATGTTACGAA GTTGATCCGA GTTAGTTAAT ATTACAATTT    6660
CTTTAGTATA TCTATTACGA CTACGATAGT TATATAGATA TCCGCCTTGT AAAATACGAG    6720
ATTGAACCTT TGCGTCTGCT ATATTGAGCA TCGTTTCATA TTCGTTTTTA TCTGGAATAA    6780
TAATATTACA ATGTCGTTTC ATATCACCTT TACACATCAA TTGCATATTT CCCGGGACAT    6840
TACCATTACA GTGTTCTTGC CATACCAAAA CATCACTACC TTTTGATGGC AAATTATATA    6900
ACACTGAAAA TGGTAGGGCT AGTGAGTTAA TAACGAAATG ATGTTCCGTA ATTTCAAGTT    6960
GCTTGATAAA AAATAATACG AATGCGAGCT TTGAAGGGAA AAAGTAAGAC TTCCCTTGCC    7020
AATCCAATAT GACATCAGAT GTTACAAAAT TTTCATAAAT CACTTCTTTA CCTTCTGCTG    7080
TCATATATTT CTTCAAGATC GCTTTACGAT TTAAATCGTA ACAGTTGTG CAATTTAATA    7140
CCATTCTTAG AATAATAATC GACAAATCGG ACACGTTGTT GGTCATCAAA CCATTCGACA    7200
CGACTAACAA TTCTAGGGCG CTCTCCACTT TGATAAAATA TTTTGCCTCG TAGACGTCCC    7260
ATATCATTAA TTGTAGCCGA ATTGTTGTTA CCTTTAATTT CCCAAAAAGC TGGTACAGTA    7320
ACCTGATTAA AAAATCGTGG TTTCATATTT TCTGTATTAT GATTATCTGC AAAAAATTGA    7380
TACGGTGATA TAACATCGTC CGGTAAAAAG CCATTGTCAT TGAGTACAAT TGTTAAATCT    7440
TCTTCCAACT TACTGGCTTT AAAAGACTCA TATAACTTTC GTGAATGATC GTTAAAGTAA    7500
TCAAATAATT TAATCATGTA GCACCTCTTG AACTAATGTT TCCCATTTTA AAATAATATC    7560
TTGAGTCATA AATTGCTGTG CCACTTCATA AGAGATGTCA TGTGGTGCCT GGGGACCATT    7620
GTTAAAATAC ATTACAATGG CATGAGCTAG TTTTGCGATA ACATCATCCA CACTATCTTC    7680
GTCGGTATCA AAAGGTACCA AGTAGCCATT TTCCCCATCT CGAATAAAGG TTGGGTTACC    7740
ATAATTCACA TTTAATCCAA TCATACCTAG TCCTGAGCCT ACCGCTTCCA TTAGTGTTAA    7800
CCCAAAACCT TCGCTAGTTG ATGCAGAAAG AAATAACTCA TAATCATTAT AAATTTCATC    7860
AAGTTTAACA TGCCCTTAGT AAACCGAATA TAATCTTGTG CGCGGTGTGT ATCAATAATT    7920
TTACGCAGTC GCGTCTTCTC GCTACCTTCT CCATAAATAT CAAATGTTAA TTCTGGCACT    7980
TGTCGTTTAG CCACGATAAC CGCCTTGACA AGCCAATCAA TATGTTTCTC ATTTGCTAAA    8040
CGAGATGCAC TAATCATCGC ATATGGCTTT CTTGATAATT TAGGATATGA TAACGCATCA    8100
ATGCTTCCCA CCGGDATAGT ATAGACACGT GGACGATAAC CTTGATATTG CTCAAATTGT    8160
CGACAAACCA TATGATTTTG AATATCTGTT GCTGTAATAA AGAAATCAAT GTATTTAGCT    8220
TTTGAAAATT GATATTCATA ATAATTGTTC CATAGTATAT GCTGCTCGCT CATCATATTA    8280
TTACTATAAT GATCAGCATG AATCACAACA CCAACTTTAC TATCACCTTT ATGCTGCAAA    8340
ACAGCCTGAC CAATATCAGA AGCGCGGTCT AATATGACAA TATCGTCTCG GGTTAAATTC    8400
AATCGTTGTA AAAAGTATGC AATAAATTCC GTTTTGTTAT ACAACACCGC ATCTTCAAAC    8460
ACATATATAG AGCTGTCTCC ATCAATATAT TCGTTATAAG CGATGGAACC ATCTTCATTA    8520
TAGAATTGTC GCATATATAA TTTCGCTTTA TTATCAGCTG GTGCATAATA CTCAGAAAAT    8580
ATACGCGTAT AACTATAAAA ATCTTTACGT ACTAACATAC TATTAATTAC AATTCTGCAC    8640
GATCCACAAC ATCTTTTTGT TCATTTTGTA GATAACATGT TACAAATGAT GATTTCCCAT    8700
TAAAATATAG ACGGACTATC TTACCATTTC TTTCTCTAAA ACTAATTTCA TGACCAAGCT    8760
CACGTTCAAT GTCATCTAAC GTGTACGTTG TTGGTGCTAT AGAAATATCA CTAAAAATAC    8820
TGATACAACC AAATAACTTC TTGATCTTTA AACCCAATGT TTTGCGTTAA TGTCTGTATG    8880
```

| | | | | | | |
|---|---|---|---|---|---|---|
| TTCTCTGACT | GTATAAAATC | TAAAAACACA | AATTTAGTGT | CTTGATTTGT | ACGTCTCAAT | 8940 |
| AATTTAGCAC | GGTAAGCTT | | | | | 8959 |

( 2 ) INFORMATION FOR SEQ ID NO:2:

( i ) SEQUENCE CHARACTERISTICS:
        ( A ) LENGTH: 10207 base pairs
        ( B ) TYPE: nucleic acid
        ( C ) STRANDEDNESS: double
        ( D ) TOPOLOGY: linear ( i i ) MOLECULE TYPE:Genomic DNA ( v i ) ORIGINAL SOURCE:
        ( A ) ORGANISM: Staphylococcus aureus
        ( B ) STRAIN: Clinical Isolate SA- 24

( x i ) SEQUENCE DESCRIPTION: SEQ ID NO:2:

| | | | | | | |
|---|---|---|---|---|---|---|
| AAGCTTATGG | ACCTATTTTA | GGTATATTGA | TTAGTTGGCT | TGGATTAATT | TCTGGAACAT | 60 |
| TTACAGTCTA | TTTGATCTGT | AAACGATTGG | TGAACACTGA | GAGGATGCAG | CGAATTAAAC | 120 |
| AACGTACTGC | TGTTCAACGC | TTGATTAGTT | TTATTGATCG | CCAAGGATTA | ATCCCATTGT | 180 |
| TTATTTTACT | TTGTTTTCCT | TTTACGCCAA | ATACATTAAT | AAATTTTGTA | GCGAGTCTAT | 240 |
| CTCATATTAG | ACCTAAATAT | TATTTCATTG | TTTTGGCATC | ATCAAAGTTA | GTTTCAACAA | 300 |
| TTATTTTAGG | TTATTTAGGT | AAGGAAATTA | CTACAATTTT | AACGCATCCT | TTAAGAGGGA | 360 |
| TATTAATGTT | AGTTGTGTTG | GTTGTATTTT | GGATTGTTGG | AAAAAAGTTA | GAACAGCATT | 420 |
| TTATGGGATC | GAAAAAGGAG | TGACATCGTG | AAAAAAGTTG | TAAAATATTT | GATTTCATTG | 480 |
| ATACTTGCTA | TTATCATTGT | ACTGTTCGTA | CAAACTTTTG | TAATAGTTGG | TCATGTCATT | 540 |
| CCGAATAATG | ATATGTCACC | AACCCTTAAC | AAAGGGACGT | GTTATTGTAA | ATAAAATTAA | 600 |
| AGTTACATTT | AATCAATTGA | ATAATGGTGA | TATCATTACA | TATAGGCGTG | GTAACGAGAT | 660 |
| ATATACTAGT | CGAATTATTG | CCAAACCTGG | TCAATCAATG | GCGTTTCGTC | AGGGACAATT | 720 |
| ATACCGTGAT | GACCGACCGG | TTGACGCATC | TTATGCCAAG | AACAGAAAAA | TTAAAGATTT | 780 |
| TAGTTTGCGC | AATTTTAAAG | AATTAGATGG | AGATATTATA | CCGCCTAACA | ATTTTGTTGT | 840 |
| GCTAAATGAT | CATGATAACA | ATCAGCATGA | TTCTAGACAA | TTTGGTTTAA | TTGATAAAAA | 900 |
| GGATATTATT | GGTAATATAA | GTTTGAGATA | TTATCCTTTT | TCAAAATGGA | CGATTCAGTT | 960 |
| CAAATCTTAA | AAAGAGGTGT | CAAAATTGAA | AAAGAATTA | TTGGAATGGA | TTATTTCAAT | 1020 |
| TGCAGTCGCT | TTTGTCATTT | TATTTATAGT | AGGTAAATTT | ATTGTTACAC | CATATACAAT | 1080 |
| TAAAGGTGAA | TCAATGGATC | CAACTTTGAA | AGATGGCGAG | CGAGTAGCTG | TAAACATTAT | 1140 |
| TGGATATAAA | ACAGGTGGTT | TGGAAAAAGG | TAATGTAGTT | GTCTTCCATG | CAAACAAAAA | 1200 |
| TGATGACTAT | GTTAAACGTG | TCATCGGTGT | TCCTGGTGAT | AAAGTAGAAT | ATAAAAATGA | 1260 |
| TACATTATAT | GTCAATGGTA | AAAACAAGA | TGAACCATAT | TTAAACTATA | ATTTAAAACA | 1320 |
| TAAACAAGGT | GATTACATTA | CTGGGACTTT | CCAAGTTAAA | GATTTACCGA | ATGCGAATCC | 1380 |
| TAAATCAAAT | GTCATTCCAA | AAGGTAAATA | TTTAGTTCTT | GGAGATAATC | GTGAAGTAAG | 1440 |
| TAAAGATAGC | CGTGCGTTTG | GCCTCATTGA | TGAAGACCAA | ATTGTTGGTA | AAGTTTCATT | 1500 |
| TAGATTCTGG | CCATTTAGTG | AATTTAAACA | TAATTTCAAT | CCTGAAAATA | CTAAAAATTA | 1560 |
| ATATGAAACA | AATACAACAT | CGTTTGTCGG | TTTTAATACT | GATAAACGAT | GTTTTATTTT | 1620 |
| GTTAGTACCA | CAATAAAAGC | TAAGTTCGAA | ATGAACTTAT | AATAAATCAA | TCACAATCAC | 1680 |
| TTTGTGTTAA | AATATGTGTC | AAAGGAAGTG | AGGGTTTGTC | ATGACATTAC | ATGCTTATTT | 1740 |
| AGGTAGAGCG | GGAACAGGTA | AGTCTACGAA | AATGTTGACC | GAAATAAAAC | AAAAAATGAA | 1800 |

-continued

| | | | | | | |
|---|---|---|---|---|---|---|
| AGCAGATCCG | CTTGGAGATC | CAATCATTTT | AATTGCGCCA | ACTCAAAGTA | CATTTCAATT | 1860 |
| AGAACAAGCC | TTTGTCAATG | ATCCGGAATT | AAATGGTAGT | TTAAGAACAG | AAGTGTTGCA | 1920 |
| TTTTGAACGA | TTAAGTCATC | GTATTTTCCA | AGAAGTTGGT | AGTTATAGCG | AACAAAGTT | 1980 |
| ATCTAAAGCT | GCAACGGAAA | TGATGATTTA | TAACATTGTT | CAAGAACAAC | AAAAGTATTT | 2040 |
| AAAACTTTAT | CAATCACAAG | CAAATATTA | TGGGTTTAGT | GAAAAATTAA | CAGAACAAAT | 2100 |
| TCAAGATTTT | AAAAAATATG | CAGTAACGCC | TGAACATTTA | GAACACTTTA | TTGCTGATAA | 2160 |
| AAATATGCAA | ACTCGAACTA | AAAATAAGTT | AGAGGATATT | GCTTAATAT | ACCGTGAGTT | 2220 |
| CGAACAACGC | ATTCAAAACG | AGTTTATTAC | TGGTGAGGAT | TCATTACAAT | ATTTTATTGA | 2280 |
| TTGTATGCCG | AAATCAGAGT | GGCTAAAACG | TGCTGATATA | TATATTGATG | GTTTTCACAA | 2340 |
| CTTTTCAACG | ATTGAGTATT | TAATAATCAA | AGGATTAATT | AAATATGCGA | GAGTGTCACA | 2400 |
| ATTATATTGA | CGACAGATGG | TAACCACGAT | CAATTTAGTT | TTTTAGAAAA | CCATCGGAAG | 2460 |
| TGTTACGACA | TATTGAAGAA | ATAGCAAATG | AACTCAATAT | TTCTATTGAA | CGTCAATATT | 2520 |
| TCAACCAATT | ATATCGCTTC | AATAATCAAG | ATTAAAGCA | TCTTGAACAA | GAATTTGATG | 2580 |
| TACTTCAAAT | CAATCGAGTG | GCATGTCAAG | GTCATATCAA | TATTTTAGAA | TCTGCGACTA | 2640 |
| TGAGAGAGGA | AATAAATGAA | ATTGCGCGAC | GTATCATCGT | TGATATTCGT | GATAAGCAAT | 2700 |
| TACGATATCA | AGATATTGCA | ATTTTATATC | GTGACGAGTC | TTATGCTTAT | TTATTTGATT | 2760 |
| CCATATTACC | GCTTTATAAT | ATTCCTTATA | ACATTGATAC | AAAGCGTTCG | ATGACACATC | 2820 |
| ATCCGGTCAT | GGAAATGATT | CGTTCATTGA | TTGAAGTTAT | TCAATCTAAT | TGGCAAGTGA | 2880 |
| ATCCAATGCT | ACGCTTATTG | AAGACTGATG | TGTTAACGGC | ATCATATCTA | AAAAGTGCAT | 2940 |
| ACTTAGTTGA | TTTACTTGAA | AATTTTGTAC | TTGAACGTGG | TATATACGGT | AAACGTTGGT | 3000 |
| TAGATGATGA | GCTATTTAAT | GTCGAACATT | TTAGCAAAAT | GGGGCGTAAA | GCGCATAAAC | 3060 |
| TGACCGAAGA | TGAACGTAAC | ACATTTGAAC | AAGTCGTTAA | GTTAAAGAAA | GATGTCATTG | 3120 |
| ATAAATTTT | ACATTTTGAA | AAGCAAATGT | CACAAGCGGA | AACTGTAAAA | GACTTTGCAA | 3180 |
| CTGCTTTTTA | TGAAAGTATG | GAATATTTCG | AACTGCCAAA | TCAATTGATG | ACAGAGCGAG | 3240 |
| ATGAACTTGA | TTTAAATGGT | AATCATGAAA | AGGCGGAGGA | AATTGATCAA | ATATGGAATG | 3300 |
| GCTTAATTCA | AATCCTTGAC | GACTTAGTTC | TAGTATTTGG | AGATGAACCA | ATGTCGATGG | 3360 |
| AACGTTTCTT | AGAAGTATTT | GATATTGGTT | TAGAACAATT | AGAATTTGTC | ATGATTCCAC | 3420 |
| AAACATTAGA | TCAAGTTAGT | ATTGGTACGA | TGGATTTGGC | TAAAGTCGAC | AATAAGCAAC | 3480 |
| ATGTTTACTT | AGTTGGAATG | AACGACGGCA | CCATGCCACA | ACCAGTAACT | GCATCAAGTT | 3540 |
| TAATTACTGA | TGAAGAAAAG | AAATATTTTG | AACAACAAGC | AAATGTAGAG | TTGAGTCCTA | 3600 |
| CATCAGATAT | TTTACAGATG | GATGAAGCAT | TTGTTTGCTA | TGTTGCTATG | ACTAGAGCTA | 3660 |
| AGGGAGATGT | TACATTTTCT | TACAGTCTAA | TGGGATCAAG | TGGTGATGAT | AAGGAGATCA | 3720 |
| GCCCATTTTT | AAATCAAATT | CAATCATTGT | TCAACCAATT | GGAAATTACT | AACATTCCTC | 3780 |
| AATACCATGA | AGTTAACCCA | TTGTCACTAA | TGCAACATGC | TAAGCAAACC | AAAATTACAT | 3840 |
| TATTTGAAGC | ATTGCGTGCT | TGGTTAGATG | ATGAAATTGT | GGCTGATAGT | TGGTTAGATG | 3900 |
| CTTATCAAGT | AATTAGAGAT | AGCGATCATT | TAAATCAAGG | TTTAGATTAT | TTAATGTCAG | 3960 |
| CATTAACGTT | TGACAATGAA | ACTGTAAAAT | TAGGTGAAAC | GTTGTCTAAA | GATTTATATG | 4020 |
| GTAAGGAAAT | CAATGCCAGT | GTATCTCGTT | TTGAAGGTTA | TCAACAATGC | CCATTTAAAC | 4080 |
| ACTATGCTTC | ACATGGTCTG | AAACTAAATG | AACGAACGAA | ATATGAACTT | CAAAACTTTG | 4140 |
| ATTTAGGTGA | TATTTTCCAT | TCCGTTTTAA | AATATATATC | TGAACGTATT | AATGGCGATT | 4200 |

```
TTAAACAATT AGACCTGAAA AAAATAAGAC AATTAACGAA TGAAGCATTG GAAGAAATTT    4260
TACCTAAAGT TCAGTTTAAT TTATTAAATT CTTCAGCTTA CTATCGTTAT TTATCAAGAC    4320
GCATTGGCGC TATTGTAGAA ACAACACTAA GCGCATTAAA ATATCAAGGC ACGTATTCAA    4380
AGTTTATGCC AAAACATTTT GAGACAAGTT TTAGAAGGAA ACCAAGAACC AAATGTACGA    4440
ATTAATTGCA CAAACATTAA CGACAACTCA AGGTATTCCA ATTAATATTA GAGGGCAAAT    4500
TGACCGTATC GATACGTATA CAAAGAATGA TACAAGTTTT GTTAATATCA TTGACTATAA    4560
ATCCTCTGAA GGTAGTGCGA CACTTGATTT AACGAAAGTA TATTATGGTA TGCAAATGCA    4620
AATGATGACA TACATGGATA TCGTTTTACA AAATAAACAA CGCCTTGGAT TAACAGATAT    4680
TGTGAAACCA GGTGGATTAT TATACTTCCA TGTACATGAA CCTAGAATTA AATTTAAATC    4740
ATGGTCTGAT ATTGATGAAG ATAAACTAGA ACAAGATTTA ATTAAAAGT TTAAGCTGAG    4800
TGGTTTAGTG AATGCAGACC AAACTGTTAT TGATGCATTG GATATTCGTT TAGAACCTAA    4860
ATTCACTTCA GATATTGTAC CAGTTGGTTT GAATAAAGAT GGCTCTTTGA GTAAACGAGG    4920
CAGCCAAGTG GCAGATGAAG CAACAATTTA TAAATTCATT CAGCATAACA AGAGAATTT    4980
TATAGAAACA GCTTCAAATA TTATGGATGG ACATACTGAA GTGCACCATT AAAGTACAAA    5040
CAAAAATTGC CATGTGCTTT TTGTAGTTAT CAATCGGTAT GTCATGTAGA TGGCATGATT    5100
GATAGTAAGC GATATCGAAC TGTAGATGAA ACAATAAATC CAATTGAAGC AATTCAAAAT    5160
ATTAACATTA ATGATGAATT TGGGGGTGAG TAATAGATGA CAATTCCAGA GAAACCACAA    5220
GGCGTGATTT GGACTGACGC GCAATGGCAA AGTATTTACG CAACTGGACA AGATGTACTT    5280
GTTGCAGCCG CGGCAGGTTC AGGTAAAACA GCTGTACTAG TTGAGCGTAT TATCCAAAAG    5340
ATTTTACGTG ATGGCATTGA TGTCGATCGA CTTTTAGTCG TAACGTTTAC AAACTTAAGC    5400
GCACGTGAAA TGAAGCATCG TGTAGACCAA CGTATTCAAG AGGCATCGAT TGCTGATCCT    5460
GCAAATGCAC ACTTGAAAAA CCAACGCATC AAAATTCATC AAGCACAAAT ATCTACACTT    5520
CATAGTTTTT GCTTGAAATT AATTCAACAG CATTATGATG TATTAAATAT TGACCCGAAC    5580
TTTAGAACAA GCAGTGAAGC TGAAAATATT TTATTATTAG AACAAACGAT AGATGAGGTC    5640
ATAGAACAAC ATTACGATAT CCTTGATCCT GCTTTTATTG AATTAACAGA ACAATTGTCT    5700
TCAGATAGAA GTGATGATCA GTTTCGAATG ATTATTAAAC AATTGTATTT CTTTAGCGTT    5760
GCAAATCCAA ATCCTACAAA TTGGTTGGAT CAATTGGTGA CACCATACGA AGAAGAAGCA    5820
CAACAAGCGC AACTTATTCA ACTACTAACA GACTTATCTA AAGTATTTAT CACAGCTGCC    5880
TATGATGCTT TAAATAAGGC GTATGATTTG TTAGTATGA TGGATGGCGT CGATAAACAT    5940
TTAGCTGTTA TAGAAGATGA ACGACGTTTA ATGGGGCGTG TTTTAGAAGG TGGTTTTATT    6000
GATATACCTT ATTTAACTGA TCACGAATTT GGCGCGCGTT TGCCTAATGT AACAGCGAAA    6060
ATTAAAGAAG CAAATGAAAT GATGGTCGAT GCCTTAGAAG ATGCTAAACT TCAGTATAAA    6120
AAATATAAAT CATTAATTGA TAAAGTGAAA AATGATTACT TTTCAAGAGA AGCTGATGAT    6180
TTGAAAGCTG ATATGCAACA ATTGGCGCCA CGAGTAAAGT ACCTTGCGCG TATTGTGAAA    6240
GATGTTATGT CAGAATTCAA TCGAAAAAAG CGTAGCAAAA ATATTCTGGA TTTTTCTGAT    6300
TATGAACAAT TTGCATTACA AATTTTAACT AATGAGGATG GTTCGCCTTC AGAAATTGCC    6360
GAATCATACC GTCAACACTT TCAAGAAATA TTGGTCGATG AGTATCAAGA TACGAACCGG    6420
GTTCAAGAGA AAATACTATC TTGCATCAAA ACGGGTGATG AACATAATGG TAATTTATTT    6480
ATGGTTGGAG ATGTTAAGCA ATCCATTTAT AAATTTAGAC AAGCTGATCC AAGTTTATTT    6540
ATTGAAAAGT ATCAACGCTT TACTATAGAT GGAGATGGCA CTGGACGTCG AATTGATTTG    6600
```

```
TCGCAAAACT  CCGTTCTCGA  AAAGAAGTAC  TGTCAACGAC  TAACTATATA  TCAAACATAT   6660
GATGGATGAA  CAAGTCGGTG  AAGTAAAATA  TGATGAAGCG  GCACAGTTGT  ATTATGGTGC   6720
ACCATATGAT  GAATCGGACC  ATCCAGTAAA  CTTAAAAGTG  CTTGTTGAAG  CGGATCAAGA   6780
ACATAGTGAT  TTAACTGGTA  GTGAACAAGA  AGCGCATTTT  ATAGTAGAAC  AAGTTAAAGA   6840
TATCTTAGAA  CATCAAAAAG  TTTATGATAT  GAAAACAGGA  AGCTATAGAA  GTGCGACATA   6900
CAAAGATATC  GTTATTCTAG  AACGCAGCTT  TGGACAAGCT  CGCAATTTAC  AACAAGCCTT   6960
TAAAAATGAA  GATATTCCAT  TCCATGTGAA  TAGTCGTGAA  GGTTACTTTG  AACAAACAGA   7020
AGTCCGCTTA  GTATTATCAT  TTTTAAGAGC  GATAGATAAT  CCATTACAAG  ATATTTATTT   7080
AGTTGGGTTA  ATGCGCTCCG  TTATATATCA  GTTCAAAGAA  GACGAATTAG  CTCAAATTAG   7140
AATATTGAGT  CAAATGATGA  CTACTTCTAT  CAATCGATTG  TAAATTACAT  TAATGACGAA   7200
GCAGCAGATG  CTATTTTAGT  TGATAAATTA  AAAATGTTTT  TATCAGATAT  TCAAAGTTAC   7260
CAACAATATA  GTAAAGATCA  TCCGGTGTAT  CAGTTAATTG  ATAAATTTTA  TAATGATCAT   7320
TATGTTATTC  AATACTTTAG  TGGACTTATT  GGTGGACGTG  GACGACGTGC  AAACCTTTAT   7380
GGTTTATTTA  ATAAAGCTAT  CGAGTTTGAG  AATTCAAGTT  TTAGAGGTTT  ATATCAATTT   7440
ATTCGTTTTA  TCGATGAATT  GATTGAAAGA  GGCAAAGATT  TTGGTGAGGA  AAATGTAGTT   7500
GGTCCAAACG  ATAATGTTGT  TAGAATGATG  ACAATTCATA  GTAGTAAAGG  TCTAGAGTTT   7560
CCATTTGTCA  TTTATTCTGG  ATTGTCAAAA  GATTTTAATA  AACGTGATTT  GAAACAACCA   7620
GTTATTTTAA  ATCAGCAATT  TGGTCTCGGA  ATGGATTATT  TTGATGTGGA  TAAAGAAATG   7680
GCATTTCCAT  CTTTAGCTTC  GGTTGCATAT  AAAGCTGTTG  CCGAAAAAGA  ACTTGTGTCA   7740
GAAGAAATGC  GATTAGTCTA  TGTAGCATTA  ACAAGAGCGA  AGAACAACT   TTATTTAATT   7800
GGTAGAGTGA  AAAATTGATA  AATCGTTACT  AGAACTAGAG  CAATTGTCTA  TTTCTGGTGA   7860
GCACATTGCT  GTCAATGAAC  GATTAACTTC  ACCAAATCCG  TTCCATCTTA  TTTATAGTAT   7920
TTTATCTAAA  CATCAATCTG  CGTCAATTCC  AGATGATTTA  AAATTTGAAA  AAGATATAGC   7980
ACAAGTTGAA  GATAGTAGTC  GTCCGAATGT  AAATATTTCA  ATTATATACT  TTGAAGATGT   8040
GTCTACAGAA  ACCATTTTAG  ATAATAATGA  ATATCGTTCG  GTTAATCAAT  TAGAAACTAT   8100
GCAAAATGGT  AATGAGGATG  TTAAAGCACA  AATTAAACAC  CAACTTGATT  ATCAATATCC   8160
ATATGTAAAT  GATACTAAAA  AGCCATCCAA  AACAATCTGT  TTCTGAATTG  AAAAGGCAAT   8220
ATGAAAGAAG  AAAGTGGCAC  AAGTTACGAA  CGAGTAAGAC  AATATCGTAT  CGGTTTTCAA   8280
CGTATGAACG  ACCTAAATTT  CTAAGTGAAC  AAGGTAAACG  AAAAAGCGAA  TTGAAATTGG   8340
TACGTTAATG  CATACAGTGA  TGCAACATTT  ACCATTCAAA  AAGAACGCA   TATCTGAAGT   8400
TGAGTTACAT  CAGTATATCG  ATGGATTAAT  CGATAAACAT  ATTATCGAAG  CAGATGCGAA   8460
AAAAGATATC  CGTATGGATG  AAATAATGAC  ATTATCAATA  GTGAGTATAT  TCGATTATTG   8520
CTGAAGCAGA  GCAAGTTTAT  CGTGAATTAC  CGTTTGTAGT  TAACCAAGCA  TTAGTTGACC   8580
AATTGCCACA  AGGAGACGAA  GACGTCTCAA  TTATTCAAGG  TATGATTGAC  TTAATCTTTG   8640
TTAAAGATGG  TGTGCATTAT  TTTGTAGACT  ATAAAACCGA  TGCATTTAAT  CGTCGCCGTG   8700
GGATGACAGA  TGAAGAAATT  GGTACACAAT  TAAAAAATAA  ATATAAGATA  CAGATGAAAT   8760
ATTATCAAAA  TACGCTTCAA  ACGATACTTA  ATAAAGAAGT  TAAAGGTTAT  TTATACTTCT   8820
TCAAATTTGG  TACATTGCAA  CTGTAGTATT  TTGATTTCA   AAAGAATAAA  AATAATTTC    8880
GATTAAGTGC  AAAGTCCTTG  TAGCAGAATG  AACACAACTC  ATTTTCAAAA  TTGTCTTACT   8940
TATTTATTTG  TTATTTGATA  ACGAAAAAAG  TTATAATGTG  AATTAAGATA  AAGATGAGGA   9000
```

-continued

| | | | | | |
|---|---|---|---|---|---|
| GTTGAGAATG | AATGAAATTC | TTATCATTCA | AGTATAATGA | CAAAACTTCA | TATGGCGTTA | 9060 |
| AAGTAAAACG | CGAAGATGCT | GTATGGGATT | TAACACAAGT | ATTTGCTGAC | TTTGCAGAAG | 9120 |
| GAGATTTCCA | TCCTAAAACA | TTGTTAGCTG | GTTACAACA | AAATCATACT | TTAGATTTTC | 9180 |
| AAGAACAAGT | ACGTAAAGCA | GTTGTAGCAG | CAGAAGATAG | CGGCAAAGCT | GAAGACTATA | 9240 |
| AAATTTCATT | TAATGACATT | GAATTCTTAC | CACCAGTAAC | ACCTCCGAAT | AATGTGATTG | 9300 |
| CTTTTGGTAG | AAATTACAAA | GATCATGCGA | ACGAATTAAA | TCATGAAGTA | GAAAAATTAT | 9360 |
| ATGTATTTAC | AAAAGCAGCG | TCATCTTTAA | CAGGAGATAA | TGCAACAATT | CCAAATCATA | 9420 |
| AAGATATTAC | TGATCAATTA | GATTATGAAG | GTGAATTAGG | TATTGTTATT | GGTAAGTCTG | 9480 |
| GTGAAAAGAT | TCCAAAAGCA | TTAGCTTTAG | ATTATGTTTA | CGGCTATACA | ATTATTAACG | 9540 |
| ATATCACTGA | TCGCAAAGCA | CAAAGTGAAC | AAGATCAAGC | ATTTTATCA | AAAAGTTTAA | 9600 |
| CTGGCGGTTG | CCCAATGGGT | CCTTATATCG | TTACTAAAGA | CGAACTACCA | TTACCTGAAA | 9660 |
| ATGTAAATAT | TGTTACAAAA | GTTAACAATG | AAATTAGACA | AGATGGTAAC | ACTGGCGAAA | 9720 |
| TGATTCTTAA | AATTGATGAA | TTAATAGAAG | AAATTTCAAA | ATATGTTGCA | CTACTACCGG | 9780 |
| GAGATTATTA | TTGCAACTGG | TACACCAGCT | GGCGTTGGTG | CAGGTATGCA | ACCACCTAAA | 9840 |
| TTTTACAAC | CAGGTGATGA | AGTTAAAGTG | ACTATTGATA | ATATTGGAAC | GCTGACAACT | 9900 |
| TATATCGCTA | AATAATTATC | ATTTAAAAAG | CTAACCAGGT | CTTTATATAG | ATTGGTTAGT | 9960 |
| TTTTTCTTGC | TTTTCTAAAA | AGGTGTTAAA | GATAAATTAT | TTATAATGTT | ACCATTTGA | 10020 |
| GATGAAAGTG | AAATATTGAT | ATTAAGAAGT | AGTTGATTAT | TTTACAGCAG | ATTCACAATA | 10080 |
| TTCTAATAAG | GGCAATGCAA | ATGTCATGTT | CTTCCTCTCA | AATATAGAAG | TGTGGTAGAA | 10140 |
| TATATATTCG | TGTATAATCA | AATCTAGATT | AAATTACAAG | CAAGTGGGTA | TTAATCCCAA | 10200 |
| GAAGCTT | | | | | | 10207 |

( 2 ) INFORMATION FOR SEQ ID NO:3:

( i ) SEQUENCE CHARACTERISTICS:
( A ) LENGTH: 2082 base pairs
( B ) TYPE: nucleic acid
( C ) STRANDEDNESS: double
( D ) TOPOLOGY: linear ( i i ) MOLECULE TYPE: Genomic DNA ( v i ) ORIGINAL SOURCE:
( A ) ORGANISM: Staphylococcus aureus
( B ) STRAIN: Clinical Isolate SA- 36

( x i ) SEQUENCE DESCRIPTION: SEQ ID NO:3:

| | | | | | |
|---|---|---|---|---|---|
| AAGCTTTCTA | ATCTATCGTT | AATGATTTGC | TTTAAAATTG | GGTCGAAGTT | AATTGAAGGT | 60 |
| GTGAAGTGTA | TATCTGTATT | AATAACCATG | TCATTCATTT | GCTGCTTCAC | TTTGTTAACA | 120 |
| AGTCTTCCGT | CATATAAAAA | TAATGGTACG | ACAATCAATT | TTTGATACCG | TTTCGAGATG | 180 |
| CTTTCTAAAT | CATGTGTAAA | ACTAATCTCT | CCATATAGCG | TTCTCGCATA | AGTAGGTTTA | 240 |
| TTAATCTGCA | AATGTTGAGC | GCATATTTGT | AACTCTTCGT | GTGCCTTAGT | AAAATTTCCA | 300 |
| TTAATATTGC | CGTGTGCAAC | AACCATAACT | CCAACTTGTT | GTTCGTCACC | TGCTAATGCG | 360 |
| TCACAAATAC | GTTGTTCAAT | TAATCGTCTC | ATTAAAGGAT | GTGTGCCAAG | TGGCTCGCTT | 420 |
| ACTTCTACCT | TTATGTCTGG | ATACCGTCGT | TTCATTTCAT | GAACGATATT | CGGTATATCC | 480 |
| TTGAGATAAT | GCATTGCACT | AAAGATTAGC | AATGGTACAA | TTTTAAAATG | GTCAACCCCA | 540 |
| CTTTGAATCA | ACGTCGTCAT | TACCGTCTCT | AAATCCTGAT | GCTCACTTTC | TAAAAACGCA | 600 |

| ATATCATAGT | GATGTATATC | ATCTTTTACT | AATTCAGAAA | TAAATGCTTC | TAACGCTTGA | 660 |
| ---------- | ---------- | ---------- | ---------- | ---------- | ---------- | --- |
| TTCTGTCGTC | CGTGCCTCAT | GCCATGTGCA | ACAATGATAT | TCCCATTCAC | ATTTACCAAC | 720 |
| CCTTTCACAC | GTATTGTATA | CCAAATCATT | TTGTTTTTGT | GAAAAGAATC | ACATTATAAT | 780 |
| GTAAAATCAG | GGAATTCCCT | GATGCCTGTA | GTCATGCATA | TTCCTTATAC | ATTTTCCCTT | 840 |
| TTTGTTAAAT | CAAAAAAGC | GACCGATATA | TGAATCCCTA | CTCAACATTT | ATTTGAGCAA | 900 |
| GCATCAATAT | ATCGGTCGCT | TGTAGTGTAT | ATTATTATCT | TAAAATGGTG | GTTGGCCTAA | 960 |
| TATTGTTTCG | TCAAAGCGCT | CGGGTATCAA | TACTTTGCGC | ATGATCACAC | CTAAATCGCC | 1020 |
| ATCATCATTT | TCATGTTCGC | TGTATATTTC | ATAACCTCTT | TTTTCATAAA | TTTTAAGTAA | 1080 |
| CCACGGATGC | AATCTTGCAG | ATGTACCTAA | AGTAACTGCC | GCTGACTTTA | ACGTATCTCG | 1140 |
| CAAAAATGCT | CTTCAACATA | AGTAAGTAAT | TGGCTACCAT | AGCCTTTCCC | TTCATACTCA | 1200 |
| GGATTTGTCG | CAAACCACCA | GACAAAGGA | TAGCCCGAAA | TACTTTTCAC | ACTTCCCCAA | 1260 |
| GGATATCTAA | CCGTAATCGT | AGATATAATT | TCATCATCAA | TTGTCATGAC | AAATGTAGTA | 1320 |
| TTTTTATCTA | TATTTTCTTT | AACAGCATCT | AAATTAGCAT | TAACTGAAGG | CCAATCAATA | 1380 |
| CCTAGTTCTC | TTAGAGGCGT | AAATGCTTCA | TGCATGAGTT | GTTGCAATTT | TTCTGCATCT | 1440 |
| TGTTCACTTG | CGAGTCGAAT | CATCGTTTTT | GTCATATTAA | TCCCCACTCT | TTTTTAAATG | 1500 |
| ATTTAACCAT | ATTTTATTTT | TAAAATAAAT | ATCCATCAAA | GTGTATCAAT | AAATTTATCA | 1560 |
| CATGTCAGAA | AGTATGCTTC | ATCTGAATAC | ACCAATACTC | TCATGAAACT | TATTAAAAAT | 1620 |
| TACTCTCTCA | ACGTAAAAAA | ACCATTCAAA | TTCATGAATG | GTTTGGAAGA | ATGATTCATT | 1680 |
| GTTACGCTAT | TTAATCACTA | CATCTTAATT | ATTGTTGCTC | TAAACGATTA | CGCTTACCAT | 1740 |
| TTAAGAAAGC | ATAAACGAGA | CCTACAAAAA | TACCGCCACC | GACAAAGTTA | CCTAAGAAAG | 1800 |
| CAAAAACGAT | ATTTTTTAAA | ACATGTAACC | ATGAAACTGC | ATCAAGGTTA | AAGAATACCA | 1860 |
| TACCTGCATA | TAGACCTGCA | TTGAACACAA | CGTGCTCATA | TCCCATGTAT | ACAAAGACCA | 1920 |
| CGACACCACA | AGCTATGAAG | AATGCCTTTG | TTAAGCCGCC | TTTGAATTGC | ATAGAGATGA | 1980 |
| AAATACCAAT | ATTAATAAAG | AAGTTACAGA | AAATACCTTT | TGTAAAAATA | TTCAACCATG | 2040 |
| TTGAATCAAC | AGTCTTTTTC | TGAACTAAAG | CTGTTAAAGC | TT | | 2082 |

(2) INFORMATION FOR SEQ ID NO:4:

(i) SEQUENCE CHARACTERISTICS:
        (A) LENGTH: 2885 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Staphylococcus aureus
        (B) STRAIN: Clinical Isolate SA- 77

(xi) SEQUENCE DESCRIPTION: SEQ ID NO:4:

| AAGCTTTTGA | TTAATTGGG | CTTTAAAGTA | TTCCCAATTA | TAATTCTTCA | TGATTTTCTT | 60 |
| ---------- | --------- | ---------- | ---------- | ---------- | ---------- | -- |
| ATTGGATTTC | GAATTTGGTT | TCATGCATTG | TTGCCTCAAA | GAACATGCTG | AACAGTCATC | 120 |
| GCATTCATAT | AGCTTGAAGT | CACGTTTAAA | ACCATATCTA | TCATTACGGT | ATGCATATCT | 180 |
| TTTAAAACCT | ATTCTTTTGT | TATTAGGACA | TATAAATTCA | TCATTAAGTT | CGTCATATTT | 240 |
| CCAATTTTGA | GTGTTAAAAA | TGTCACTTTT | AAACTTTCTA | GTTTATCTT | TAATAAACAT | 300 |
| GCCATACGTA | ATAAGTGGCG | TTTTATTAAA | ACATCTATAA | TAGCCATATA | GTTTTGCTCA | 360 |
| CTATCATAAC | TGCATCAGCT | ACATTAACTC | TGGTAATACC | GAGGATTTGA | ATCATTGTTA | 420 |

-continued

```
AAAATGGAAT TAAAGTTCTA GTATCTGTTG GGGTTTGAAA TAGGTCATAG GATAAAAAAA    480
TTGAGAATTT GTCGCTATTT GTAAATTGTA TCCTGGCTTA AGTTGGCCAT TTTTCATATG    540
GTCTTCCTTC ATTCTCATAA AAGTTGCATC ATGATCAGCC CAGAAAGCTA TTTCTATCTT    600
TAAGAATCCA TTTTTGTTCT TCATATTTAT TTTTCTTTC  GGAATAATCA TCAAATTTCT    660
TTTTGAACTT CTTAATCTCA GTTCTTTTTT ACGGGTCTGT TTTCTAATTT GAGCACTCTT    720
CGTTCTAAAT AGAATGATTT AAATCTTCGA TTTCTTTTAT CTAAATGACT ACCAATTAAA    780
TCTATTTCTT CTCGTGATTT TGAATACTTT TCTTCCACAC AAATGTATAT CTATTGGCAT    840
TAGCTTCTAC TTATGTACCA TCAATAAAAA TTGAATTATT ATCAATAAGA TTTTGCTTTA    900
AACATTGACT ATGGAACTGA ATAAATAAAG ATTCAATTAA CGCATCAGTA TTAGGATTCA    960
CTCTAAAACG ATTAATAGTT TTATAAGAAG GTGTTTGATC TTGAGCTAAC CACATCATTC    1020
GAATACTGTC ATGAAGTAAT TTCTCTATTC TACGACCAGA AAATACAGAT TGAGTATATG    1080
CATATAAGAT GATTTTAAC  ATCATTTTG  GATGATAGGA TGTTGCGCCA CGATGATGTC    1140
TGAATTCATC GAATTCGCTA TCAGGTATCG TTTCAACAAT TTCATTACA  TATCGCGAAA    1200
TATCATTTTA AGGAATTCTA ACAGAAGTTT CTATTGGTAG TGTAAGTTGG GCAAAGTGTC    1260
TTATTTTTTT AAAGTATGTA AAAGTAAAAT TACATGTTAA TACGTAGTAT TAATGGCGAG    1320
ACTCCTGAGG GAGCAGTGCC AGTCGAAGAC CGAGGCTGAG ACGGCACCCT AGGAAAGCGA    1380
AGCATTCAAT ACGAAGTATT GTATAAATAG AGAACAGCAG TAAGATATTT TCTAATTGAA    1440
AATTATCTTA CTGCTGTTTT TTTAGGGATT TATGTCCCAG CCTGTTTTAT TTTCGACTAG    1500
TTTGGAGAAT TTATTGACAT TCACATTATT TAAACGGCAA CAAAGATTGT TTTATTTTGA    1560
TAGGCATTAT ATGGTGTTAA AAAATTTGCA TGAAAATTAA AAAATGCTTC GTTCAGGAAG    1620
GTGTCGTAAT TTACCTATTT GCTGAATGAA GCATTTATT  TTTAAATATG ATAGCCAATA    1680
TAACAAGCTA TAAATCCAAT GATGAATTGT AAAAGTGAAT AATTGAGAAA AAGGTTAATA    1740
TCAAATTTTG GTGTCATCAT TAATGTAAGT TCCTTGGCTA ACGTTGAGAA AGTTGTTAAG    1800
CCACCTAAAA AAACCGGTGA CAAAGAACGC AGGGAACCAT GAGATTGAAA TTGATAGGCC    1860
TATAGTTAAT CCAATTAAAA AACTACCAAC TAGATTTACT ATCAATGTTG CGATAGGTAA    1920
CTTTGAAGTA AATTTATGAT TAAAATAATC AGTAATGGCA CTTCTAGCAA TTGCGCCAAA    1980
ACCGCCGCCA ATCATGACTA AAATGATTGA TATCATGATA AACCACCACC TAGTTTTATA    2040
CCGACGTAAC ATAACAAAAT ACCAAAGACA TAACTTGTTA CAGCATATAG TAGTAAAGTT    2100
ATAAATTGTT GATGATCAAA CATATGTATT AATTCTAATT GAAATGTTGA AAAAGTCGTT    2160
AAAGCACCAA GAAAACCAGT CGTAATAGCT TTTTTAGGG  TCGGATGGTT TGAAAAAAAT    2220
GCAATTGTTA AGGCTGTTAG CAATCCCATT ACAAAGGCAC CAGTCAAATT GGCTATCAGT    2280
GTTCCGATTG GAAAACCTCC GTCAGTATTC AGAAAGAAA  TGAGGTAACG TAATAAAGCG    2340
CCTAAAGCAC CACCGATAAA AATATATACA TATTGCATTT GGTTCACCTC GAAAAGAAGT    2400
AGTTTGAATT TAAAAAAGAG GTTTTGGCAA CACGACGACA AAAATTGTCG ATGCATTATC    2460
AAACCTCATT ATATGTTATA TCTTGTTGTA TAACTATAGC GATTAGATGC ATAGTTATGA    2520
TTTCGAAAAT CTAATATTTT TTATACGCAA CAACGTCATC AAATTGTTTT ACTCATTATA    2580
GCATGATACA TTGTATTGTT TTGTATTAAC GCTACATTGA CATTTTATCT TTTTTAAATA    2640
AAACCGAATG TACGACAATT GAAAAGATAT GTACTAAAAT AACAATTAGA ATAATCCAAG    2700
GCAAACTTTT ACTCGCAATT CTAATCCAAT CTGCATCAGG CTTTAGTGAT TTAATTGAAC    2760
GATCTGCAAA AATTATAGAC AAAAATTAGTA CAATTGAGTT AATAACACTG CAGAAAAGTA   2820
```

| | | | | | |
|---|---|---|---|---|---|
| TTAATTTAAT | AAAAGAATTA | AAAAATCCAC | TTAGGAAAAC | GTTATTTGTA | TTAAAGAAAA | 2880
| AGCTT | | | | | 2885

( 2 ) INFORMATION FOR SEQ ID NO:5:

( i ) SEQUENCE CHARACTERISTICS:
        ( A ) LENGTH: 2362 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Staphylococcus epidermidis
        ( B ) STRAIN: Clinical Isolate SE- 3

( x i ) SEQUENCE DESCRIPTION: SEQ ID NO:5:

| | | | | | |
|---|---|---|---|---|---|
| AAGCTTCACA | ACTTGAAAAT | ATAGCACAAA | CATTAAAGGA | TTTAGGTAGA | AAACGAGCAA | 60
| TTTTAATTCA | TGGTGCAAAT | GGGATGGATG | AGGCCACGCT | TTCTGGTGAA | AATATCATTT | 120
| ATGAAGTTAG | CAGCGAAAGA | GCATTAAAAA | AATATAGTTT | AAAAGCAGAA | GAAGTCGGTT | 180
| TAGCTTATGC | AAATAATGAC | ACGTTGATAG | GTGGTTCACC | TCAAACAAAT | AAACAAATTG | 240
| CATTGAATAT | CCTAAGTGGC | ACGGATCACT | CAAGTAAACG | AGATGTAGTT | TTGTTAAATG | 300
| CTGGAATTGC | TTTATATGTT | GCTGAGCAAG | TGGAAAGTAT | CAAACATGGC | GTAGAGAGAG | 360
| CGAAATATCT | CATTGATACA | GGTATGGCAA | TGAAACAATA | TTTAAAAATG | GGAGGTTAAG | 420
| TAATGACTAT | TTTAAATGAA | ATTATTGAGT | ATAAAAAAC | TTTGCTTGAG | CGTAAATACT | 480
| ATGATAAAAA | ACTTGAAATT | TTACAAGATA | ACGGAAATGT | TAAGAGGAGA | AAGCTGATTG | 540
| ATTCACTTTA | ACTATGATAG | AACATTATCA | GTTATTGCTG | AAATAAAATC | GAAAAGCCCA | 600
| TCTGTACCTC | AATTACCGCA | ACGTGATCTT | GTTCAACAAG | TTAAAGATTA | TCAAAAATAT | 660
| GGTGCTAATG | CTATTTCAAT | ATTAACTGAT | GAAAATACT | TTGGCGGTAG | TTTTGAACGA | 720
| TTAAATCAGT | TATCAAAGAT | AACATCGTTA | CCAGTTTTAT | GTAAAGATTT | TATTATTGAT | 780
| AAAATTCAAA | TAGATGTTGC | AAAACGAGCT | GGTGCATCTA | TTATTTTATT | AATAGTAAAT | 840
| ATTTTAAGTG | ATGACCAATT | AAAAGAATTG | TATTCATATG | CAACAAACCA | TAATTTAGAA | 900
| GCTCTAGTAG | AAGTTCATAC | AATTAGAGAA | CTTGAACGTG | CACACCAAAT | TAACCCTAAA | 960
| ATTATTGGTG | TTAATAATCG | TGATTTAAAA | CGATTGAAA | CCGATGTTCT | ACATACAAAT | 1020
| AAATTACTTA | AGTTTAAAAA | GTCTAATTGC | TGCTACATTT | CAGAGAGTGG | CATTCATACA | 1080
| AAAGAAGATG | TTGAGAAAAT | AGTAGATTCA | AGTATTGACG | GTTTACTTGT | AGGGGAGGCA | 1140
| TTAATGAAAA | CAAATGACTT | AAGTCAGTTT | TTTGCCTAGT | TTAAAGTTAA | AGAAGAATCT | 1200
| CTATGATAGT | TAAATTTTGT | GGTTTTAAAA | CCGAAAGTGA | TATTAAGAAA | ATTAAAAAAT | 1260
| TAGAAGTTGA | TGCAGTAGGG | TTTATACATT | ATCCCGATAG | TAAGAGACAT | GTCTCACTGA | 1320
| AACAATTAAA | ATATTTGGCT | AAAATAGTGC | CAGATCATAT | AGAGAAAGTA | GTGTCGTAGT | 1380
| AAATCCTCAA | ATGTCCACCA | TAAAGAGAAT | AATTAATCAA | ACTGATATTA | ACACAATCCA | 1440
| ATTACATGGA | AATGAAAGCA | TTCAATTAAT | TAGAAATATT | AAGAAACTTA | ATTCAAAAAT | 1500
| AAGAATCATA | AAAGCAATTC | CAGCAACAAG | AAATTTAAAT | AATAACATTC | AAAAGTATAA | 1560
| AGATGAGATA | GACTATGTTT | ATTATAGATA | CACCATCAAT | CACATACGGA | GGGACAGGTC | 1620
| AAAGTTTTGA | CTGGAAATTA | TTAAAAAAAA | TAAAGGCGTT | GATTTTCTCA | TTGCGGTGGT | 1680
| TTGGATTTTG | AAAAGATAAA | ACGATTAGAA | ATATATTCAT | TTGGACAATG | TGGTTATGAC | 1740

| | | | | | | |
|---|---|---|---|---|---|---|
|ATCTCAACTG|GCATTGAGTC|ACATAATGAA|AAAGATTTTA|ATAAGATGAC|TCGAATATTA|1800|
|AAATTTTTGA|AAGGAGACGA|ATGATTAATG|AAAATTCAAA|CAGAAGTAGA|TGAATTGGGC|1860|
|TTTTTCGGTG|AATATGGTGG|CCAATATGTA|CCTGAAACAT|TGATGCCAGC|TATTATTGAA|1920|
|CTTAAAAAAG|CATATGAGGA|CGCGAAATCA|GATACTCACT|TCAAGAAAGA|ATTTAATTAT|1980|
|TATTTAAGTG|AATATGTTGG|TAGAGAAACG|CCTTTAACAT|TTGCTGAATC|ATACACAAAA|2040|
|TTGTTAGGTG|GTGCCAAAAT|ATATCTTAAA|AGAGAAGACT|TAAATCACAC|TGGTGCTCAT|2100|
|AAAATTAATA|ACGCGATAGG|ACAGGCACTA|TTAGCTAAAA|GGATGGGGAA|AACTAAATTA|2160|
|GTAGCCGAAA|CAGGTGCTGG|TCAACATGGT|GTAGCAAGTG|CCACCATCGC|TGCTTTATTC|2220|
|GATATGGATC|TTATTGTTTT|CATGGGAAGT|GAAGATATCA|AACGTCAACA|ACTTAACGTA|2280|
|TTTAGAATGG|AATTGCTAGG|AGCTAAAGTA|GTGTCTGTGT|CAGATGGGCA|AGGAACACTA|2340|
|TCAGATGCTG|TAAATAAAGC|TT| | | |2362|

(2) INFORMATION FOR SEQ ID NO:6:

(i) SEQUENCE CHARACTERISTICS:
        (A) LENGTH: 8654 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Staphylococcus epidermidis
        (B) STRAIN: Clinical Isolate SE-22

(xi) SEQUENCE DESCRIPTION: SEQ ID NO:6:

| | | | | | | |
|---|---|---|---|---|---|---|
|AAGCTTGTTT|TATTGCTTAG|TTATATTTCC|AATAACACTC|ATTTTATATG|TACGTATTGC|60|
|CAAAAAAAT|TATCTATACA|GTAATAAGTA|TGAAATGAGA|ACTGGAATAA|TCATTGGTAT|120|
|TATTGCTTTA|ATTCTAGTAA|TTATGCAAGG|GTTTCACTTT|AACTGGGCTA|TTATTCCTAT|180|
|TTCTATCTAT|GGTCATCAGT|TTGTATTTTT|CGCTGGAATT|ATTTTAAGTC|TTGTTGGTAT|240|
|ATTCTTTAAA|CGTATAGAAT|TTGTAGGAGT|TGGCTTACTA|TTTTGTCAAA|AACATAGATG|300|
|CAATGGTAAC|TGACCCGGAA|ATTGCACAGT|TTTTCTCTTT|AGCAATTTGG|ATTATACTTG|360|
|TTGTGCTAAT|CATTTTTTAT|ACGATACGTT|TATCTGAACG|CACTAAATCA|TCATCATATA|420|
|CAAAGATTTA|AACTCAGAAA|ATATGCTAGA|CATATCTTTC|TGAGTTTTTT|AATTTATTAA|480|
|AATATATCAT|TTGTTTACCA|TATAAGTTTG|TTTTAGAAAA|TGAATCACTA|TTTTAATATA|540|
|CAAATAATTT|AATTACACTG|AAAATAACCT|AAAAGCGTAA|CACTATTTTA|ATATGGGTAT|600|
|ATAAATGACT|AAAGGGAGGT|GCCAAGATGA|ATAAAATTCA|AATTTGTAAT|CAGATTGAAC|660|
|TTAACTATAT|TGATGAAGGC|GAAGGCATCC|CCATCATTTT|AATTCATGGA|TTAGATGGAA|720|
|ACTTGGCAGG|ATTTAAAGAT|TTAAAAAATG|AACTCAAGAA|GCAGTATAGA|GTAATTACTT|780|
|ATGATGTCAG|AGGTCATGGA|AAATCTTCAC|GAACAGAATC|ATATGAATTA|AAAGATCATG|840|
|TTGAAGATTT|AAATGATTTA|ATGGGAGCAT|TAAATATCGA|TTCTGCACAT|ATTTTAGGAC|900|
|ATGATATGGG|GGGCATCATT|GCGAGTGAAT|TTACTGAAAA|ATATCAATAT|AAAGTGATTA|960|
|CATTGACAAT|TGTTTCGGCC|AAAAGTGAAG|ACATTGCAAA|TGGTTTCAAC|AAATTAATGG|1020|
|TTGATTACCA|AGAAGAATTA|GCAGGCTTTA|ATAAATCTGA|GGCAATGATT|ATTTTATTCT|1080|
|CTAAATTATT|TAAAGAGAAA|GATAAAGCAA|TGAAATGGGT|ATCAAAGCCA|AAAATTATAC|1140|
|AATAGACCAA|CTCCGGAAGA|AAGTGCAATT|GCAGTACGTG|CATTGCTTAA|TATTAAAGAT|1200|
|TTAACTCGTG|TTCATCATAA|TGTGTCCATA|CCTACTTTAA|TTGTGAATGG|TAAGTATGAC|1260|

```
CCACTCATAC  AAAATAAAAG  TCATTATGAT  ATGGATCAAT  ATTATGATCA  AGTTACAAAA   1320
ATTGTATTTG  ATAATTCAGG  ACATGCACCA  CATATCGAGG  AACCAGAAAA  ATTCCTGAAA   1380
CTCTACTTAG  ATTTGTTAG   TTAAAAAATA  AGAACATAAA  TAAAACCCT   TAAATGATTA   1440
TTGTCGGAAA  ATCATTTGAG  GGTTTTGTAG  TAGCAGTAAA  GTTTGGACTC  AGATCACTAT   1500
CGTATTAACT  TAATAAAAGA  GTAAAACAGT  CTTATCTTTC  ATAAGTGAAA  GAAATATCTG   1560
TTTNACTCCC  TAGCCATTAT  ACTTCATTTC  ATTATTTGCT  TCTGTGATAC  GGTTGTTTAC   1620
TCGTTTAAGT  AAATCATCGA  TTTTTTTACG  CTGCTTAGAA  TCTACTAAGA  TTAAAACAGT   1680
TCTTTCATCG  TGTTCATTAC  GTTTTTTATT  AAAGTAATTT  TCTTGAGATA  AATTTTTAAC   1740
AGCTTTAACA  ACTTGAGGTT  GTTTATAATT  TAAGTGATTG  ATAATATCTT  TAAGATAATA   1800
TTCCTCTTCT  TTATTCTCAC  TAATATAAGT  TAATACTGCA  AATTCTTCAA  AGCTGATTGA   1860
GAATTCTTTT  TTAATTATTC  CTTTTAATCT  GTCAGCATAA  GTGACCATAG  CTAATAATTC   1920
AAAGCAGTCA  TTGATTTTTG  AAATAGCCAT  TAATGAAACC  TCCCTATTTA  TATCATATCC   1980
ATAAATCTTA  AAACCCATCT  TTTTAAATTT  AAGATAGTT   AATTATATTA  TTGAATTAAG   2040
ATTACTTGGA  TACTATACCC  TAATTTATTA  ATTTATATCT  ATTTTTCTTA  TGAAAATACG   2100
AAAGTGTCCG  TCATAATATA  GTATTAATTT  AAATTTAAAG  AATATATTTA  ATGCTATATT   2160
ATTTAGTTAA  TTATAACTAA  ATAAAATTAA  GAAGTAAACA  AATAAGTGTT  TATAAAACAA   2220
ATTATCTTTT  AAAGTTTATA  CTTGAATTAG  CAATGTAGCA  TTTGCTATAT  TCAAAAAAT    2280
AAGATTGTTT  CTAATTTTCC  TTAATTTAAT  AAAAATTATA  CTAAAAGAA   TACTTTTTGG   2340
AAAGAATTTT  ACTAACATTT  TTTATATATA  AATGTTTATT  AATTTAGAAG  TAGGATTTTT   2400
AACAACTTTT  TCATCTATCA  ATAAGCCTTT  AGTTATATTA  ATATACCCAC  TTTTTAAACT   2460
CTTTTTGTAT  GTTACTTCTC  TTTTTGTAGA  ATTAAAACAT  AGCGTTTTG   AACAATAGCT   2520
GACGTAGGTA  ACTCTATGTC  ATTTGAGGCT  AATTTGATTT  TAAAGTGTGT  TCCAATTTGA   2580
TGATTGGGTT  GTGTAGAAAG  TAAAATGTCG  TAATATGAGA  CGCCATTTTT  TATTTTTGAT   2640
GGTATATTCG  AAATTTCTTT  AATTTTACTA  GTAAATTGAG  TGTTGTCACT  AGATGTTACA   2700
GAAATATTTT  GATTTATTTT  TAATAAATTC  AACTCAGATT  CTGATATATT  AGCACGAATA   2760
ATACGTTCGT  TGCTATTAAT  TTGCACTATC  TTTTCGTTTG  GTTTTGAAGG  GATAGAATTA   2820
ATATATGAAA  TACTTCCATT  AATTGGTGAA  ATAAAGTGG   ATTTAATTGA  GGATTTAGTT   2880
TGAATCATTT  GTAATTTTAG  CTGATTAAGG  AATGAATAAT  AATGTAAATC  ATTTTTAGAA   2940
TTTAAAGTTT  TGTTGTTACG  TTCATTACTA  AGTGTATTTT  GGAGTTCCTC  ATATAAATGA   3000
TCTTTTTCAT  AATTGTAATA  TTCTAACACT  GGAGTGTTTT  TAGATACTTT  GCTATGATTT   3060
TTTACTAAAA  GTTTTTGGAG  TTGTCCTAAA  GTGGGAGTGT  AGTAGAAAAT  ATAGCTGTTA   3120
AGAGGGCTT   GTATACCAGT  TGTTGAAAGG  AGTAATTTGG  GCTTTGCTTT  TATAGTTTTT   3180
ATATTTTTAA  TATCTTCTGT  TTTAGAAGTT  AATTTAGAGA  AAGTAATGTA  ACTAAAACTA   3240
CAAGTTGTGA  GAATGAAAAT  GAATAGTAAT  GAAGAAATAA  CGATGCGTTG  CTTGGTCATG   3300
GATGTTCACC  TCATAATATT  ATTGTGAGGT  TATTATACAC  TATTATTTTA  AATGAAATAT   3360
ATTAATTTTA  AATAAGCATT  ACTTTTGGTT  TGTATATTGT  TTTATTTCAA  AAAATAAAGT   3420
AAATCAATTT  AATAAATTGA  AAAATAGAAG  GCTATCTTTA  ATTTTAAAAT  ATATGATTCT   3480
ACATAAATGT  TACTATAAGA  AGAATCACTC  ATAAAAACTG  CCAACAAAGA  CAAAATCTTT   3540
GTTGGCAGTT  CGAAATAGAC  ATTTATTTGT  ATGAGGAATC  TACATTAATA  TAAGCGGATA   3600
ATTTTTATTC  AGAATAAGGA  ATTTAAAAATA ATCGTAATAA  AATAATACCT  ATAGCTATAC   3660
```

| | | | | | |
|---|---|---|---|---|---|
|ATAATAATCC|ACCTAACTTA|CGTGATGTTA|TTTTGTTTTT|AGGTGAACCC|AACAAACCGA 3720|
|AATGATCGAT|AATAATACCC|ATAATCATTT|GGCCCATCAT|AGCAATTATA|GTAGTTAAAG 3780|
|CTGCTCCTAA|GAAAGGCATT|AAAATAATAT|TAGATGTTAC|GAATGCCATT|CCTAGTATCC 3840|
|CTCCAATAAA|ATAAATAGAT|TTAATCTTAC|CTAGTGTTTT|ATGAGTAGAT|GATATTTTCA 3900|
|GACTACGATT|AAATACTAAT|GTTAATATAA|ATAACGCTAT|TGTACCAACG|CTAAATGATA 3960|
|TGAGTGAAGC|AAATATGGAT|GAGTGTGTGT|GTTGAGCCAG|TGTGCTGTTG|ATTGTTGTTT 4020|
|GGATTGGCGG|ACGAAACCAA|ATACGAATCC|AATAAGCAAC|CAGAATACTA|TTGGTGTATT 4080|
|CTTATGTCTA|TTAACAGGAT|GTCTACGAAC|ATAATTCATA|AATATAATTC|CAGTAATTAA 4140|
|AAATATAATT|CCAACACCTT|TAAATAATGT|AAAAGATTGT|TGATGGGCGC|CCAATAATCC 4200|
|AAATGTATCA|ATGATTACAC|CCATAATAAT|TTGCCCTGTA|ACCGTAATAA|CAACAGTAAG 4260|
|TGCTGCGCCT|AATCTTGGTA|ATAATAATAA|GTTCCAGTT|AAATAGATAA|CACCTAATAG 4320|
|TCCTCCTAGG|ACCCAAGTAT|AGTTAAGTGT|TTGCTTAGAA|AAGAATTCTG|GTGTTAATAC 4380|
|TTGTGGATGA|ATAATGATAT|TAAGCACAAG|TAAGCATATT|GTTCCGACAG|CAAAAGATAT 4440|
|GGTTGAAGCA|TAAAAGATG|AACGGGTAAA|TTGGCTTAGC|CTTGAGTTGA|TTGAAGTTTG 4500|
|AATAGGAAGT|AACATGCCAA|CAAAAATTCC|TAAAAGATAT|AGAAAAAACA|ATGATAAAAA 4560|
|CCAACTTTCT|CAATTTAATA|TGATTATCAT|ACCATTCATA|ATCATGTTTC|TAAAATGATT 4620|
|GAGCCATAAG|CAAAGTATAG|AAATAAGTTG|TGAATGTTCC|GAGGTGTCAT|ACAGCCGATA 4680|
|CTATTTTGAT|GAATCATTAT|AATAAAATGC|ACATTAAACA|AGTTTTAGAA|TTAAAAAAG 4740|
|CGAGACATCA|TTTTGAATTT|GATATCTCAC|TTCATATTAA|TAAAAGAACA|ATGTAAATTA 4800|
|AGTTCTTTTT|TAGACTTGAA|CAATTTTAAA|AAATTTGTTC|TTCGATAAGT|CTTTTTTATG 4860|
|ATTTTAGTAC|TTTAAATAAA|GCGTCAAAAA|TAATGTTTTA|TGAATTAATT|TTTATCTTCA 4920|
|AATATAACAG|TTGTCCTTTT|ATCAATAAGT|TGTGCAGCAT|AAATTTTGAC|AGGCTTTCCC 4980|
|AAACTAAATC|TTAAAATGTC|TAATTCTAAA|ATGTCTAATT|CTAAAGTTG|GTTCATACTT 5040|
|TCTTTAATTA|ATTGTTCTGT|AGTAATAGCG|TTAAAATCGG|GTAATAGTAA|TTTGACGGGT 5100|
|TTATTAAGAT|TTGATTTAAA|TACGAGTTCC|AAAGTTTTTG|ACATACTGAT|GTATCCTCCT 5160|
|TAAATTAAAG|ATTCTGTTTT|AACGATCTCG|ACTTTGTCAT|ACTCTTCGCC|ACTGAACGTT 5220|
|CAATGATGGA|ACGAAAAGAT|TTGATTTGAT|CATTAGAAAC|AAGCGGATTA|ATGTTAGAAA 5280|
|AACGACGCTT|ATGTTCGACT|ACTTTACCTT|CAGAATTATG|TTTGATTTGA|GTAAAGATAA 5340|
|TCGTCACTTG|ATTGACTTCA|TTCATAATAA|AACCTCCTTT|CACTATATAT|ATCGAAATAG 5400|
|ATTGAAAAAA|AAGGACACAT|TTTTTGAAAA|ATATAGGCAA|ATGCCTTTGA|TGTGATACAA 5460|
|ACGTCATTTA|TCATTAATTA|TGAAACCTGT|TTTAGAAGGT|ATATGAGGTA|AGTAGAATTG 5520|
|TTAAGTTGTA|AAAGAAAAA|TTGGAACCTG|ATATTTAAAA|TAACCAACTT|AAAAGATTGA 5580|
|TCAGTGTCTA|AAATTACTAT|TTATATATGA|ATTAAAATAT|TAAGATCTCC|CAATATGAGA 5640|
|ATGAATTAGT|TTAAGTTTAT|CGATGATTGA|AAAATTATAG|CCTCATGGAT|TCTATCTTAT 5700|
|ATAAAATAAA|GTTCTATTCC|CTTTTGGATA|TAAATAAGAA|TAGTTACCTT|TTTGTGATAT 5760|
|GCCAATTCAG|AAAAAAAGCG|ACAGTGCTTG|AATCTATGTA|TGCTCAATAA|ACTCATTCAA 5820|
|ATCAACTAGC|AATATCAAAT|CATAAATCGT|GTTGCACCAT|AATAAGGATT|AAAACCTGTT 5880|
|AGTTAACTA|ATTTAAGAAA|AACATTTGAT|TATCTTCTCT|TTCAATCGGG|AATATTAATT 5940|
|TCTATCATTC|AACAATATTT|TGGATATCAG|ATAACTTAAG|AAATATTGAG|ATTTATTGAA 6000|
|ATACGATATG|TTTCAAATCG|CCATACAATG|ATTACACTTA|ATAAATGATT|ACACTTAATA 6060|

```
TAAATGTAAA AAGAAAAGGA GGGGTTAAAT GAGTTTAGTA TATCTTATGG CGACTAATTT      6120
ATTAGTCATG CTCATAGTTT TATTCACTCT GAGTCATCGT CAACTAAGAA AGGTTGCGGG      6180
CTATGTTGCA TTAATAGCTC CTATTGTGAC ATCTACATAT TTTATTATGA AAATACCAGA      6240
TGTGATTCGA AATAAGTTTA TTGCTGTTCG ATTACCATGG ATGCCTTCAA TTGATATTAA      6300
TTTAGATTTA AGATTAGATG GTTTAAGTTT AATGTTCGGC TTAATTATTT CGCTAATAGG      6360
TGTGGGTGTA TTTTTTTATG CTACGCAATA TTTATCCCAC AGTACGGACA ATCTTCCTAG      6420
ATTTTTCATC TATTTACTAT TATTTATGTT CAGTATGATT GGCATTGTAA TAGCTAATAA      6480
TACCATCTTA ATGTATGTAT TTTGGGAACT CACAAGTATT TCCTCATTCT TGCTTATATC      6540
CTATTGGTAC AATAATGGTG AAAGTCAATT AGGCGCCATT CAATCTTTCA TGATTACAGT      6600
GTTTGGTGGG CTAGCGTTAT TAACAGGATT TATCATTTTA TATATCATTA CAGGAACAAA      6660
CACAATTACT GATATCTTAA TCAACGCAAT GCAATTTCAC GACATCCTTT ATTTATACCA      6720
ATGATTTTGA TGCTATTATT AGGTGCTTTT ACCAAATCTG CACAATTTCC GTTTCATATT      6780
TGGTTACCAA AGGCCATGGC AGCACCTACA CCAGTAAGTG CTTATCTTCA TTCGGCAACA      6840
ATGGTAAAGG CTGGAATCTT TTTACTATTT AGATTTACAC CTTTATTGGG ACTTAGTAAT      6900
GTTTATATTT ATACAGTGAC ATTTGTTGGT CTAATAACTA TGTTATTTGG ATCTTTAACT      6960
GCTTTACGAC AATACGACTT AAAAGGTATA CTCGCTTATT CTACAATAAG TCAATTAGGT      7020
ATGATTATGA CAATGGTAGG TCTAGGTGGC GGTTATGCTC AGCACACATC AGATGAATTG      7080
TCTAAGTTTT ATATTTTAGT TTTATTTGCT GGCTTATTCC ATTAATGAA TCATGCGGTT       7140
TTTAAATGTG CATTATTTAT GGGCGTTGGT ATCATTGATC ACGAGTCCGG AACACGTGAT      7200
ATTCGTTTGC TAAATGGTAT GCGTAAAGTC TCCCCTAAAA TGCATATTGT CATGTTGCTC      7260
GCTGCATTAT CTATGGCAGG TGTTCCTTTT TTAAATGGCT TTTTAAGTAA GGAAATGTTT      7320
TTAGATTCGT TAACTAAAGC AAACGAACTT GATCAATATG GCTTCGTATT AACGTTTGTG      7380
ATTATTTCAA TAGGTGTCAT CGCGAGTATA TTGACTTTTA CTTATGCACT TTACATGATA      7440
AAAGAAACAT TCTGGGGAAA TTACAATATA GAAAAATTTA AACGTAAACA AATACATGAA      7500
CCATGGCTAT TTAGTTTACC AGCTGTGATT TTAATGTTAC TCATTCCAGT TATCTTCTTT      7560
GTTCCAAACG TTTTTGGCAA CTTTGTTATT TTGCCCGCAA CCAGATCTGT ATCTGGGATA      7620
GGGCGGAGGT TGATGCATTT GTGCCACATA TTTCTCAGTG GCATGGTGTG AATCTCCATT      7680
AATTTTAAGA TAGTGTATAT ATTGGACTAT TTTAGCTCTA GTGTGATTGG AAAGAGGTTA      7740
CGCATCAAAT AATCAAAAGT GCTCGATTAC AGTGGCTATC GGAAATTTAT AGAGAATTTG      7800
AATTATACTC AGCCCGTGGT ATACGTGCAT TGATGAATAA TAAATTGAAT TATTACATCA      7860
TGATTACATT ATTTATTTTT GTAGCTATTG TAGTTATGGA TATTTGACTG TGGGTTTTCC      7920
TCATGTACTC AGCTTCATAT TAGTTCTTTC GGACCGTTGG AAGTTATCTT ATCAGTTGTA      7980
ACATTGATTA TCGGCATTTC ATTAATCTTT ATTCGTCAAC GACTAACGAT GGTGGTATTG      8040
AATGGAATGA TTGGATTCGC AGTTACATTA TATTTATTG CAATGAAAGC TCCAGATTTA       8100
GCTTTAACAC AGTTAGTTGT TGAAACTATT ACGACAATCT TATTTATTGT TAGTTTTTCG      8160
AGACTACCTA ACATCCCTCG AGTTAAGGCA AATTTAAAAA AAGAGACCTT CAAAATCATT      8220
GTGTCACTTG TTATGGCATT GACGGTGGTA TCACTTATTT TTGTTGCTCA ACAAGCAGAT      8280
GGTATGCCTT CAATTGCTAA ATTTTATGAA GATGCATATG AACTTACAGG TGGAAAAAAT      8340
ATTGTCAATG CTATACTAGG TGACTTCAGA GCTTTAGATA CTATGTTTGA AGGACTAGTG      8400
TTAATCATAG CTGGATTAGG TATTTATACG TTACTTAATT ACAAAGATAG GAGGGGGCAA      8460
```

| | | | | | |
|---|---|---|---|---|---|
| GATGAAAGAG | AATGATGTAG | TACTTAAATC | AGTTACAAAA | ATTGTAGTGT | TTATTTTGTT | 8520
| AACATTTGGA | TTTTATGTAT | TTTTGCTGG | CCATAATAAT | CCAGGTGGTG | GCTTTATTGG | 8580
| TGGCTTGATT | TTTAGCTCGG | CATTTATCTT | AATGTTTCTT | GCCTTTGATG | TAAATGAAGT | 8640
| GTTGAAAAAA | GCTT | | | | | 8654

( 2 ) INFORMATION FOR SEQ ID NO:7:

( i ) SEQUENCE CHARACTERISTICS:
        ( A ) LENGTH: 5024 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Staphylococcus epidermidis
        ( B ) STRAIN: Clinical Isolate SE- 32

( x i ) SEQUENCE DESCRIPTION: SEQ ID NO:7:

| | | | | | |
|---|---|---|---|---|---|
| AAGCTTTTTG | ATTTTTAAAG | AAAAAATTAA | ACAAGGGGGC | ATTGCTTATG | GTCAATAGAA | 60
| GAAAGATATC | AATTATTGGC | GCGGGACATA | CAGGTGGGAC | TCTAGCATTC | ATTCTTGCAC | 120
| AAAAGGAATT | AGGAGATATT | GTGTTGATTG | AACGCCAGCA | ATCAGAGGGT | ATGGCTAAAG | 180
| GAAAGGCGTT | AGATATTTTA | GAAAGCGGAC | CCATTTGGGG | GTTTGACACA | TCTGTACATG | 240
| GTTCAGTAAA | TATAGAAGAT | ATTAAAGATT | CAGACATAGT | GGTGATGACT | GCAGGTATAC | 300
| CTAGGAAATC | AGGAATGACA | AGGAGAAGAA | TTAGTTCAAA | CTAATGAACA | AATAGTACGA | 360
| GAAACTGCAT | TACAAATTGC | AACGTATGCA | CCTCATTCAA | TAATTATTGT | ATTGACTAAT | 420
| CCGGTTGATG | TTATGACATA | TACTGCATTT | AAAGCATCAG | GTTTTCCTAA | AGAACGTATT | 480
| ATTGGTCAAT | CTGGAATTTT | AGACGCTGCA | AGATATCGAA | CTTTTATTGC | TCAAGAACTT | 540
| AACGTGTCTG | TCAAAGATGT | AAATGGGTTT | GTTTTAGGTG | GACATGGTGA | TACGATGTTA | 600
| CCTTTGATTA | ATAACACACA | CATTAATGGG | ATTCCAGTTA | AGCATCTTAT | TTCTGAAGAA | 660
| AAGATTGATC | AAATTGTTGA | ACGTACACGT | AAGGGTGGTG | CAGAAATTGT | TGCATTACTA | 720
| GGTCAAGGCT | CAGCATATTA | TGCACCAGCA | ACTGCTATAT | ATGAAACTAT | AGATGCAATT | 780
| TTTAATGATC | GGAAACGGTT | ATTACCAAGT | ATTGCTTATC | TAGAGGGAGA | ATACGGTTGT | 840
| TCAGATATTT | GTTTCGGAGT | TCCTACTATA | ATAGGATATC | AAGGAATAGA | AAAGATTATA | 900
| GAGGTAGATA | TGAATAATGA | TGAGTATCAA | CAACTACAAC | ACTCTGCGCA | AGATGTGAGT | 960
| GAAGTCAAAA | ACTCACTAAA | ATTCAAATAA | ATAATTATGA | AGTTCTACAT | CTTAAATTGT | 1020
| TAGATTTTTG | TGAAAATTGT | GTAAAGGGTA | TTTTTTCGTT | GATTTATAAA | AGCGCTTTCT | 1080
| TGATATAATG | AACATATATT | CATAGAATAA | GGAGACGATT | AAAATGGCTA | AAGGGGACCA | 1140
| ATATCAAGCT | CATACTGAAA | AATATCATGA | GTAAAAAGTC | TAAAAAAGT | TATAAACCTG | 1200
| TGTGGATTAT | CATTAGTTTT | ATTATTTAA | TTACAATCTT | GTTATTACCC | ACACCAGCAG | 1260
| GATTACCTGT | AATGGCTAAA | GCAGCACTAG | CTATTTTAGC | TTTCGCTGTA | GTTATGTGGG | 1320
| TTACAGAAGC | AGTTACTTAT | CCAGTTTCTG | CAACATTAAT | TTTAGGATTA | ATGATACTTT | 1380
| TACTAGGTTT | AAGTCCAGTT | CAAGATTTAT | CCGAAAAACT | TGGAAACCTA | AAAGTGGCGA | 1440
| CATAATACTA | AAAGGTAGCG | ATATTTTAGG | AACGAATAAC | GCGCTTAGTC | ACGCTTTTAG | 1500
| TGGTTTTTCA | ACCTCAGCCG | TAGCACTTGT | AGCTGCAGCA | TTATTTTTAG | CAGTAGCTAT | 1560
| GCAGGAAACC | AATTTACATA | AACGACTTGC | ATTATTTGTG | CTATCAATTG | TTGGAAATAA | 1620

-continued

| | | | | | |
|---|---|---|---|---|---|
| AACTAGAAAT | ATAGTCATTG | GTGCTATTTT | AGTATCTATT | GTTCTAGCAT | TCTTTGTACC | 1680
| ATCAGCTACA | GCACGTGCTG | GTGCAGTTGT | CCCAATATTA | CTGGGAATGA | TTGCTGCATT | 1740
| TAATGTGAGT | AAGGATAGTA | GACTTGCTTC | ATTATTAATT | ATTACTGCTG | TACAAGCAGT | 1800
| TTCGATATGG | AATATAGGTA | TTAAAAACGG | CTGCAGCACA | AAATATTGTA | GCCATCAATT | 1860
| TTATTAACCA | AAATTTAGGA | CATGATGTAT | CATGGGGAGA | GTGGTTTTTA | TATCTGCGCC | 1920
| GTGGTCAATC | ATTATGTCTA | TAGCTCTTTA | TTTTATAATG | ATTAAGTTTA | TGCCACCTGA | 1980
| ACATGATGCA | ATTGAAGGTG | GAAAAGAGTT | AATTAAAAAG | GAACTTAATA | AATTAGGACC | 2040
| AGTCAGTCAT | AGAGAATGGC | GACTAATTGT | GATTTCAGTG | CTTTTATATT | CTCTGGTCGA | 2100
| CTGAGAAAGT | ATTGCATCCG | ATTGATTCAG | CTTCGATTAC | ACTAGTTGCT | CTAGGTATTA | 2160
| TGCTAATGCC | AAAGATTGGT | GTTATTACTT | GGAAAGGTGT | TGAAAAGAAG | ATTCCTTGGG | 2220
| GGACGATTAT | AGTATTTGGT | GTAGGAATCT | CACTTGGTAA | TGTATTACTT | AAAACAGGAG | 2280
| CCGCTCATGG | TTAGTGATCA | ACATTTGTTT | GATGGGTCTT | AAACATTTAC | CGATCATAGC | 2340
| AACTATTGCG | TTAATTACCT | TATTTAATAT | ATTAATACAT | TTAGGTTTTG | CAAGTGCAAC | 2400
| GAGCTTAGCC | TCTGCGTTAA | TACCTGTGTT | TATTTCTTTG | ACTTCAACGC | TAAATTTAGG | 2460
| TGATCATGCT | ATTGGTTTTG | TATTAATACA | ACAATTTGTG | ATTAGTTTTG | GTTTCCTACT | 2520
| ACCTGTCAGT | GCACCACAAA | ATATGCTTGC | ATATGGTACT | GGGACTTTTA | CCGTAAAGGA | 2580
| TTTTTTAAAG | ACAGGTATAC | CTTTAACGAT | AGTAGGTTAT | ATTTAGTTA | TCGTATTTAG | 2640
| TTTAACGTAT | TGGAAATGGC | TTGGTTTAGT | GTAAGTAAAA | GATTAGGTA | TAAAATGAT | 2700
| AATTATAAAT | GTCTCGTAAA | GTTTAATATT | TTAACTTTAC | GACACATTTT | TTATAAACTC | 2760
| GTGGCAAGTT | AATCTTAATA | GTTGAAATGT | ATCGTATAAA | AATATATGA | ATGTAAATAG | 2820
| AATTTAGTAT | TAGAGAATAA | CAAAAAATTG | ATGTTAGGTG | GTAAAATCTA | ATGGCTATAG | 2880
| GTGTCATATT | AAATAGAGTT | TTTAGGCTAA | ATAATAATCC | ATTATTGAT | TATATATATA | 2940
| GTAATAAAGA | ATCTATAAAT | CATTGTTATT | TTATTATTCC | AACTGAAGAG | TTTGAAGAAG | 3000
| AAGCAAAAAA | GAAAGCACAA | TACTATTATG | GGTCCATACA | GAAGTTTATG | TATGAACTAC | 3060
| AACGATATGA | TATAGAACCC | TTTTTGATGT | CTTATGATAA | ATTAATAGAC | TTTTGTAAAA | 3120
| AACAAGCTAT | AGACAAGTT | GTTGTTGCAG | GTGATATTAT | GAGTTATCAT | CACGAAGAAT | 3180
| ATGACATTTT | ACATCAAAGG | AAACGATTTA | AACAAGCTAA | TATTCAAGTA | ATATCATTAA | 3240
| GAGCAAATCA | TTATTTTAAC | CCCCGCAAAA | CACATAATAA | ACAAGGGGAA | CCATATAAAG | 3300
| TATTTACCAG | TTTTTATAGA | AAATGGCGTC | CTTACTTAAT | GATTAGAGAT | GAATATGACT | 3360
| ATCATTTAGA | AGATATTTCA | AAGGTTGTAG | TGAAATCTCA | ACATAAAATT | AAAGAAGATT | 3420
| ATCATTCATA | TGGTATAAGT | GAACGTGATG | TTCAAAATCG | TTGGTCTGAA | TTTTTATCTC | 3480
| AAGATATCGA | AAATTATAAA | GAAAACAGGG | AATACTTGCC | TGAAGTATTA | ACAAGCCAAC | 3540
| TAAGTATTTA | CTTAGCTTAT | GGAATGATAG | ATATTATACA | ATGTTTTCAA | CGATTTACTT | 3600
| CAAAATTATG | ATAAAAATGA | ACAAAATTAC | GAAACTTTTA | TACGTGAATT | GATTTTTAGA | 3660
| GAGTTTTATT | ATGTATTAAT | GACCAATTAT | CCCGAAACAG | CTCATGTTGC | TTTTAAAGAA | 3720
| AAATACCAAC | AATTGAAATG | GTCTTATAAT | GAAGAGAATT | TTAAACTGTG | GAAAGATGGG | 3780
| AATACTGGTT | TTCCAATTAT | TGATGCAGCA | ATGGAGGAAC | TTAAACAAC | TGGATTTATG | 3840
| CATAATCGCA | TGAGAATGGT | AGTTTCTCAA | TTTTTAACTA | AAGATTTGTT | TATTGACTGG | 3900
| ATTTGGGGTG | AGTCATTTTT | CAAACAAAAA | TTAATAGATT | ATGATGCAGC | TTCAAATGTT | 3960
| CACGGATGGC | AGTGGTCAGC | TTCTACTGGA | ACAGATGCTG | TACCATACTT | TAGAATGTTT | 4020

| | | | | | |
|---|---|---|---|---|---|
| AATCCTATAA | GACAAAGCGA | GCGTTTTGAT | AATAATGCAC | GATATATAAA | AACTTACATT | 4080
| CCAAGATTAA | ATCAGGTAGA | TGCTAAGTAT | TTACACGATA | CTCATAAATT | CGAGCAACAA | 4140
| ATAAGGGGC | AAGGTGTTGA | AATAGGTAAA | GACTATCCTA | AACAAATGAT | TGATCACAAA | 4200
| GAAAGTAGAC | AACGTGTAAT | GTCAGAATTC | AAAGCTATAG | ATTAAATAAA | AAAGATCTGA | 4260
| ACAACATGAT | ATAGGTGTTC | AGATCTTTAT | CTAGTTACAT | AAAAAAGCAA | ACATGAATTA | 4320
| AAATATATTC | TAACAAAGTT | AAAATATACA | TATATTTAAG | ATTTAATTTA | GTTTTCAAAG | 4380
| GTACTTCCCA | ATTTGTATAA | CGGGGCTCAT | AATAAAATAA | TTGCATCAAA | TATAATCCTA | 4440
| TCCCTAACGG | TAAACACATT | AATAAAATAG | CTTTAGTATA | ACTCCATCCT | ATTTGATGCC | 4500
| ATAAATGACC | TATCATAAGT | TGAATAATGA | TGAGACATAC | CATTAAAATT | ACTTCAATTA | 4560
| TCATTGGTAT | AATCTCACCC | CTTTAATAAA | CAATATGACT | GTTGCTTGTA | TGAGCACCAT | 4620
| TAAAACGACA | AATAGTAACG | CTTTAACATC | TATGATTAAA | AAACCTCTT | TCACAATTTT | 4680
| TAAAGGTGCA | TTTAATAAAT | AGACAGTATG | TAATCTTAAG | AATCGACCGA | TGTAAATACC | 4740
| TAATCCATTT | AAGAACATTA | ATATAACTAT | CAATAGTCGA | TTTAACCATA | CATAAGACGT | 4800
| AAAATGTGCA | ATTTCTAAAA | ATATAAGAAT | TGTGAGGTAT | ATTGCTAAGA | GTACGCCAAG | 4860
| TATTAAATAG | GTGAAATAAA | TCCATTCTGT | GATGTTTAAT | CCAGCTAAAA | AGTTAAATTG | 4920
| AAATTGGTTT | AAGTGTATGA | GATCGGTAAT | CATATAAAAT | GTGTTTGGAA | CTAATAATAG | 4980
| AAATATGAGT | CCGAAAACAA | TAAATAAGGG | CCATTCAAAA | GCTT | | 5024

( 2 ) INFORMATION FOR SEQ ID NO:8:

( i ) SEQUENCE CHARACTERISTICS:
        ( A ) LENGTH: 3287 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Staphylococcus epidermidis
        ( B ) STRAIN: Clinical Isolate SE- 37

( x i ) SEQUENCE DESCRIPTION: SEQ ID NO:8:

| | | | | | |
|---|---|---|---|---|---|
| AAGCTTGCCT | ATTGATTTTA | AAAAATTAAT | GATTATAGGT | TCACTCATAT | CTGTTGCAAC | 60
| TGCATCAGTG | CCTATGTTTT | TTGGGAAGCC | ATTTTTATAT | CAAACTGAAG | CAAATGTAAC | 120
| ATTTCCATTA | CTAGGACATG | TTCATGTTAC | TACTGTGACT | TTATTTGAGC | TTGGCATCTT | 180
| ATTAACAGTA | GTAGGTGTGA | TTGTTACAGT | TATGCTATCT | ATAAGTGGGG | GTAGATCATG | 240
| AATTTAATAT | TACTCCTTGT | GATAGGATTT | TTAGTGTTTA | TTGGAACTTA | TATGATTTTA | 300
| TCTATTAATT | TAATTCGTAT | TGTTATTGGT | ATTTCTATTT | ATACACACGC | CGGTAATTTA | 360
| ATTATTATGA | GTATGGGGAA | ATATGGACCT | CATATGTCTG | AACCGCTAAT | TCAAGGTCAT | 420
| GCTCAAAACT | TTTGTTGATC | CTTTATTACA | AGCTATCGTT | TTAACAGCTA | TTGTGATTGG | 480
| ATTTGGTATG | ACTGCGTTTT | TATTGGTGTT | AATATATAGA | ACTTACAGAG | TAACTAAAGA | 540
| GGATGAAATA | AGTGCATTGA | AAGGTGATGA | AGATGATGAG | TAATTTAATA | ATATTGCCTA | 600
| TGTTGTTGCC | TTTTGTATGT | GCTTTAATTT | TAGTCTTCAC | TAAAAATAAA | AATCGTATTT | 660
| CGAAAATCCT | ATCCATTACA | ACTATGATTG | TTAATACAAT | GATTTCAATT | GCTTTACTTA | 720
| TTTATGTCGT | TAATCATAAA | CCGATAACAC | TTGATTTTTG | GGGGGATGGA | AAGCACCTTT | 780
| CGGCATTCAA | TTTCTAGGTG | ATTCACTGAG | TCTGCTTATG | GTGTCAGTAT | CATCTTTTGT | 840
| TGTTACGCTA | ATAATGGCAT | ACGGCTTTGG | TAGAGGGGAG | AAGCGAGTCA | ATCGATTCAC | 900

```
CTCCTACATT ATCTTTATTA ACAGTAGGTG TTATTGGTTC GTTTTTAACT TCTGATTTAT      960
TTAACCTATA CGTGATGTTT GAAATTATGC TTCTTGCTTC GTTTGTACTT GTTACATTAG     1020
GACAATCTGT TGAACAATTA CGTGCAGCGA TAGTATATGT TGTTCTGAAT ATTTTAGGTT     1080
CGTGGTTGCT TTTATTAGGA ATTGGCATGT TATATAAGAC AGTCGGAACA CTTAATTTCT     1140
CACATTTAGC GATGCGATTG AATCATATGG AAAATAACCA AACAATAACG ATGATATCTT     1200
TAGTATTTCT AGTTGCTTTT AGTTCAAAGG CAGCACTAGT GATTTTCATG TGGTTACCTA     1260
AAGCATATGC AGTGCTTAAT ACGGAACTTG CCGCGTTATT TGCAGCATTG ATGACAAAAG     1320
TTGGAGCTTA TRCGCTTATT CGTTTTTTTA CTTTACTATT CGACCATCAT CCAAGCGTCA     1380
CGCATACATT GCTCGTGTTT ATGGCTTGTA TCACAATGAT TATCGGTGCA TTTGGTGTCA     1440
TCGCTTACAA AGATATTAAG AAAATTGCGG CTTATCAAGT TATTTTGTCT ATTGGATTCA     1500
TTATTTAGG TTTAGGTTCT CATACTATAT CAGGTGTAAA TGGTGCTATC TTCTATTTAG     1560
CGAATGATAT TATCGTTAAG ACATTATTGT TTTTGTAAT TGGTAGTCTT GTTTATATGT     1620
CAGGCTATCG AAATTATCAG TATTTAAGTG GACTGGCAAA AGAGAACCAT TCTTTGGTGT     1680
TGCATTTGTC GTGGTAATTT TTGCTATAGG TGGCGTACCT CCTTTTAGTG GCTTTCCGGG     1740
TAAAGTCTTA ATATTCCAAG GGGCTATTAC AAATGGTAAT TATATTGGTT TAGCACTTAT     1800
GATTGTGACA AGTTTAATTG CTATGTATAG TCTTTTTAGA GTGATGTTTA TAATGTATTT     1860
TGGTGATGCT GACGGAGAAC AAGTACAATT TAGACCACTA CCTATTTATC GTAAAGGTTT     1920
ACTTAGTGTT TTAGTTGTAG TGGTATTAGC GATGGGTATT GCAGCCCCTG TTGTTCTGAA     1980
AGTAACAGAG GATGCAACAA ATCTTAATAT GAAAGAAGAT GTCTTTCAAA AGAATGTAAA     2040
TACACATTTG AAGGAGGTTA ATCATAAGTG AAGCAAGTTG TATTAAATAT TGTTATCGCG     2100
TTCCTTTGGG TACCCTTTCA AGATGAAGAT GAATTTAAAT TTACAACCTT CTTTGCTGGA     2160
TTTTTAATTG GTTTAATTGT GATTTATATT CTGCATCGCT TTTTTGGTGA AGAATTTTAT     2220
TTGAAAAAGA TATGGGTGGC TATTAAATTT TTAGCTGTAT ACCTATACCA GCTTATTACT     2280
TCTAGTATAA GTACCATAAA TTACATCTTA TTTAAGACGA ATGAAGTTAA TCCAGGTTTA     2340
CTCACATATG AAACTTCATT AAAAAGTAAT TGGGCTATTA CTTTTTTAAC GATTTTAATT     2400
ATTATTACTC CAGGATCGAC AGTTATTCGA ATTTCTAAAA ATACTAATAA ATTTTTTATT     2460
CACAGTATTG ATGTGTCAGA AAAAGATAAA GAAAATCTTC TAAAAGTAT TAAGCAGTAT      2520
GAGGATTTAA TTTTGGAGGT GACACGATGA TTGAAATGTT CACTCAAATA TTTATTATAA     2580
GTGCATTAGT GATTTTTGGT ATGGCACTAC TTGTTTGTCT AGTCAGATTA ATTAAAGGTC     2640
CCACTACTGC TGATAGAGTT GTATCATTTG ATGCCTCGAG TGCTGTTGTT ATGTCTATTG     2700
TTGGTGTGAT GAGCGTTATT TTTAACTCAG TGTCTTAATG TTAATTGCAA TTATTTCGTT     2760
TGTCAGTTCG GTCTCAATTT CAAGATTCAT CGGGGAAGGA CGTGTCTTCA ATGGAAATCA     2820
TAAAAGACAT CGTTAGTCTT ATTGCTTCGA TACTTATTTT CTTAGGAAGT ATTATTGCAT     2880
TAATTAGTGC AATAGGGATT GTAAAATTTC AAGATGTCTT TCTAAGAAGT CACGCCTCAA     2940
CGAAAAGTTC TACATTGTCA GTATTACTAA CTGTAGTTGG TGTACTGATC TATTTTATTG     3000
TGAATTCAGG TTTTTTCAGT GTCAGATTAT TATTATCACT AGTTTTATC AATCTTACAT      3060
CTCCGGTTGG AATGCATTTG ATAAGTAGAG CGGCCTACCG TAATGGTGCA TATATGTACA     3120
GGAAAGACGA TGCATCTAGA CAATCTACTA TCTTATTAAG CCAAAAAGAG TTTAATACGC     3180
CAGAAGAATT AAAAAAACGT GCAAAACTAC GAGAAGAAAG ACGAGAAAAA TTATACTATA     3240
AAGAAAAAGA ATATATTAAT AAAATGGACG ATTGATTGTT TAAGCTT                   3287
```

( 2 ) INFORMATION FOR SEQ ID NO:9:

( i ) SEQUENCE CHARACTERISTICS:
        ( A ) LENGTH: 2291 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Staphylococcus faecalis
        ( B ) STRAIN: Clinical Isolate S2- 1

( x i ) SEQUENCE DESCRIPTION: SEQ ID NO:9:

```
AAGCTTTAGA  TAATGATAAA  CGCGTGTATG  TGAATGTCCA  GCCGATTCAA  TCGCCTACTG    60
GAGAAACAGT  GATTGGTGTC  CTTTATGTGA  AAAGTAATTT  AGAAAATAAA  TACCAAGAAA   120
TTACTAACAC  AGCAAGTATC  TTTTTCACTG  CTTCTATTAT  TGCCGCAGCA  ATCTCGATTA   180
TTGTGACCCT  ACTGATTGCA  CGATCAATCA  CGAAGCCGAT  TGGTGAAATG  CGCGAGCAAG   240
CCATTCGAAT  CGCTCGTGGT  GATTACGCTG  GAAAGTAGA   AGTCCATGGA  AAAGATGAAT   300
TAGGCCAATT  AGCAGAAACA  TTTAATCAAT  TATCAGAACG  GATTGAAGAA  GCACAAGAAA   360
CAATGGAAGC  AGAAGAATCG  TTTAGATAGT  GTCTTAACGC  ATATGACAGA  TGGTGTCATT   420
GCGACGGATC  GCCGCGGAAA  GGTGATTACG  ATTAATGAGA  TGGCCCTTTC  ATTATTAAAT   480
GTAAAAAATG  AAAATGTGAT  TGGGACCTCG  TTATTAGAGT  TGTTAGATAT  TGAAGAAGAT   540
TACACATTGC  GGAAGCTGTT  AGAAGAGCCA  GATGAACTGC  TGATTGATCG  CTCAACGTCT   600
GATCGTGAAG  AAGACCAAAT  GATTATCCGG  GTAGACTTTA  CGATGATTCG  TCGGGAATCA   660
GGATTTATTA  CTGGCTTAGT  TTGCGTACTT  CATGACGTCA  CAGAACAGGA  AAAAAACGAA   720
CGGGAAAGAC  GGGAATTTGT  TTCCAATGTT  TCTCATGAGT  TGCGACGCCT  TTGACAAGTA   780
TGCGTAGTTA  TATAGAGGCT  TTGAGTGAAG  GAGCTTGGGA  AAACCCTGAG  ATTGCGCCGA   840
ATTTCTTAAA  AGTCACGTTA  GAAGAAACCG  ACCGGATGAT  TCGTATGATT  AATGATTTGT   900
TAAATTTATC  TCGGATGGAC  TCTGGGAATA  CACATCTTCA  ATTAGAGTAT  GTGAATTTTA   960
ACGAATTGAT  TAATTTTGTC  TTGGATCGCT  TTGATATGAT  GATTGAAAAT  GAGCAAAAAA  1020
ATTACAAAAT  TCGCCGTGAA  TTTACTAAAC  GCGATTTATG  GGTAGAGTTA  GATACAGACA  1080
AAGTAATTCA  GGTTTTTGAC  AACATTTGA   ACAATGCGAT  TAAGTATTCG  CCAGATGGCG  1140
GCGTCATTAC  CTGCCGACTA  GTTGAAACAC  ATAATAATGT  CGTCTTTAGT  ATCTCGGACC  1200
AAGGTTTGGG  CATCCCTAAA  AAAGATCTCG  GGAAAGTCTT  CGAGCGTTTT  TATCGTGTGG  1260
ATAAAGCACG  TGCGCGAGCA  CAAGGTGGGA  CTGGTTTAGG  TTTAGCAATT  TCTAAAGAAG  1320
TAATTCGGGC  CCATAACGGG  AGTATTTGGG  TGGAAAGTAC  AGAAGGTGAA  GGATCAACTT  1380
TCTATATTTC  ACTACCATAT  GAACCTTATG  AAGAGGATTG  GTGGGAATGA  TGAAAAAATC  1440
AGAATGGATT  ACAAGAATTG  GCTTGATTTT  GATGGTCATT  TTAAGTATAT  ATTTTTCAGT  1500
CAATATCTGG  CTGAATTCTG  CCAAAAAAAT  ACCAGAAATG  AAGTCGGGAA  GCCAAGTCAC  1560
AACAGCTGTC  AATGAAAAAG  CCATTGGCGA  TGTCTATTTA  CCTTTGCAAT  TGATTCGAAT  1620
AGCCGATGGA  AAAGCGATGC  AAAGTAATCG  TGAAACATTA  ATTAGTAATG  TTCAAAATGA  1680
TATTAAAATG  GCTACGTTTG  GTAAATTGAC  ACAAGTTGTG  ACAAAAAATG  CAGAGCAACT  1740
TAAGCGCTAC  AACCAAATGG  AACAAGGCAT  TGAACTTCTT  TATCAAGGTC  CCTTTTTAAT  1800
CTCGGACTAT  GCTTCGATTT  ATAATCTATC  CATTAATTTT  ACTAACTTTA  ATGAGTTGAC  1860
```

| | | | | | | |
|---|---|---|---|---|---|---|
| GGACCAGTAT | TTTACGAAAA | TTCAATTGGA | TTTTAACGAA | AATAAGATAC | GTTTTTTAGA | 1920 |
| TTATGATCAA | TCCAACGTCT | ATGAAGCGCC | CATGACTGTT | AATAAGGCGC | GCTTAATGGG | 1980 |
| AATTATCAAT | AAAGAGGGAT | TGCAATATCA | AGACGTTTCC | GAAAATACGC | TAACCAAACA | 2040 |
| AGGACAATGT | TATTTAACCA | ATGATATGAA | GTTGAAAAAG | TACAGTTATA | TCTTANTTCG | 2100 |
| CAACCAGTTA | CTCGTTTTAG | GAATGCTTTT | TTCAATGAAA | CGGAAGATAT | CCAAACCAAT | 2160 |
| GAAGACAGTC | AAGACTTAAC | CTATACGAGT | AAAGAAGAAC | GATTGTTTGC | AGAAGAAAA | 2220 |
| CTGGGGAAAA | TCGATTTTAA | AGGGACCTTG | CCAGAAGAGA | ATAAACGGGA | CTCAATCTAT | 2280 |
| AATCAAAGCT | T | | | | | 2291 |

(2) INFORMATION FOR SEQ ID NO:10:

(i) SEQUENCE CHARACTERISTICS:
        (A) LENGTH: 3719 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Enterococcus faecalis
        (B) STRAIN: Clinical Isolate S2-3

(xi) SEQUENCE DESCRIPTION: SEQ ID NO:10:

| | | | | | | |
|---|---|---|---|---|---|---|
| AAGCTTCATT | AGAGCGTCAA | CTGTTTTGG | TGTTGGGTTC | ACAATGTCAA | TTAGACGTTT | 60 |
| GTGAGTACGC | ATTTCGAATT | GTTCGCGAGA | ATCTTTGTAT | TTATGAGTCG | CACGAATAAC | 120 |
| TGTGTAAAGT | GAGCGTTCTG | TTGGTAATGG | AATCGGACCT | GATACGTCAG | CTCCAGTTCT | 180 |
| TTTTGCTGTT | TCCACAATTT | TATCCGCTGA | TTGATCTAAA | ATACGGTGTT | CATACGCTTT | 240 |
| TAAACGGATA | CGAATTTTTT | GTTTTGCCAT | CTTGTTCCCT | CCTTCGCCTA | TTTTAAAAGT | 300 |
| AGACATAGCT | CCACGAAAAT | TTATCCGGCA | TGCTCGTTCA | TGGCAAAGCG | TCCGAGCGTG | 360 |
| TCGCAACCTC | TCGCTTCACA | GCCGGCAAAT | CAAATCGTTG | ATCTACCAAT | GCTTTTTACA | 420 |
| CTCCTGTAAA | CAGCACCTTT | TTGATTATAC | TATGAAAGGA | TAGTGTTAGC | AAGGATTTTC | 480 |
| TGCGTTTTTT | TAAAAGAATT | TTTTCTTGTT | TTGAAAAGCA | TTTGTTTTGT | TTTTCAATTC | 540 |
| TTTTCATTCT | ATTTTTATAA | AAAAAGAATT | TGAGATTCTT | TTTTTACCAG | AATCTCAAAT | 600 |
| TCTTTCTTTT | TTATTCTATT | AACCAATCCG | GCGCATTGGA | ATATCATTGT | TATCTGGATG | 660 |
| AACCAATAAA | TATTGAATAA | CATCAATATT | GCTTGCTTGG | AATGAGGCTG | CACATGCTTG | 720 |
| CAAATATAAG | TCCCACATTC | GATAGAAGCG | CTCGCCTTTT | TCGTCAACAA | TTTCTGTTTC | 780 |
| TATATTATGG | AAGTTTTTG | TCCAATGTTC | CAACGTCAAT | TGATAATCTC | TGCGCAAACT | 840 |
| TTCCAAGTCA | ATCACTTGCA | AGTCGTTTTC | TGTCATATGG | CCGACTAGCT | CAGTGACACC | 900 |
| AGGAATATAG | CCACCTGGGA | AAATATAACG | ATTAATCCAA | GCATTTTAG | CCCCACCTTG | 960 |
| TTGGCGACTG | ATCCCATGAA | TCAACGCCGT | ACCTTTAGGC | GCTAAATTTC | GCTGAACGAC | 1020 |
| ATCAAAATAT | TCATGTAGAT | TTTCCGCACC | GACATGTTCA | AACATCCCAA | CACTCGTAAT | 1080 |
| ATGGTCAAAA | GACTCTCCTT | TTAAATCACG | ATAATCCATC | AATTTGACAG | TCATTCGATC | 1140 |
| TTGTAGACCT | TCTTTTTCTA | TAATATGGCG | AATATGATGA | AATTGCTCTT | CACTTAATGT | 1200 |
| AATCCCAGTT | GCTTTGGCTC | CATATTCTTT | CACCGCAGTT | AAAATTAACG | TGCCCCAGCC | 1260 |
| GCAGCCAATA | TCCAGTAAAG | TGTCGCCCTC | TTTGATAAAC | AATTTATCTA | AAATATGATG | 1320 |
| AACTTTATTC | ACTTGCGCTT | GTTCTAATGT | ATCTTCAGGC | GTTTTAAAAT | AAGCACATGA | 1380 |
| ATACGTCATT | GTTTGGTCAA | GCCATTTTTT | GTAAAAATCA | TTTCCTAGAT | CGTAATGGCT | 1440 |

-continued

```
GTGAATATCC  TCTTGCGAAC  GTTTTTTTGA  ATGACTTTCT  TTAGGAAGCC  ATTTAATAAA   1500
TTTAGCATTG  TGTAAAAAGC  TATCCTTTTG  GTTATACACA  TCATAAATCA  GCGCTTGGAT   1560
ATCGCCTTCG  ATTTCAATTT  TGCGATCCAT  GTAGGCTTCC  CCTAAAGTTA  ACGAAGCGTT   1620
ATTCAGTAAA  TCCTTCACAG  GAATTTTTTC  ATTGAATACA  ATTTTAAAAA  CCGGATCCCC   1680
CGACCCTTGC  CCATACTCTT  TGACGGTACC  ATCCAGTAT   GTGACTTGTG  TCTTTTTTGA   1740
AAAAGACCAT  TTAAACAGTT  GACTGTACGT  TTCTTTTTCT  AACATTGCAT  TCCCTCCATT   1800
AAATACCATT  TGAAGCCAAA  ACAAAAGAA   GTCGCTTTCC  GGTAGTTCGT  CAAAACAAAC   1860
ACCACAGTCC  GTTCTAAACT  GAAGCACAGA  AAAGTTATCA  CCCCTTCTAT  GTTCCGCTTC   1920
TTTTTTGCAA  TTACAGTTCT  ATTCTACTCC  TCTTTTAAAA  ATTTGAACAT  TCTTTTAACG   1980
TAATACCTAC  TATTGTTATT  CTTTATCACA  AAAAAACTAG  AGCCAGTCCT  TGACAGACTC   2040
CTCTAGTTCT  AAATATTATG  CTTTCTTACG  CATCCGTTGT  TCCGCATGAG  TGTAAGCGCC   2100
ATGCCACACG  TGCCCCACAT  AAGGATTAAC  TTGAATACCG  TGTTTAATCG  CCGCTGCTAC   2160
AAATTTTTCG  CTAAAGTTAC  TGCTTCTAAC  ACCGAATAAC  CTTTCGCCAA  GCCAGCTGTG   2220
ATTGCCGCTG  AAAAAGTACA  ACCTGCACCA  TGATTATAAT  CAGTTGGATA  TAATTCATTT   2280
TCCAAAAGAT  GCGCGGTGTG  ACCATCGTAA  AATAAGTCCA  GTGCTTTTC   ACCAGCTAAG   2340
CGATGTCCCC  CTTTAACCAC  GACATGCTTG  GCTCCCATTT  GTACAATTCG  TTTTGCCGCT   2400
TCTTCCATCT  CCGCCACGGA  AGAAATTTCG  CCTAAACCAG  ATAAGATGCC  CGCTTCAATT   2460
AAATTAGGCG  TGGCAACTAA  TGCTAATGGC  AGTAAATCGT  TTTTAGGCCT  TCCACACTTT   2520
TGGGTTGCAG  AATTTGTGCC  GTTCCCTTAC  AAGCAATGAC  TGGGTCAATC  ACGACTTTTT   2580
GAATTTTTTC  TTGTTTAATG  TACTTACTAG  CCATTTTAAT  ATTTGTTCA   TTACCCCATC   2640
ATCCCCTGTT  TTCAAAGCCG  CTACTGGACC  GCCTGCAAAA  ACCGAAATCA  ATTGTTTTTC   2700
TAAGAGCGTT  TCTGGCAATT  CAGTTACTTC  ATGTGACCAA  CCTGTCGTAG  GATCCATCGT   2760
CACAATCGAG  GTTAAACTTG  AAAATCCAAA  AACTCCATAC  TCTTCAAATG  TTTTTAAATC   2820
TGCTTGAATC  CCTGCCCCTC  CAGTTGAATC  GGAGCCTGCA  ATCGTCAATA  CTTTTTCCAT   2880
TAAATCACCT  AACCTTTTTC  TCCAAGTATA  CGGAAGAAAC  AAGTCTGCTA  AAACAGCCAA   2940
TTGGCTTATT  TTTTAGCCAG  CCAATTTCTA  AACAAAAAAA  AGACCAGAGA  ATAAATTCTC   3000
TGGTCTTACG  TCCGAATACC  CCAGTTTTTC  ACGCTGGTTA  AAGCTATAGT  TAAAAAGTTA   3060
ATTATTTAAC  GATTTCAGTA  ACAACGCCTG  AACCTACAGT  ACGTCCGCCT  TCACGAATAG   3120
AGAAACGAGT  TCCGTCTTCG  ATAGCGATTG  GGTGAATTAA  TTCAACGTCC  ATAGCAACGT   3180
TATCACCAGG  CATTACCATT  TCAGTACCTT  CTGGCAATTC  TACAACACCA  GTAACGTCTG   3240
TTGTACGGAA  GTAGAATTGA  GGACGATAGT  TAGTGAAGAA  TGAGTGTGAC  GTCCGCCCTC   3300
TTCTTTTGAT  AATACGTATA  CTTCAGCTTT  GAATTTGTG   TGTGGAGTGA  TTGTAGCTGG   3360
TTTAGCTAAT  ACTTGTCCAC  GTTCGATATC  TTCACGTGCA  ACACCACGTA  ATAAAGCACC   3420
GATGTTGTCG  CCTGCTTCAG  CGTAGTCTAA  TAATTTACGG  AACATTTCAA  CACCTGTAAC   3480
AGTTGTTTTA  GATGTTTCGT  CTTTAATACC  AACGATTTCA  ACTTCGTCAC  CAACGCGAAC   3540
TTCACCACGT  TCAACACGGC  CTGTAGCAAC  AGTACCACGT  CCAGTGATTG  AGAATACGTC   3600
TTCGACTGGC  ATCATGAATG  GTTTGTCAGT  ATCACGTTCT  GGAGTTGGGA  TATATTCGTC   3660
AACTGCAGCC  ATTAATTCTA  AGATTTTTTC  TTCATAAGAC  TCGTCGCCTT  CTAAAGCTT    3719
```

( 2 ) INFORMATION FOR SEQ ID NO:11:

( i ) SEQUENCE CHARACTERISTICS:
  ( A ) LENGTH: 3480 base pairs
  ( B ) TYPE: nucleic acid
  ( C ) STRANDEDNESS: double
  ( D ) TOPOLOGY: linear ( i i ) MOLECULE TYPE: Genomic DNA ( v i ) ORIGINAL SOURCE:
  ( A ) ORGANISM: Enterococcus faecalis
  ( B ) STRAIN: Clinical Isolate S2- 7

( x i ) SEQUENCE DESCRIPTION: SEQ ID NO:11:

| | | | | | | |
|---|---|---|---|---|---|---|
| AAGCTTCTAG | CGTTTCGGAT | TGGCGCCTAT | GATGCACCAG | GAGAGCGACG | AATCAATACC | 60 |
| AAAAATATGC | CTACAGCAGG | AGGACTTGCA | ATCTACATTG | CTTTTGCTAG | TTCATGTTTA | 120 |
| TTGATTTTTC | GTTCGATTAT | CCCACAAGAT | TATATTTGGC | CGATTATTTT | GGCTGGTGGA | 180 |
| ATGGTTGTTT | TGACAGGCCT | CATTGATGAT | ATTAAAGAGA | TTACTCCAAT | GAAAAAAACA | 240 |
| ATCGGTATTT | TGTTAGCAGC | ATTAGTTATT | TTATTTTGTT | GCTGGAATTC | GGATAGATTT | 300 |
| TGTGACGTTG | CCAGTTGTTG | GAATGATTGA | TTTGCGCTGG | TTTAGTTTAC | CACTAACTTT | 360 |
| ATTGTGGATT | TTAGCGATTA | CGAATGCAGT | AAATTTAATT | GATGGTTTGG | ATGGTTTAGC | 420 |
| ATCAGGCGTA | TCCATTATTG | GATTAACCAC | GATTGGTATT | ACAGGGTATT | TTTTCCTACA | 480 |
| TGCTAAAACG | GTCTATATCC | CAATTGTTAT | TTTTATTTTA | GTTGCGAGCA | TTGCGGGATT | 540 |
| TTTCCCATAC | AATTTTTATC | CGGCTAAAAT | ATTTCTAGGA | GATACCGGGG | CGTTATTCCT | 600 |
| CGGGTTTATG | ATTGCAGTAA | TGTCGTTACA | GGGCTTGAAA | AATGCTACGT | TTATTACGGT | 660 |
| AATTACGCCA | ATGGTGATTT | TAGGTGTGCA | ATTACGGATA | CGGTTTATGC | AATTATTCGA | 720 |
| CGGCTATTGA | ACAAGAAGCC | CATTTCCTCA | GCAGATAAAA | TGCATTTACA | TCACCGCTTG | 780 |
| TTATCTTTAG | GTTTTACCCA | TAAAGGGGCG | GTCATGACTA | TTTATGCATT | AGCGTTAGTT | 840 |
| TTTTCCTTTG | TCTCTTTATT | GTTCAGCTAT | TCAAGTACAG | TAGCATCAAT | TTTATTAATT | 900 |
| GTCTTTTGTT | TAATTGGCTT | AGAACTATTC | ATTGAACTAA | TCGGTCTAGT | TGGCGAAGGG | 960 |
| CATCAACCGT | TGATGTATTT | GTTACGGATT | TTAGGGAATC | GTGAATATCG | TCAGGAGCAA | 1020 |
| ATGAAAAAGC | GACTTGGCAA | GCATTCTAAG | AGAAAGTAAA | GAAATCTTTA | GGTTGCTTTG | 1080 |
| CGAGAGCTAA | ACCTATGATA | TAATTCCATT | AAACTTAAAA | AAGTATATGT | GTGAAACATA | 1140 |
| TGCTTTTTTT | TTAAGACGAT | GTTTCAGTAG | TAAGGAGAAA | TGAGCATGCA | AGAAATGGTA | 1200 |
| ACAATCTCGA | TTGTCACTTA | TAATAGTCGT | TACATTTTTA | ATGTACTAGA | CCAATTAAAA | 1260 |
| GCCGAACTAG | GTACTGATAG | TATCTATGAT | ATTCATATCT | ATGACAATCA | TTCTGAAACA | 1320 |
| GCGTATCTTG | AAAAATTAAC | AACATATGAA | CCATTTATTA | CTATCCATCG | CGCTGAAGAA | 1380 |
| AATCAAGGGT | TTGGTCATGG | TCATAATCAA | GTGTTATTCA | ATGCTTCGAC | AAAGTATGCA | 1440 |
| ATTATTTTA | TCCCGATGTG | TTGGTTACTA | AAGACGTGCT | TGATCGTTAT | TAGACGTATC | 1500 |
| AAATAGATAA | GAACATTGCA | GTCGGTAGCC | CTAAAGTTGT | TAAATGAAGA | TGGCACGACG | 1560 |
| CAATATTTAG | TTCGTCAAAA | ATTAGATGTC | TTCGATTATA | TGTTACGTTT | TATTCCCTTT | 1620 |
| CAATTTGTAA | AGAAAATTTT | TGATAAACGT | TTGAGTATTT | ATGAATGTCG | CGATTTGTCG | 1680 |
| GATACAGAAA | CAACGGATAT | TAAAATGGGC | TCAGGCTGTT | TATGTTGAT | TGATCGTGAA | 1740 |
| AAATTCGTTG | AAATTGGTGG | GTTCGATGAA | CGTTTCTTCA | TGTACTTTGA | AGACAACGAT | 1800 |
| TTATGTTTAC | GCTTTGGCAA | AGCAGGCTAT | CGGATTCTCT | ATACGCCTTT | TGAAACGGTT | 1860 |
| GTTCACATGT | ATGAAAAGGG | CGCCCATAAA | AGTCGAAAAT | TGTTTAAAAT | CTTTATGCAA | 1920 |
| TCAATGGGGA | AATTTTTTAA | CAAATGGGGC | TGGAGGTTCT | TTAATGAGT | CAAAGATTAG | 1980 |

-continued

| | | | | | | |
|---|---|---|---|---|---|---|
| CGGTAGTCAT | CGTCTTATAT | CAAATGAAAA | TGGCTGATAC | GCCGAATTAT | TTGTTATTAA | 2040 |
| AAGAAGTGGT | AGACCACCCC | CAATTGCACT | TATTTATTTA | TGACAACAGT | CCACTTCCTC | 2100 |
| AAGAAGATGC | ATTATTTTTA | CAACCAAATG | TTACTTATCG | ACATAATCCT | GATAATCCAG | 2160 |
| GACTAGCGAC | CGCTTATAAT | GAAGCGATTG | CTTTTAGTCA | AGCGAATCAA | TGTGAATTAT | 2220 |
| TGTTGCTCCT | TGACCAAGAC | ACAGAAGTGC | CAGCCTCTTA | TTTTGATACG | TTGATCATCA | 2280 |
| TGCCATTAGA | TCCGACTGTG | GCAGTCTATG | TTCCAATTGT | AGAAGCAAAT | GGACAACAAA | 2340 |
| TTTCGCCAGT | ATATAGTGAT | CAATACGTTG | GGCTTAAAGG | AGCAAAGCCA | ACAGCAGGGA | 2400 |
| TAGCCAACCA | ACCGTTGATG | GCTATCAATT | CTGGTACAGT | TATTACGGCA | GAAACGCTAC | 2460 |
| GCTGGTTGGA | AGGATTTTCG | GAAGAATTTC | CTTTGGACTA | TTTAGACCAT | GGTTCTTTT | 2520 |
| ATCAATTAAA | TCAAGCCAAT | AAAAGATTG | AAGTCTTACC | AATCCACCTA | AAACAAGAAT | 2580 |
| TGTCTGTTTT | AGATTATCGT | ACAATGAGTC | CTCAACGTTA | TCGCTCTATT | ATTGAAGCAG | 2640 |
| AAACGTTATT | TTATCGTCGA | TATGATCAAG | AAAAGTTTTC | CCATCATCGA | CGCCATTTAT | 2700 |
| TTTTACGCAG | TAGTAAGCAA | TTTTTAACTG | TCAAAAATCG | CCAAATTTGG | CGGCAAACAT | 2760 |
| TGGCAGAATT | TCTCAAGTTA | ATGAAAGGAT | AATCTATGAT | CTCAGTTTGT | ATTGCGACAT | 2820 |
| ATAATGGAGA | AAAATATCTC | GCGGAACAAT | TAGATAGTAT | TCTTTTACAA | GTCAGTGAAG | 2880 |
| AAGATGAACT | AATTATTTCA | GATGATGGTT | CTACTGATCA | TACGTTGGAA | ATTTTGAGGA | 2940 |
| CGTATGCAGC | GAATTATCCC | CAAATTCAAT | TGTTACAAGG | TCCCAGGGCA | AGGAGTGATT | 3000 |
| GCTAATTTTG | CATTTTGCCT | TACGCATACG | AAAGGCGAAG | TAATATTTT | AGCAGATCAA | 3060 |
| GATGATGTTT | GGTTGCCAAA | TAAAGTAACG | ACGGTGACAG | AATATTTTGA | AGCGCACCCT | 3120 |
| GACATCCAAG | TGGTTATTAG | TGACTTGAAA | ATTGTTGATG | CGGATTACA | AGTTACCAAT | 3180 |
| CCCTCTTATT | TAAGTTTCGA | AAAGTCAAAC | CAGGGTTTTG | GCGAAATGCG | ATAAAAAGTG | 3240 |
| GCTATATTGG | GGCAGGTATG | GCCTTTCGTC | AAGAAATGAA | AAACGTCATT | TTACCCATTC | 3300 |
| CGCCAGAAGT | TCCTATGCAT | GATATGTGGA | TTGGCTTATT | AGCTGCACGG | AAGAAGCAAA | 3360 |
| CGGGTCTCAT | TAAAGAACCA | TTAGTGCTTT | ACCGAAGACA | TGGAGCGAAT | GTCAGCCCCA | 3420 |
| TTATTACCAA | AACAAGTTTC | CAACAAAAAT | TAAATTGGCG | TGTGAATTTA | TTAAAAGCTT | 3480 |

( 2 ) INFORMATION FOR SEQ ID NO:12:

( i ) SEQUENCE CHARACTERISTICS:
        ( A ) LENGTH: 2441 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Enterococcus faecalis
        ( B ) STRAIN: Clinical Isolate S2- 27

( x i ) SEQUENCE DESCRIPTION: SEQ ID NO:12:

| | | | | | | |
|---|---|---|---|---|---|---|
| AAGCTTCTGC | GCTAGGAACC | AGCCCTTTAA | TTACATCTCC | CCATACTGGA | TTTGACAATG | 60 |
| CCACTTGATA | AGCAAAAATC | ACAAAAATAA | CAACAATTAA | AGCAACAACA | ATAGCTTCAA | 120 |
| TTTTTCTAAA | ACCAATTTTT | GTCAATAACA | ACAAAGTAA | AACATCAAAT | ACCGTAATGA | 180 |
| AGACAGCCAG | ACCTAAAGGA | ATATGAAATA | ATAAATATAA | GGCAATTGCG | CCCCCGATAA | 240 |
| CTTCAGCGAT | ATCTGTAGCC | ATAATTGCTA | ACTCTGTTAA | AATCCATAAT | ACAATACCTA | 300 |
| ACGTCTTACT | AGTTCTAGCA | CGAATCGCTT | GTGCTAAATC | CATCTGTGAA | CAATGCCTAA | 360 |
| TTTAGCAGCC | ATATATTGGA | GCAACATTGC | AATCAAACTG | GAAATTAAAA | TAATCGACAT | 420 |

|  |  |  |  |  |  |  |
|---|---|---|---|---|---|---|
| CAATAAATAT | TGAAAATTTT | GTCCCCCAGT | AATTGAAGTA | GACCAGTTTC | CTGGATCCAT | 480 |
| ATACCCCACT | GCTACCAATG | CTCCTGGACC | TGAGTAAGCA | AATAACGTTT | TCCAAAAACT | 540 |
| CATATTTTTA | GGCACGTCGA | TGGTGCCATT | AATTTCTTCA | AGCGAAGGAC | CATTTGCATA | 600 |
| TTCAATCAAA | TGATGTCTTT | GCTTTGGTTC | ATGTTCTTCT | GAATTTTTCA | ATTCAATTCC | 660 |
| TTCTTTCGTT | TTGCAATAAT | TTAAAAGGC | CCTTCCCGTT | AGAAGGTTAA | CCTCTAGTAT | 720 |
| ATTTTAGGTA | CACCTAAAAT | ATACTGCTAA | AAATAACAAA | ATGCAAGACT | GAAAGAAAA | 780 |
| TTTTGACAGT | GTAAAAATAG | ATTGTCGTAA | ATGTGCGATC | TTAAAGTTTG | AAGAAATCAG | 840 |
| GGTAGCTGGT | AGTTGATTAT | CTTAAGAAGT | AGAAAATAAG | GGACCTAAGT | CATTTCGGCT | 900 |
| TAGGTCCCTT | ATTTTATTTT | TATTCGGTTA | TTCTATTAAG | AATGGATGCT | ACAATTTCTG | 960 |
| TCGTGTCAGC | TGAATGATTT | CTAAAATCTC | GTAAACTTAA | TCTGACGAAA | ACCTTCAAGT | 1020 |
| ACTTCGGGCA | ACTTATTTTN | CCCCCATTCA | AAAGTTCCAT | CATTTCTTTT | CAATAATCTT | 1080 |
| TGTAAAATTT | CTTCTTTCTC | GACCGCTAAC | AAAAAATGAT | AAACGTCAAT | GCCTGCTCGT | 1140 |
| CTCAGATATC | CAATCAGCTC | TTCTTCATAT | TCATTTTTAT | AAAGGGTCAT | TGTAACAATA | 1200 |
| ATCGGCCGTC | CAGACTCTTT | GGACATTCGT | TTAATAAAT | GAGCATTCCA | GCAACGCCAT | 1260 |
| TCCTGATACT | CCTGAAAATC | ATTTTCTTTC | ATTCTTCGG | GAACTAGCTC | CATCAATGCA | 1320 |
| CTACCAATAA | TTTCTGGATC | ATAAATGATT | GCGTTGGGAA | GTTTTGTTG | TAACTCATGT | 1380 |
| GCAATGGTCG | TTTTTCCGGA | TCCAAACGCA | CCGTTAACC | AATAATTAT | CATAATTTCC | 1440 |
| TTTTCTTCTG | AACAAATTTC | TTTGTTGTTT | AATTTAGGTG | CTAGATTACT | TTTAATTTTT | 1500 |
| TTAGCCATTC | ACTTATAGTT | ACTACTTACA | TCTTTAACAG | TAAACGAGAC | AAACTAAAAA | 1560 |
| TACAACATCC | TACGCTATTA | ACCTCGGGTT | ATATAACATA | CTCATCTGAT | AATTTCTCCC | 1620 |
| TAAAAAACA | GAATGTGGGC | AATCTTTTA | AGAATAATTG | AATAGAATAA | CAACAAACAG | 1680 |
| TAATTCAGGT | ATAACCAGCT | AGAAATTGTT | TTATTTTAG | TCACGAGTAT | GATAAGCATG | 1740 |
| TAAATCAAAT | AGAATCATAT | TAGGTGAGGT | TACTCTGAAG | AACACAGGTT | ATCGCTCGGA | 1800 |
| AATGTCGAGA | GACAGTAACG | AGTAAAGCAG | GGATTGTCGA | ATTAAGGCTT | TCCTAAGATA | 1860 |
| ACTAGAATTT | TTTTCTTACG | TCTCAGAAAG | CCAAAGCTCA | ATTATTGTGA | TTACCCTATA | 1920 |
| ATCTTCTTCT | TTTATTCGGC | GACCTCTTTA | ATATGATTAA | TTGGAGGTTT | TTAAATTGAA | 1980 |
| AGCTGTCACT | GCATCATCTA | AGAAAAATAC | CCTACTTGCT | AAAAGTATCG | GGAATCTTAC | 2040 |
| CTTGCTCATC | ATTTTAGGCA | TTTTCATTTT | TATCATCGTC | TTCTCTTGGC | TAAAAATGAA | 2100 |
| TCGCCCTCTC | CACACCCTTC | CCTCAGAAGA | ATTCCTCGCA | ACACCAAGTA | AAACAGATGA | 2160 |
| TTTCTTATCT | CCATCAAATC | TTTTTTACTT | TTCAATTCGA | ACCATGTTTC | GAATGATTGT | 2220 |
| GGGGATGGCT | TGGTCCTTCC | TGTTTTCCTT | TGTTTTTGGT | ATTTAGCCG | TAAAATATAA | 2280 |
| AACGGCACGA | AGAGTCATTT | TACCATTAGT | TAATTTCCTT | GAATCTGTTC | CATTGCTAGG | 2340 |
| TTTTTTGACC | TTTACAACTG | CTTGGTTACT | TGGTTTATTT | CCAGGAAATG | TGATGGGCGC | 2400 |
| AGAAGCGGTT | GCTATTTTTG | CCATCTTCAC | AGGTCAAGCT | T |  | 2441 |

( 2 ) INFORMATION FOR SEQ ID NO:13:

( i ) SEQUENCE CHARACTERISTICS:
        ( A ) LENGTH: 9515 base pairs
        ( B ) TYPE: nucleic acid
        ( C ) STRANDEDNESS: double
        ( D ) TOPOLOGY: linear ( i i ) MOLECULE TYPE: Genomic DNA (v i) ORIGINAL SOURCE:
    (A) ORGANISM: Pseudomonas aeruginosa
    (B) STRAIN: Clinical Isolate P2-2

(x i) SEQUENCE DESCRIPTION: SEQ ID NO:13:

```
AAGCTTTCCT  CCAGACCCTT  CACCGCCGTG  GAGATCGACG  GCTGGGCGAT  GTACAGCTTG    60
CGCGAGGCCT  CGGCCACGCT  GCCGCATTCC  ACGGTGGTCA  CGAAATACTT  GAGTTGCCGC   120
AAGGTATAGG  ACGCCACTGC  AAGACCTCAT  CGGCGCATCA  TCCTCCCCGG  GCCGGGCGTG   180
CGCGCCTCGA  TTGTTGTGTC  CGCCGCGCTG  CAAGCAAGTT  GCAGGCCGCT  GCCGAGCGTC   240
GCGCGCTGGC  CGCGGAACGA  TTGCCCGCCT  GCACGATAAC  CCAGCACGAC  GCACTTTGCC   300
GGGGCACGCC  TGGCCAGCTT  TTTCTTATGT  CCCGAGGACA  TTTTTAATAA  TTTTCCTTCG   360
CCGCGGCTTG  CGCGACCATC  CTTCCCCATC  GACCCCATGG  ACAGCGGTTC  GCCTCCCGGC   420
GGTCCGGGCC  ATGCGTGCAG  AACCACGACC  GGCGCAGACC  GGCGAGATAA  CAAGGAGAAG   480
GTGGGGTGTT  CGAACTCAGC  GATTGGCAAC  GGCGCGCCGC  GACACAGCGC  TTCATCGACC   540
AGGCCCTGAT  CGGCGGCCGC  CAGCGTCCAG  CCGCCAGCGG  CGCTACCTTC  GACGCCATCG   600
ATCCGGCGAG  CAATCGCCTG  CTGGCGCGGG  TCGCGGCCTG  CGATGCGGCC  GACGTCGACG   660
CGGCAGTGGC  CGCCGCCCGC  CGCGCCTTCG  ACGAAGGCCC  CTGGGCGCGT  CTCGCCCCGG   720
TCGAGCGCAA  GCGCGTGCTC  TGCGCCTGGC  CGAGCTGATG  CTGGCCCATC  GCGAAGAGCT   780
GGCGCTGCTC  GACTCGCTGA  ACATGGGCAA  GCCGGTGATG  GACGCCTGGA  ACATCGATGT   840
ACCCGGCGCC  GCCCACGTCT  TCGCCTGGTA  TGCGGAAAGC  CTCGACAAGC  TCTACGACCA   900
GGTCGCGCCG  GCCGCCCAGC  AGACCCTGGC  CACCATTACC  CGCGTGCCGC  TGGGGGTGAT   960
CGGCGCGGTG  GTGCCGTGGA  ACTTCCCGCT  CGACATGGCC  GCCTGGAAGC  TCGCCCCGGC  1020
CCTGGCCGCC  GGCAACTCGG  TGGTGCTCAA  GCCGGCCGAG  CAGTCGCCGT  TCTCCGCCCT  1080
GCGCCTGGCC  GAGCTGGCCC  TGGAGGCGGG  GGTGCCGGAA  GGCGTGCTGA  ACGTGGTGCC  1140
GGGCCTCGGC  GAGCAGGCCG  GCAAGGCCCT  CGGCTTGCAC  CCGGAGGTGG  ACGCACTGGT  1200
GTTCACCGGC  TCCACCGAGG  TCGGCAAGTA  CTTCATGCAG  TATTCCGCGC  AATCCAACCT  1260
CAAGCAGGTC  TGGCTGGAGT  GCGGCGGTAA  GAGTCCGAAC  CTGGTGTTCG  CCGATTGCCG  1320
CGATCTTGAC  CTGGCGGCGG  AAAAAGGCGC  CTTCGGCATT  TTCTTCAATC  AGGGCGAGGT  1380
CTGTTCGGCG  AACTCGCGCT  TGCTGGTGGA  GCGTTCGATC  CACGACGAGT  TCGTCGAGCG  1440
CCTGCTGGCC  AAGGCCCGCG  ACTGGCAGCC  GGGCGATCCG  CTGGACCCGG  CCAGCCGCG   1500
CCGGCGCCAT  CGTCGACCGC  CGGCAGACCG  CCGGGATTCT  CGCCGCCATC  GAGCGGGCGC  1560
AAGGCGAGGG  CGCGACCCTG  CTCGCGGTGG  CCGCCAGTTG  ACGATCAACG  GTTCGGACAA  1620
CTTCATCGAA  CCGACCCTGT  TCGGCGACGT  ACGCCCGGAC  ATGCAGCTGG  CCCGCGAGGA  1680
AATCTTCGGC  CCGGTGCTGG  CGATCAGCGC  CTTCGACTCC  GAGGACGAGG  CCATACGCCT  1740
GGCCAAGGAC  AGCCGCTACG  GCCTCGCCGC  CTCGCTGTGG  AGCGACGACC  TGCACCGTGC  1800
GCACCGGGTG  GCGCGGCGCT  TGAATGCCGG  AACGTGTCGG  TGAATACCGT  GGACGCGCTG  1860
GACGTCGCGG  TGCCTTTCGG  CGGCGGCAAG  CAGTCCGGCT  TCGGTCGCGA  CCTGTCGCTG  1920
CATTCCTTCG  ACAAGTACAC  CCAGTTGAAG  ACGACCTGGT  TCCAGTTGCG  CTGAAGACGC  1980
GACGGACGCG  ACACGACTCG  ATGCCGATAA  CGACAACAAG  AGGACGATCG  AATGAACGAC  2040
ACGCCGAACG  TGCGTGAGCC  GGCCCTGCGC  CGCGTGCTCG  GCTGGGACC   GCTGCTGGCG  2100
GTGGCCATCG  GCCTGGTGGT  TTCCCAGGGC  GTGATGGTAC  TGATGCTGCA  AGGCGCCGGG  2160
ACGGCCGGCC  TGGGCTTCAT  CGTGCCGCTG  GGAGTGGCCT  ACCTGCTGGC  GCTGACTACG  2220
```

| | | | | | | |
|---|---|---|---|---|---|---|
| CCTTTTCCTT | TTCCGAGCTG | GCCCTGATGA | TTCCCCGCGC | CGGTAGCCTG | AGCAGCTACA | 2280 |
| CCGAGGTGGC | CATCGGGCAT | TTCCCGGCGA | TCCTGGCGAC | CTTTTCCGGC | TACGTGGTGG | 2340 |
| TGGCGATGTT | CGCCCTCTCG | GCGGAACTGC | TGCTGCTCGA | CCTGATCATC | GGCAAGGTCT | 2400 |
| ACCCCGGCGC | GCTGCCGCCG | ATGCTGGTGC | TACGGCGTGC | TCGGCCTGTT | CACCCTGCTC | 2460 |
| AACCTGCTCG | GCATCGACAT | CTTCGCGCGC | CTGCAGAGCG | CGCTGGCGCT | GCTGATGATG | 2520 |
| ATCGTCCTGC | TGGTGCTCGG | CCTGGGTGCG | GTGAGCAGCG | ACCACGCTTC | CGCGCAGACC | 2580 |
| GCCCTGGCGA | GCGGCTGGAA | CCCGCTGGGG | GTAAGCGCCC | TGGCGCTCAC | CGCGATGGCC | 2640 |
| GTGTGGGGCT | TCGTCGGCGC | CGAGTTCGTC | TGCCCGCTGG | TGGAGGAGAC | GCGGCGTCCG | 2700 |
| GAGCGCAACA | TCCCGCGTTC | GATGATCCTC | GGCCTGAGCA | TCATCTTCCT | GACCATCGCC | 2760 |
| CTCTACTGCT | TCGGTGCGCT | GCTGTGCATC | CCGCAGGCGG | AACTGGCCGG | CGACCCGCTG | 2820 |
| CCACACTTCC | TCTTCGCCAA | CCGCGTGTTC | GGCGAGTACG | GCCAGCTGTT | CCTGGTGATC | 2880 |
| GCCGCGATCA | CCGCCACCTG | CAGCACCCTC | AACTCGTCGC | TGGCGGCGAT | CCCGCGGATG | 2940 |
| CTCTACGGGA | TGGCGCAGAA | CGGCCAGGCC | TTCCCGCAAT | TCAAGCAGCT | CAGCCGGCGG | 3000 |
| GCGCGCACGC | CCTGGGTGGC | GGTGCTGTTC | GTCGCCGCGA | TCACCGGCCT | GCCGATCCTG | 3060 |
| ATCCTCGGCC | AGGACCCGGA | CTCGATCAAC | CTGCTGCTGC | TCGCCGCCGC | GCTGGCCTGG | 3120 |
| CTGCTGGCCT | ACATCATCGC | CCACGTCGAC | GTGCTGGCCC | TGCGCCGTCG | CTATCCGCAC | 3180 |
| ATCGCCCGTC | CGTTTCGCAC | GCCGTTCTAC | CCGCTGCCGC | AACTGTTCGG | CATCGCCGGG | 3240 |
| ATGATCTACG | CGGTGGTCCA | CGTCTCGCCG | ACCCCGGAAA | TGACCGGACG | GATCTTCGCC | 3300 |
| AGCGCCGGCG | TGGTGCTCGG | CGTGGTCTCG | CTGGTGGCGG | TGGTGTGGAT | CAAGGGCGTG | 3360 |
| ATGCGCAAGC | CCCTCTTCGT | ACCCGAACCG | CTCGAGACGG | CCGGTGAGAC | TGCCCAGGGC | 3420 |
| AAGTCCGTCG | CCCTCGATCC | CCTGCAATCC | CTTCGGCCTG | ACGCGCCAAG | GAACAAGGA | 3480 |
| GAACACAGAC | GATGACCGCT | CAGCTCAACC | CGCAGCGCGA | CACCCGCGAC | TACCAGCAAC | 3540 |
| TGGACGCCGC | GCACCACATC | CACGCCTTCC | TCGACCAGAA | GGCGCTGAAC | CGCGAAAGGC | 3600 |
| CCGCGGGTGA | TGGTCCGCGG | CGATGGCCTG | CAGCTCTGGG | ACAACGACGG | CAAGCGCTAC | 3660 |
| CTGGACGGCA | TGTCCGGCCT | CTGGTGTACC | AACCTCGGCT | ACGGCCGCCA | GGACCTCGCC | 3720 |
| GCCGCCGCCA | GCCGCCAGCT | GGAACAACTG | CCGTACTACA | ACATGTTCTT | CCACACCACC | 3780 |
| CACCCGGCGG | TGGTGGAGCT | TTCCGAGATG | CTCTTCAGCC | TGCTGCCGGA | CCACTACAGC | 3840 |
| CACGCGATCT | ACACCAACTC | CGGCTCCGAG | GCCAACGAGG | TGCTGATCCG | TACCGTGCGG | 3900 |
| CGCTACTGGC | AGATCCTCGG | CAAGCCGCAG | AAGAAGATCA | TGATCGGCCG | CTGGAACGGC | 3960 |
| TACCACGGCT | CGACCCTGGG | CAGCACCGCG | CTCGGCGGGA | TGAAGTTCAT | GCACGAGATG | 4020 |
| GGCGCATGCT | GCCGGACTTC | GCCCACATCG | ACGAACCCTA | CTGGTACGCC | AACGGCGGCG | 4080 |
| AGCTGAGCCC | GGCCGAAGTT | CGGTCGCCGC | GCGGCGCTGC | AACTGGAGGA | GAAGATCCTC | 4140 |
| GAACTGGGCG | CGGAGAACGT | CGCCGCCTTC | GTCGCCGAGC | CCTTCCAGGG | CGCCGGTGGC | 4200 |
| ATGATCTTCC | CGCCGCAAAG | CTATTGGCCG | GAGATCCAGC | GCATCTGCCG | GCAGTACGAC | 4260 |
| GTGCTGCTGT | GCGCCGACGA | AGTGATCGGC | GGCTTCGGCC | GCACCGGCGA | ATGGTTCGCC | 4320 |
| CACGAACACT | TTCGCTTCCA | GCCGGACACC | TTGTCCATCG | CCAAGGGCCT | GACGTCCGGC | 4380 |
| TACATCCCCA | TGGGCGGCCT | GGTACTCGGC | AAGCGCATCG | CCGAGGTGCT | GGTGGAGCAG | 4440 |
| GGCGGGGTGT | TCGCCCACGG | CCTGACCTAT | TCCGGCCACC | CGGTGGCGGC | GGCGGTGGCC | 4500 |
| ATCGCCAACC | TCAAGGCTGC | GCGACGAGGG | CGTGGTCACG | CGGGTCAGGG | AGGAGACCGG | 4560 |
| CCCCTACCTG | CAACGCTGCC | TGCGCGAGGT | CTTCGGCGAC | CATCCGCTGG | TCGGCGAGGT | 4620 |

-continued

| | | | | | |
|---|---|---|---|---|---|
| CCAGGGCGCC | GGCTTCGTCG | CCGCGCTGCA | GTTCGCCGAG | GACAAGGTGA | CCCGCAAGCG | 4680
| CTTCGCCAAC | GAGAACGATC | TGGCCTGGCG | CTGCCGCACC | ATCGGCGGCT | TCGAGGAGGG | 4740
| CGTGATCATC | CGCTCCACCC | TCGGCCGCAT | GATCATGGCC | CCGGCGCTGG | TGGCCGGGCG | 4800
| TGCCGAGATC | GACGAACTGA | TCGACAAGAC | CCGTATCGCG | GTGGATCGCA | CCGCGCGCGA | 4860
| GATCGGCGTG | CTCTGACGCG | CCCCGGCGGC | CCGGCCTCGG | CCGGGTCGCC | TGCGACACGG | 4920
| AGCGTCCCCC | CATAACGACG | ATGCGGCGCC | TGGCGACCGC | GCGCGGAACC | GTTTCGGCCT | 4980
| CTGGCGGCAA | CTGCCTAAGC | AACATCACAA | CAATGCCAAT | CGGCTGTGGG | AGTGTTCCAT | 5040
| GTTCAAGTCC | TTGCACCAGT | ACGCACACGT | GTTTTCCCGG | TTGTCCCTGT | TCGTCCTGGC | 5100
| GTTCGCCGCG | GCGGCCCAGG | CGCAGAGCCA | GAGCCTGACG | GTGATCTCCT | TCGGCGGCGC | 5160
| GACCAAGGCC | GCCCAGGAAC | AGGCCTATTT | CAAACCCTTC | GAGCGAAGCG | GCGGCGGGCA | 5220
| GGTGGTCGCC | GGCGAATACA | ACGGCGAAAT | GGCCAAGGTG | AAGGCCATGG | TCGACGTCGG | 5280
| CAAGGTCAGC | TGGGACGTGG | TCGAGGTGGA | GAGCCCCGAA | CTGCTCCGCG | GCTGCGACGA | 5340
| GGGGCTGTTC | GAACGCCTCG | ACCCGGCGCG | TTTCGGCGAC | CCCGCGCAGT | TCGTCCCCGG | 5400
| CACTTTCAGC | GAGTGCGGGG | TGGCCACCTA | CGTCTGGTCG | ATGGTGATGG | CCTACGACTC | 5460
| GACGAAGCTG | GCCAGGGCGC | CGCAGTCCTG | GGCGGATTTC | TGGAACGTCC | GCGAGTTCCC | 5520
| CCGGCAAGCG | TGGCCTGCGC | AAGGGCGCCA | AGTACACCCT | GGAAGTGGCG | TTGCTGGCCG | 5580
| ACGGGGTGAA | GGCGGAGGAC | CTCTACAAGG | TACTCGCCAC | CCCGGAGGGG | GTCAGCCGCG | 5640
| CCTTTCGCCA | AGCTCGACCA | GCTCAAGCCG | AACATCCAGT | GGTGGGAGGC | CGGCGCCCAG | 5700
| CCGCCGCAAT | GGCTGGCGGC | CGGCGACGTG | GTGATGAGCG | CGGCCTACAA | CGGGCGCATC | 5760
| GCCGCTGCGC | AGAAGGAGGG | GGTGAAACTG | GCCATCGTCT | GGCCCGGCAG | TCTCTACGAT | 5820
| CCGGAGTACT | GGGCGGTGGT | GAAGGGCACC | CCGAACAAGG | CGCTGGCGGA | GAAATTCATC | 5880
| GCCTTCGCCA | GCCAGCCGCA | GACGCAGAAG | GTGTTCTCCG | AGCAGATCCC | CTACGGGCCG | 5940
| GTACACAAGG | GCACCCTGGC | GTTGCTGCCG | AAGACGGTGC | AGGAGGCGCT | GCCGACCCGC | 6000
| GCCGGCCAAC | CTCGAAGGCG | CGCGGGCGGT | GGATGCCGAG | TTCTGGGTGG | ACCACGGCGA | 6060
| GGAGCTGGAA | CAGCGTTTCA | ATGCCTGGGC | GCGCGCTGAG | CGCTGCGCGT | CGGCAAAAAA | 6120
| AATGACGGGC | CCCAAGTCGT | CCGGGCCCGT | CGGGTCAAAG | CGCTGACGGG | GTGATCAGCG | 6180
| CAGCTCTTCC | AACAACCCCT | GCAGATACCG | ACAGCCCTCG | GTATCCAGCG | CCTGCACCGG | 6240
| AAGGCGCGGC | GCCCCCACCT | CCAGGCCGGA | GAGGCCCAGG | CCGGCCTTGA | TGGTGGTCGG | 6300
| CAGGCCCCGG | CGGAGGATGA | AGTCGAGCAG | CGGCAACTGC | CGGTAGAACA | GCGCGCGGGC | 6360
| CTTCTCCAGG | TCGCCGTCGA | GCACCGCCTG | GTAGAGCTGG | CCGTTGAGCG | TCGGGATCAG | 6420
| GTTCGGCGCG | GCGCTGCACC | AGCCTTTCGC | GCCGGCCACG | AAGGCCTCCA | GCGCCAGCGC | 6480
| GTTGCAGCCG | TTGTAGAAGG | GCACCCGGCC | TTCGCCGAGC | AGGCGCAGCT | TGTGCATGCG | 6540
| CTGGATGTCG | CCGGTGCTCT | CCTTGACCAT | GGTCACGTTG | TCCACTTCGC | GGACGATGCG | 6600
| CAGGATCAGT | TCCACCGACA | TGTCGATGCC | GCTGGTGCCC | GGGTTGTTGT | AGAGCATCAC | 6660
| CGGCACGCCG | ATGGCTTCGC | CAACCGCGCG | GTAGTGCTGG | AACACTTCCG | CCTCGTTGAG | 6720
| CTTCCAGTAG | GAGATCGGCA | GGACCATCAC | CGCCTCGGCG | CCGAGGGATT | CGGCGAACTG | 6780
| CGCGCGGCGC | ACGGTCTTGG | CGGTGGTCAG | GTCGGAGACG | CTGACGATGG | TCGGCACGCG | 6840
| ATGGGCGACG | GTCTTCAGGG | TGAAGTCGAC | CACCTCGTCC | CATTCCGGGT | CGCTCAGGTA | 6900
| GGCGCCTTCG | CCGGTGCTGC | CGAGCGGGGC | GATGGCGTGC | ACGCCGCCGT | CGATCAGGCG | 6960
| CTCGATGGAG | CGGCCGAGGG | CCGGCAGGTC | GAGACCGCCG | TCGGCGCCGA | AGGGGGGTGA | 7020

| | | | | | | |
|---|---|---|---|---|---|---|
| TGGTGTAGCC | GATGATGCCG | TGGATGGATG | CGGACATTGG | ATGTACCCGT | GACATTGAGT | 7080 |
| GGGAAATGCC | AGGACGGACC | TGGTGGGAAA | GGTCGTTCAG | CTCAGGCAGT | CGCTGTTGCG | 7140 |
| CGGCAGGCAG | CGCCGGGCGT | AGTAGTTGAA | TGCGGCGCCG | TGGCGCTTCG | GGGTGGAGAT | 7200 |
| CCAGTCGTGG | GCCTCGCGCG | CCAGGGCCGG | CGGGATCGGC | TTGATCTCTC | CGGCGGCCAT | 7260 |
| CGCCAGCAAC | TGCATCTTCG | CCGCGCGCTC | GAGCAGCACC | GCGATCACGC | AGGCCTCCTC | 7320 |
| GATGCTCGCA | CCGGTGGCCA | GCAGGCCGTG | GTGGGAGAGC | AGGATGGCGC | GCTTGTCGCC | 7380 |
| GAGGGCGGCG | GAGATGATCT | CGCCTTCCTC | GTTGCCTACC | GGCACGCCCG | GCCAGTCCTT | 7440 |
| GAGGAAGGCG | CAGTCGTCGT | ATAGCGGGCA | AAGGTCCATG | TGCGAGACCT | GCAGCGGTAC | 7500 |
| TTCCAGGGTC | GACAGCGCGG | CGATGTGCAG | CGGGTGGGTG | TGGATGATGC | AGTTGACGTC | 7560 |
| CGGGCGGGCG | CGATAGACCC | AGCTGTGGAA | GCGATTGGCC | GGATTCGCCA | TGCCGTGCCC | 7620 |
| GTGGAGGACG | TTGAGGTCTT | CGTCGACCAG | CAGCAGGTTG | CCGGCGCTGA | TCTCGTCGAA | 7680 |
| GCCCAGGCCC | AGTTGCTGGG | TGTAGTAGGT | CCCCGCCTCC | GGGCCGCGCG | AGGTGATCTG | 7740 |
| CCCGGCGAGC | CCGGAGTCGT | GGCCGGCCTC | GAAGAGAATC | CGGCAGGTCA | GGGCCAGCTT | 7800 |
| TTGCCGGTCA | GTCCACGTAT | TATCGCCGAG | GCTGCTTTTC | ATCTGCTTCA | GCGCGTGCTG | 7860 |
| GATCAGTTGA | TCCTTGGGTA | ATTCCAGTGT | CGTAACCATG | CGAGGTTCCT | TTGACGGAGC | 7920 |
| GAGTCGGGGG | AAACGCCAGG | CAGTTGCGCG | CCACGCAACG | ACCCGGCTGT | AAATGACACG | 7980 |
| GATCAAGTTA | TATGACACAA | AGTGTCATTT | AGCAAGAGAG | AAGTTTCATC | GCCATCGGGA | 8040 |
| GAAGGCTGTC | CTCAATGTCC | ATGCGCTTGA | AATTGCTGAG | AAAAAAACTC | GGGGTCACGC | 8100 |
| TGGAGACCCT | GGCCGACAAG | ACCGGCCTGA | CCAAGAGCTA | CCTGTCCAAG | GTCGAGCGCG | 8160 |
| GGCTGAACAC | GCCGTCCATT | GCCGCCGCGC | TGAAGCTGGC | GAAGGCGTTG | AACGTGCAGG | 8220 |
| TGGAGGAGCT | GTTCTCCGAG | GAAAGCGACG | GTGTCGACGG | CTACAGCATC | GTTCGTCGCG | 8280 |
| ACCAGCGCAA | GTCGCTGTCC | AGCGGCGACG | ACGGCCCGGC | CTACGCCTCC | CTCGTCGCAG | 8340 |
| CAGATCGGCG | CCCGCGCGCT | GTTGCCGTTC | ATCGTCCACC | CCCCGCGCGA | TTTCAGTCAC | 8400 |
| TCGACGTTCA | AGGAGCACCT | CGGCGAAGAG | TTCATCTTCG | TCCATGAGGG | CCAGGTCGAG | 8460 |
| GTCGACTTCA | TGAACCAGCG | GATCATCCTC | GAGCGCGGCG | ACGCCCTGCA | TTTCAACGCA | 8520 |
| CAGAAGCCGC | ACCGCATCCG | CTCCCTGGGG | GAGACCCAGG | CGGAATTGCT | GGTGGTGATC | 8580 |
| CACAGCGACG | AATGAGGCGA | CGGCTTCGGT | CGATCGGATG | CTTGCTAACG | TTCTGTTCGA | 8640 |
| TTATCGAACT | GTTAATCGAT | TATCGGATTG | TGAGCCCTCG | GACCCCGGCG | TAAGGTTCTC | 8700 |
| GTCACGTGCC | GTCCAGGCAG | CGCACAACAA | GACGAGACCC | GACCGATGGC | TGAAATCCTC | 8760 |
| TCCCTGCGCG | AACGGTGCGA | CGCTTCGTCC | ACGATGGCGA | CAGCGTCGCC | CTCGAAGGCT | 8820 |
| TCACTCACCT | GATCCCGACG | NCCGCCGGCC | ACGAGCTGAT | CCGCCAGGGC | AGGAAAGACC | 8880 |
| TGACGCTGAT | CCGCATGACT | CCCGACCTGG | TCTACGACCT | GCTGATCGGT | GCAGGCTGCG | 8940 |
| CGAAGAAGCT | GGTGTTCTCC | TGGGGCGGCA | ACCCCGGTGT | CGGTTCGCTG | CACCGCCTGC | 9000 |
| GCGACGCGGT | GGAGAAGGGC | TCGGCCGCAA | CCGCTGGAGA | TCGAGGAACA | CAGCCACGCC | 9060 |
| GACCTCGCCA | ACGCCTATTT | TGCCGGCGCC | TCCGGGCTGC | CCTTCGCGGT | NTGCGCGCCT | 9120 |
| ACGCCGGCTC | CGACCTGCCG | AAGGTCAACC | CGCTGATCCG | CAGCGTCACC | TGCCCGTTCA | 9180 |
| CCGGCGAAGT | GCTGGCGGCG | GTGCCCTCGG | TGCGTCCGGA | CGTCAGCGTG | ATCCACGCGC | 9240 |
| AGAAGGCCGA | CCGCAAGGGC | AACGTGCTGC | TCTGGGGCAT | CCTCGGCGTG | CAGAAGGAAG | 9300 |
| CGGCCCTGGC | GGCGAAGCGC | TGCATCGTCA | CCGTCGAGGA | GATCGTCGAC | GAACTGGACG | 9360 |
| CCCCGATGAA | CGCCTGCGTC | CTGCCGAGCT | GGGGCGCTCA | GCGCCGTGTG | CCTGGTGCCC | 9420 |

-continued

| | | | | | |
|---|---|---|---|---|---|
| GGCGGCGCGC | ATCCGTCCTA | TGCCCACGGC | TACTACGAGC | GCGACAACCG | CTTCTACCAG | 9480
| GACTGGGACC | CGATCGCCCG | CGACCGCGAA | AGCTT | | | 9515

( 2 ) INFORMATION FOR SEQ ID NO:14:

( i ) SEQUENCE CHARACTERISTICS:
        ( A ) LENGTH: 2471 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Pseudomonas aeruginosa
        ( B ) STRAIN: Clinical Isolate P2- 7

( x i ) SEQUENCE DESCRIPTION: SEQ ID NO:14:

| | | | | | |
|---|---|---|---|---|---|
| AAGCTTGTTC | CAGGCCCTCG | ACCGCTGCGA | TCTTCTGCGG | GTAGGCGGCG | ATGGTCTGTT | 60
| CGGAGTTCGC | CAACTGCAGG | CGACGCTGCG | CCAGCTGCGC | CGCCTGCACG | CCGGCAAGCA | 120
| TCAGGTCCTG | ATCGAGCGAG | GGGTTGAAGC | CGCGCACGAA | CTCGCTGAAC | TGGTCCACGC | 180
| CGAACAGGGT | GGCGATGAGC | TGGCGCTGAT | CGCTCGGGGT | CCGCGCGGCG | ATTCGGGCGA | 240
| AATCGTCGAG | GCGGTTCTTC | TCGATGAAGC | AGAAGCGATA | CTCAGCTTCG | TCGGGCTGGA | 300
| CGGCCTGCGC | CTCGCCCGCN | GCCGTAGACG | ACAGGACTGG | CGCGATGTGG | CGGCGCAGGC | 360
| GAGCGTTGTT | GCAGTACGTC | CGCTGGTCGA | CCGCTTGGCC | TGCGCTTCGC | TGATCGAACC | 420
| GAGCATCGCC | ACTTCCAAGG | CTTCGCAGAA | GCTGCTCTTG | CCGGTGCCGT | TGGCACGTNA | 480
| GACCAAGGTG | ATGTCATGGC | TGAGGTCGAA | CGTCTCCTGC | CGCATGAATC | CTCGAAACGG | 540
| CCCGACTTCG | AGCTGGTGCA | GTCGCCCGAG | CGCCGGCCCG | TTTTCGGGGC | CGCGCGCGTC | 600
| CCCGTCGTAG | GCGACAGGCA | TCTGCGCCAA | GATGCGCGAT | GGCCAGCGGC | GCCAAGCCGC | 660
| GTGGGAGCGC | CCCCCGGCGT | GCAGCACCGA | CCTCGGCCAG | TGGCTGCAGG | TGATCGAGCA | 720
| CCAGGGTGCG | CCAGCCGGCG | CACCGTTTCG | TCGTGCACGT | GCCGCTGCGT | CAAGTGCGCC | 780
| AGGAACCGGT | GGTACTCCGA | ACGTATGCTT | GCCACAGCGA | CCCCTCACTT | GGTCAACCAC | 840
| TGACCGTAAG | CCTCCACATC | GATCATGGGG | ACCGTTCCAC | TGAACTGAAG | CTGCGCGATC | 900
| AGCTTGAAAA | GAAACGCGGT | CGCCGGCTTG | TTTTCGTTGG | TGTAGCTGTA | CGCGCCGCTG | 960
| GCTTGGTCAT | AGAAAAAGTG | CCCGTGGGCG | GCAACGCATC | CGATGTCCAG | ACGCCCCTCG | 1020
| GTGAGGTTTG | CGTTCAGCGC | CTTGTCCATG | GATGGGCCCA | ATGCAGGACT | CCATTCGCTC | 1080
| TCGAAGGTGA | GCAAGCCACC | CAGAATCGGA | ATCAACGCTT | CGCTGGGTAG | GTCCCGCCAG | 1140
| CGTGCGGGAT | CGGCAGGCTC | GTGCGGTGCA | GCCTGCGCAC | ACTGGCGACC | TTCTCCTGGC | 1200
| ATAGCCACAA | GCCCCGCGTC | AGCCGTCTGC | TTGGCCTCGA | ACACGGCGTA | CACGCTTTCG | 1260
| GCTGGAATGA | TCGTCTCGTT | CTCGTAGGTG | AAGATAAAAG | GCGAATATTG | CCGATCAAAC | 1320
| ACCACCACAT | CGATCTGCTG | GCTGAAGTTC | CCCAGGCTGT | CCACCACATG | CGCCTTCGCC | 1380
| GCCTGGTACC | GTTTGGGCAG | ATAGGTATCC | AGCATGTCGA | TCCAGACGTT | CTCGCTCGCA | 1440
| TCCCCCTTCG | TACCCGGGTG | ACCGAAGGTC | TTGCGTACTA | CGGACAAGCG | CTGCTGGATG | 1500
| TCTTCATGCA | GGGACGACAG | GAGCTGGGAA | AGCGACCACT | GGGACATGCT | GTACCTCGAT | 1560
| GGGACGTGTA | TGGAAGCCGA | TGGAATCAGG | ACAGTGGGAA | CTTGGGGCCA | AACAGTGCGC | 1620
| GCCAGGGCGA | AGCGCTTCGA | TATTGCGACC | ACGACGCGTG | TGGTCGATGG | CGATGCTTGC | 1680
| GTCCTGGCTC | GCCTGGAACA | GCAGCTGCTN | GCGNGCGCTG | CTTGCGCGCG | GCATCCATAT | 1740
| CGTTGCTGAT | CGCCGGGCCA | AGTCCGGCGG | GATCCGGCCA | CTCGTCATGA | ACACGATCGG | 1800

| | | | | | | |
|---|---|---|---|---|---|---|
| CAAGCGTGGC | AAAGAACGAC | TGGATCTCGC | GATCGAACGA | TCCTCCCCAG | CCGCCGTAAA | 1860 |
| GACACTCAAG | GGCCATTACC | TCGATCAGGA | ACGAGGGCTT | CACCGGCTTC | TGATCGCCGT | 1920 |
| GCTTGGGATT | GTTGTTCCAG | TACTTCACCA | TGCGCACGAG | ACCTTTCCAC | TCATTGCCAT | 1980 |
| AGGCTTGGTG | CGCTGCGGTC | GCCTTGTCCT | TATGGATCTC | CGGGTCCGTC | TTGATCCACT | 2040 |
| TTCCGGACGC | CGTATCGGGG | ATCTCATACT | GGTCGCCGGT | GTCGAATGCG | GGCACCGCAT | 2100 |
| CCACGCTGAC | CACCCGGTAG | TCCGTGTTGT | CCTCCGCGTC | GATGTGAACA | CCGAAATCCA | 2160 |
| CGTTGATCGA | GNGCGCCTGT | TTGCGCACGG | CCGCCGAACC | GTATTCTCC | ACCAATGCAG | 2220 |
| AGTGGAAATC | ATCCAGCACT | ACCGATGCGG | CCTTGCCGTG | GTAATGCTTC | TCCGAGTCCT | 2280 |
| TCAGCACGAA | GAAGATGTCG | ATATCCTTGA | GCGGCTTCGT | CTTCGTGTAT | CGAGCATAGG | 2340 |
| ACCCGGTCAG | GAACTGCGCG | CAATGCCGAA | CTTGGTCTGC | AGGTAGTCCC | GCACTTCGTT | 2400 |
| CTGGCGTTGC | GAGGCATTCT | TCTGCTCGCG | TTCGTTGAGT | TCCAGACGCG | ACTTGAACTT | 2460 |
| GCGAAAAGCT | T | | | | | 2471 |

(2) INFORMATION FOR SEQ ID NO:15:

(i) SEQUENCE CHARACTERISTICS:
(A) LENGTH: 5247 base pairs
(B) TYPE: nucleic acid
(C) STRANDEDNESS: double
(D) TOPOLOGY: linear (ii) MOLECULE TYPE: Genomic DNA (vi) ORIGINAL SOURCE:
(A) ORGANISM: Pseudomonas aeruginosa
(B) STRAIN: Clinical Isolate P2-17

(xi) SEQUENCE DESCRIPTION: SEQ ID NO:15:

| | | | | | | |
|---|---|---|---|---|---|---|
| AAGCTTCGAG | GGGGCTGGGC | GAGGATCGAC | CGGCCCCGCT | CGTGTCGGAA | GGGAAGGCCA | 60 |
| GGGCTGGCCT | GCCCGTTCGG | CGCTTCGGCA | GGCTGGCGCA | GAACGATGCA | AGGTCGTTCG | 120 |
| GGTCAGCATC | AGGGATGAAA | TGACTGACAG | GAGTCGGGAT | GCTGCGTTAC | GTCGTGGGTT | 180 |
| TTCTCGCGTT | CACCGTGCTG | GCGGCCTATC | TGTTGCTGGG | GGTTTCCCAG | CACGCCTTCC | 240 |
| TGCCGTGACC | GGTCGGCATG | GCGGCTTCAG | CTGCGTTGCG | GAAGAGGCTG | TGGCGGCCGT | 300 |
| GCGGGATGCC | GGTTTTCGGC | TTGCCGTGCC | TTGCGTTGCA | GGCGTCGCGC | CGACGCGGCA | 360 |
| CGCCAGGGAA | GGCCCACAGG | GTGACGCCGG | CGAGGCCCAG | CCAGGCGACG | ATCAGCAATG | 420 |
| TGACGAAGGA | TTCGGGAGTC | ATGGTTCGTC | CTCCTCTTAC | CCAAGGATAG | ACCCTGCGGG | 480 |
| AAGGGGAATT | ACTGCAATCG | GTCTTCGACC | ATGGTCTGAA | ACGCGGTCAC | TCGGGGCCGG | 540 |
| CGCCGACCAG | GGCCAGGCAG | CCGGTGAGGC | TGGTCAGCAG | GGGCAGGGCG | AGCAGGAAAG | 600 |
| CCAGCCAGAT | GGCCTCCATG | CGCAACAGCG | TGGCGCCGAG | GAACAGCGCG | ACCAGGAGGA | 660 |
| TGGTCATGAG | CAGGGCGGTC | CAGCCGAAGT | ACATGGCGAA | GTTGTCGATG | CCCAGGCCGA | 720 |
| TGCCCCAGCC | CAGCAGCAGG | GCCCATACCC | CGGCCAGAGC | CAGGCCGAGG | GCCAGCATGC | 780 |
| TCGCCAGGGT | CCGGGCGGAC | GGGGCATGCA | GCGGGTGGTT | GCGGAATAGC | TCGTAGAAGA | 840 |
| TCGGCGTATT | CATCGGCGTC | ACCTCCGCAG | GGGAACTTCC | AGCCTAGTCC | AGCGGGCGAG | 900 |
| ACGGCCCTAG | ACCTATTTGT | CATTACGAGG | CGTGACCTCA | GGCCGTTAAC | ATCCATCTTT | 960 |
| TTCCAGGCGA | TGCCGTGCAT | CGGGCTGCGG | GCCCGCTCAC | CGTTCGTCGC | GCTGAGTCGA | 1020 |
| AAAAGAAACC | GAAAGGGTTG | CGTGCATGAG | TTGGCGAACT | CGCCTCGTTC | GAGGTGGATG | 1080 |
| GGTATCAACT | GGTCTATCAG | GACCTGGGTG | AAGGCACGCC | GGTGCTACTG | GTCCACGGTT | 1140 |

-continued

| | | | | | | |
|---|---|---|---|---|---|---|
| CGCTGTGCGA | CTACCGCTAC | TGGCAATGGC | AGTTGCGCAG | CTCGGCAAGC | ACCACCGGCT | 1200 |
| GATCGTGCCG | AGCCTGCGTC | ACTACTACCC | CGAGCGCTGG | GACGGGCAGG | GTGCGGACTT | 1260 |
| CACCAGCGCC | CGCCACGTCG | CCGACCTGCT | GGCGCTGGTC | GAGCGGCTCG | GCGAGCCGGT | 1320 |
| ACACCTGCTC | GGCCATTCCC | GTGGCGGCAA | CCTGGCGTTG | CGCCTGGCGC | TGGCCGCTCC | 1380 |
| GGACGCCCTG | CGTTCGCTGA | GCCTGGCCGA | TTCCCGGCGG | CGACTATGCC | GCCGAGGTCT | 1440 |
| ACGCCCACGC | CGGCCTGCCT | GCGCCCGAGG | AACCATTGGA | ACGCAACCAG | TTCCGGCGCC | 1500 |
| AGGCGCTCGA | ATTGATCCGT | GGCGGCGAGG | CGGAACGGGG | ACTGGAACTG | TTCGTCGATA | 1560 |
| CGGTGAGCGG | CGCCGGGGTA | TGGAAACGCT | CGTCGGCGAC | GTTCCGCCGA | ATGACGCTGG | 1620 |
| ACAACGCCAT | GACCCTGGTC | GGGCAGGTGG | CCGACCAGCC | GCCGGCGCTG | GCGCTGTCGG | 1680 |
| AACTGCGCTC | GATCGACCTG | CCGAGCCTGA | TCCTCAATGG | CGAACGCAGC | CCGCTGCCAT | 1740 |
| TCCCGGCCAC | CGCCGAGGCG | CTGGCGGCGG | CCCTGCCGCG | CGCCGAGCTG | CAACGCATCC | 1800 |
| AGGGCGCGTC | CCATGGCCTC | AATGCCACCC | GTCCGGCGGC | TTTCAACCGG | TCGGTGCTGG | 1860 |
| AGTTCCTGGC | GCGCGTCGAT | GGCGTTGCGC | CGGACGTGGA | AACGTCCTGA | AGCGAGGCCG | 1920 |
| GGCGAACTGA | CCGCTCGTCA | GCTCGCCGCG | GATGCTTTAC | CATGCGTTCG | CGCCGGATCA | 1980 |
| GCTCCGGCGT | TTTTCGTCAG | TATCCATTCC | CAGTGATCTC | CGTCCGCGCG | CTTCGGCGCA | 2040 |
| GGGGTGCCGC | AAGGCGCCTG | CCACTGTGAG | GCAGGCCGGC | CCGGCGGGCG | ACGCTTACTG | 2100 |
| GCACATCCCA | ACCCACGTGG | CCTTTGGTAG | GGTCACCACT | AGAGAGAGCG | CCATGCCCAT | 2160 |
| CATTACTCTT | CCCGACGGCA | GTCAACGTTC | CTTCGATCAC | CCGGTCTCCG | TGGCCGAGGT | 2220 |
| GGCCCAATCC | ATCGGCGCAG | GCCTGGCCAA | GGCGACCCTC | GCCGGCAAGG | TCGACGGCCG | 2280 |
| CCTGGTCGAC | GCCTGCGACA | CCATCGATCG | CGACGCGACC | CTGCAGATCA | TCACGCCCAA | 2340 |
| GGACGAGGAA | GGACTGGAGA | TCATCCGCCA | CTCCTGCGCC | CACCTGGTCG | GCCATGCGGT | 2400 |
| CAAGCAGCTC | TATCCGACCG | CGAAGATGGT | CATCGGCCCG | GTGATCGAGG | AAGGCTTCTA | 2460 |
| CTACGACATC | TTCTTCGAGC | GCCCCTTCAC | CCCCGAGGAC | ATGGCGGCGA | TCCAGCAGGC | 2520 |
| ATGCGCGAGC | TGATCGACAA | GGACTACGAC | GTGATCAAGA | AGATGACCCC | GCGCGCCGAG | 2580 |
| GTCATCGAGC | TGTTCAAGTC | CCGTGGCGAA | GACTAACAAG | CTGCGCCTGA | TCGACGACAT | 2640 |
| GCCGGACGAG | AAGGCCATGG | GCCTGTACTT | CCATGAGGAG | TACGTGGACA | TGTGCCGCGG | 2700 |
| CCCGCACGTG | CCGAACACTC | GCTTCCTCAA | GGCGTTCCAG | CTGACCAAGA | TTTCCGGCGC | 2760 |
| CTACTGGCGC | GGCGACTCGA | AGAACGAGCA | GTTGCAACGC | ATCTACGGCA | CCGCCTGGGC | 2820 |
| CGACAAGAAG | CAACTGGCGG | CCTACATCCA | GCGCATCGAA | GAGGCCGAGA | AGCGCGACCA | 2880 |
| TCGCCGCATC | GGCAAGCAGC | TCGACCTGTT | CCACCTGCAG | GAAGAAGCGC | CGGGCATGGT | 2940 |
| GTTCTGGCAC | CCGAATGCTG | GAGCGTCTAC | CAGGTGCTCG | AGCAGTACAT | GCGCAAGGTC | 3000 |
| CAGCGCGACC | ATGGCTATGT | CGAAGTGCGT | ACCCCGCAGG | TGGTCGACCG | CATCCTCTGG | 3060 |
| GAGCGTTCGG | GCCACTGGTC | GAACTACGCC | GAGAACATGT | TCACCACCTC | CTCGGAAAGC | 3120 |
| CGCGACTACG | CGGTCAAGCC | GATGAACTGC | CCGTGCCACG | TGCAGATCTT | CAACCAGGGC | 3180 |
| CTGAAGTCCT | ACCGCGACCT | GCCNTGCGCC | TCGCCGAGTT | CGGCGCCTGC | CACCGCAACG | 3240 |
| AGCCGTCCGG | CGCGCTGCAC | GGATCATGCG | GTACGCGGCT | TTACCCAGGA | CGACGCGCAT | 3300 |
| ATCTTCTGCA | CCGAAGAGCA | GGTGAAGAAG | GAAGCGGCCG | ATTTCATCAA | GCTGACTTGC | 3360 |
| AGGTCTACCG | CGACTTCGTT | TCACCGACAT | CGCCATGAAG | CTGTCGACCC | GTCCGGCCAA | 3420 |
| GCGCGTCGGT | TCCGACGAGC | TGTGGGATCC | CGAAGGCGCG | CTGGCCGATG | CGCTGAACGA | 3480 |
| ATCCGGCCTG | GCCTGGGAAT | ACCAGCCGGG | CGAGGGCGCG | TTCTACGGGC | CGAAGATCGA | 3540 |

| | | | | | |
|---|---|---|---|---|---|
| GTTCACCCTG | AAGGACTGCC | TCGGCCGTAA | CTGGCAGTGC | GGCACCCTGC | AGTACGACCC | 3600 |
| GAACCTGCCG | GAGCGCCTGG | ACGCCAGCTA | CATCGCCGAG | GACAACAACC | GCAAGCGCCC | 3660 |
| GGTGATGCTG | CACCGTGCGA | TCCTCGGGTC | CTTCGAGCGC | TTCATCGGCA | TGCTCATCGA | 3720 |
| GCACTACGCC | GGAGCCTTCC | CGGCCTGCTG | GCGCCGACCC | AGGCAGTGGT | GATGAACATC | 3780 |
| ACCGACAAGC | AGGCCGATTT | CGCCGCCGAG | GTGGTGCGGA | TCCTCGGGGA | AAGCGGATTC | 3840 |
| CGTGCCAAGT | CCGACTTGAG | AAACGAGAAG | ATCGGCTTTA | AATCCGCGA | GCATACTTTG | 3900 |
| CTCAAGGTTC | CCTATCTCTT | GGTTATTGGA | GATCGGGAAG | TTGAATCGAA | GGCCGTCGCG | 3960 |
| GTGCGTACGC | GCGAAGGGGA | AGACCTGGGC | TCCATGCCCG | TCACCCAGTT | CGCTGAGCTG | 4020 |
| TTGGCACAGG | CGGTTTCCCG | GCGTGGTCGC | CAAGACTCGG | AGTAATCATT | ATTAAGCGTG | 4080 |
| AAATGAGACA | GGATAAGCGA | GCTCAACCGA | AACCCCGAT | CAACGAGAAC | ATCTCGGCTC | 4140 |
| GTGAGGTACG | GTTGATTGGA | GCTGATGGCC | AGCAGGTTGG | TGTTGTTTCG | ATCGATGAGG | 4200 |
| CGATCCGCCT | AGCCGAAGAG | GCGAAGCTGG | ACCTGGTTGA | GATTTCGGCC | GACGCGGTGC | 4260 |
| CTCCTGTCTG | CCGCATCATG | GACTACGGCA | AGCACCTGTT | CGAGAAGAAG | AAGCAGGCTG | 4320 |
| CGGTCGCCAA | GAAGAACCAG | AAGCAGGCGC | AGGTCAAAGA | AATCAAGTTT | CGTCCAGGGA | 4380 |
| CGGAAGAAGG | GGATTACCAG | GTAAAACTAC | GCAACCTGGT | ACGTTTCCTT | AGTGAAGGGG | 4440 |
| ACAAGGCCAA | GGTATCCCTG | CGATTCCGCG | GCCGTGAGAT | GGCTCACCAG | GAGCTGGGGA | 4500 |
| TGGAGCTGTT | GAAGCGGGTC | GAAGCCGACC | TCGTGGAGTA | CGGCACCGTC | GAGCAGCATC | 4560 |
| CTAAGCTGGA | AGGACGCCAG | CTGATGATGG | TCATCGCTCC | CAAGAAGAAA | AAGTAACCAC | 4620 |
| CAGGGCACTG | GCAGGCCTTG | CGGTTATGCG | TAATCACTCA | ATGCGGAGTA | TCCGAACATG | 4680 |
| CCAAAGATGA | AGACCAAAAA | GTGGGCGCGG | CCAAGCGCTT | CAAGAAGACT | GCTGGTGGCC | 4740 |
| TCAAGCACAA | GCACGCCTTC | AAGAGCCACA | TCCTGACCAA | GATGACCACC | AAGCGTAAGC | 4800 |
| GTCAACTGCG | CGGCACCTCG | ATGCTGAACA | AGTCTGACGT | TGCGCGCGTA | GAACGCTCCC | 4860 |
| TGCGTCTGCG | CTGATTATTA | AGGTAGAGGA | TTAATTCATG | GCTCGTGTTA | AGCGTGGCGT | 4920 |
| TATCGCCCGT | CGTCGTCACA | AGAAAATTCT | GAAGCTCGCC | AAGGGCTACT | ACGGTGCACG | 4980 |
| CTCGCGCGTG | TTCCGCGTTG | CCAAGCAGGC | GGTGATCAAG | GCTGGCCAAT | ACGCCTACCG | 5040 |
| TGACCGTCGT | CAGCGCAAGC | GTCAGTTCCG | CGCACTGTGG | ATCGCCGTA | TCAACGCTGG | 5100 |
| TGCTCGTCAG | AACGGTCTGT | CCTACAGCCG | CCTGATCGCC | GGCCTGAAAA | AGGCGGCCAT | 5160 |
| CGAGATCGAC | CGTAAGGTCC | TGGCCGATCT | GGCAGTGAAC | GAAAAAGCGG | CGTTTACCGC | 5220 |
| GATTGTCGAG | AAAGCGAAGG | CAAGCTT | | | | 5247 |

( 2 ) INFORMATION FOR SEQ ID NO:16:

( i ) SEQUENCE CHARACTERISTICS:
        ( A ) LENGTH: 2812 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Pseudomonas aeruginosa
        ( B ) STRAIN: Clinical Isolate P4- 5

( x i ) SEQUENCE DESCRIPTION: SEQ ID NO:16:

| | | | | | |
|---|---|---|---|---|---|
| AAGCTTTGGT | GATCTTAACG | TGACAAGCTC | CTTAGAAAAA | TTTTATGAGT | TTATTAGCGG | 60 |
| GGTCTTTCTT | GATCCGACTG | TACCAAGACT | TTCAACTCGT | AAAATACGCA | AGCACAAAAG | 120 |
| CACTGAAATG | CACTCTGCAC | GTTTGTCGCC | GTCCACGGTA | GCGGCATCCC | TCAATCACAC | 180 |

-continued

```
CGAAGCGGTG  AATCTTTCTA  CCTATGCAGA  GGCAACACCT  GAACAGCAGC  AATCCGAGTT   240
CAGCCTGTTT  TGGGATGCAA  TACGCCACGC  TGCTCATGTT  GTGCGTGAGC  GAAGCCGCAA   300
GGCTGTAGCA  AGTAGTGTCG  CAATAGCGGC  GGGTCACTGC  GAGGATTTCA  ATAAGCCGAC   360
GTCTGCCACT  GATGTGGGAT  TGATTATAGA  GCCGAACTGC  CGCACCCAAT  ATGGTTGTTT   420
GTACTGCGAA  AACTATTTAT  GTCACGGCGA  TGAGGAGGAT  CTGCATAAAA  TTCTGAGTTT   480
GCAATACGTG  GTCAATGCCG  TGCGTAAATC  GGCCCCGAT   GCAGCGCATA  CTGAGGCACT   540
TTTCAAAGAG  TTATCTATCC  GGATCGAGTT  TATAGTCGAT  GCTCTTAGTG  AGCGCTCTAG   600
CTCGGTGAAA  CAGACAGTCG  AAAAGGTTAA  AGCTAAGGTG  TTTGAATACG  GCGAGTTAAC   660
TAAGTTTTGG  GAAGTCCGGT  TGGGTCGCTA  TGAAAAATG   GGATCGTAT   TTTGAGTGCT   720
GCTGTTCAGT  CGATAGGTAG  TCTTTTTTCT  AGCGGCCAGT  TTCCAGTCAC  CAGCCAGCCA   780
GATAGTGCGG  CTCAGCTGTA  TGGGAAGCCC  GCGTCGGATT  TTGTTATCTG  TCGCACTGAG   840
TATGGCAATG  CAACGGCAGT  GTACGGCGAG  TCTGTATGGG  ACTTTAACCC  GTACAGGCTG   900
AGTGCAAAAA  AAATTGGCCG  AATACGCTTC  GATATGGTGT  TCGGTGATTA  TGGTCATGAT   960
CAGCAAGCGC  TGATCGAAGA  AGCCAAATAT  CTTCTGTATT  GTCTTATTTA  TTTCGCTGGC  1020
GGTGGGCGGA  TTGGTAAGCT  GAGTGCATCT  ACGATTATTT  CATATTGGGT  TGTGCTGCGC  1080
ATCGCTATGA  AGTTCTGCTA  TGCGCAGAAA  AAGAAGTCAA  TGGTTGGTGT  GCTGTCCTTG  1140
CAGCAGCTTT  TTACCGTGCC  TGTTTATCTA  GCGGCTTTTG  TTAGTGAAAG  TAATTTTGAC  1200
AAGACGGTTC  TTAGTGGGAT  ATTGCACGGA  TTGATTAGTG  TGGGCGAGGA  ACGCCTAGGG  1260
TATGTTGTGC  TGAATCCAAG  AGTTTTTGAT  TTGAGAAGAC  CTGATTCTAA  ACAGCATTCC  1320
GGTAATTCCG  ACACGCCTTT  ATTTGAATTT  AATAATATTG  TGGCGACCTG  CTCGATCATC  1380
TTACTTGGGT  GTTGGGAATA  TTGATTCATT  TATATCGTGC  TTTGCTGATG  AGTATTTCGG  1440
TCTTACTCCG  CACCGTCAAA  AATCTTTGGG  GGTTGGTGGT  AAGTCGCGCT  ATCGCCCCGG  1500
TATTCAGCAA  GCAATAGAGG  AATATGGTCT  GGCTGCGGTT  TTTGTCGGTG  AGTTTGCCTG  1560
TTCCGAAAAG  AGAAAGCTGC  AGCGAGTCCT  TCTCAAGATG  CAGTATGTGG  TGAGAATGGT  1620
GATACACCTA  TATACCGGCA  TGCGTGATCA  AGAGGTGATG  CGTATGTCTT  ATAACTGCTT  1680
ATCTGATCAA  GTCGTGAGAT  GTTCAGTGGT  TGATGATCAA  GGTTTTATGC  GCGATCAACC  1740
GCAATCAGTA  CACATATTAT  CGACTACCAC  GAAGTTTAGC  GGTTACAAGA  AAGAAAGCGC  1800
ATGGTTCGCG  GCAGGCGAAG  TCGTCAAGGC  GGTCGAGGTT  GGCCAGGCGA  TTTGTCGTGG  1860
TTTAGCCCGG  CTCTATAGGA  TTGAACTGGA  TGATCGTTGT  CCGCTATTCA  TCAATCCGTC  1920
CGTCCTGTGT  AAAACGAAGA  ATTGTGCAGA  AGTTGGTGTA  ACAGACTTTA  CATTGAGAGC  1980
AACGATGGCA  GTGCTTTGAA  ATCCTTATCG  ATTCAATCAG  AGGATTTACA  AGAGTTGGCT  2040
CAGAGCGACC  CTTCTCGTGA  CTTTTACAAT  GAGCCAGATT  TTGCAGTAGG  CCAGCCCTGG  2100
CCGCTGACTA  GCCATCAATT  CCGACGTTCG  TTGGCCTTCT  ATGGAAGCAG  TAGCGGCTTT  2160
CTCTCGTTAC  CGACTCTGCG  AGCGCAGTTC  AAGCATATGA  CCCATTCAGA  TGGCGCGCTA  2220
TTATGCGAAT  GGCTTTGATA  ACTTGCGCAC  CATTTTTGGC  TACTATGACG  AGAAGAAAAT  2280
AGACTTCGTG  CTACCATATA  ACCACTTTGC  TTTCGAGTTC  CAGATGGCCA  TGCCGATGTC  2340
GGTGGCCAAT  CAGTTGATTG  CAGATCTGCT  GTTCAAAGAA  GAACCGCTGT  TGGTGGCAC   2400
CGGTTCATAC  ATGCAGAGGC  AGAAAGAACG  TGTTGAAGCT  GGCGAGATAA  AGATTGAAGA  2460
TATTCGTGCC  GATACAGAGC  TTCGGGTGAA  GAACGGTGCA  ATTAGCTATC  GGCCAACGCT  2520
ACTCGGTGGT  TGCACCAAGG  TGGGCCGCTG  CGATTCCTTC  ATGCTCGGTG  ACTATACTGA  2580
```

| | | | | | |
|---|---|---|---|---|---|
| ATGTTTGTCC | TGCGAGGGTG | CGATTATCAA | GCCCTCCAGG | TTAAGTGCGG | CCATTGAGGA | 2640
| TGCGAAAAAC | GAGTTGTCAA | ACTACGCAGA | AGACTCAGGC | GAATATCAAA | TTGTGAAGGG | 2700
| CGATATTGAG | CGCCTAATGG | TTTTCAAGAC | TCGCCTGATC | GACACTGTGG | AGCTTTAGTC | 2760
| ATGAAGTCTG | GTGAAGGAAT | AAGCAAGGGG | GTTGGTGCCT | GTCAGGAAGC | TT | 2812

( 2 ) INFORMATION FOR SEQ ID NO:17:

( i ) SEQUENCE CHARACTERISTICS:
        ( A ) LENGTH: 3615 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Escherichia coli
        ( B ) STRAIN: Clinical Isolate EC- 24

( x i ) SEQUENCE DESCRIPTION: SEQ ID NO:17:

| | | | | | |
|---|---|---|---|---|---|
| AAGCTTTTCT | TGCGTGTTCT | TGTGAGGCTT | CCTTCGCCAT | TATCATCACG | ATCCACATAA | 60
| ATAAAGCCGT | AGCGCTTAGA | CATTTGTGAA | TGAGATGCAC | TGACTAAATC | AATTGGCCCC | 120
| CAACTGGTGT | ACCCCATAAT | ATCCACACCA | TCGGCAATCG | CTTCATTTAC | CTGTACCAGG | 180
| TGATCGTTTA | AATAGGCAAT | TCGATAATCG | TCCTGTATCG | AACCATCCGC | TTCAACGCTG | 240
| TCTTTTGCGC | CTAATCCGTT | CTCGACAATA | AATAACGGTT | TTTGATAACG | ATCCCAAAGC | 300
| GTATTTAACA | GAACCCGTAA | TCCAACCGGA | TCAATTTGCC | ACCCCACTC | TGAACTTTTC | 360
| AGATGCGGAT | TGGGGATCAT | ATTCAGTATG | TTGCCCTGCG | CATTTTTATT | AATGCTTTCG | 420
| TCGTGGGAAC | ACAACCAGTC | ATGTATAACT | AAAGAGATGA | ATCGACGGTA | TGTTTAAAT | 480
| CTCTGCGTCA | CTTTCAGTCA | TCTCAATGGT | GATATTGTGG | TCGCGGAAGA | AACGCTGCAT | 540
| ATAGCCGGGA | TACTGGCCAC | GCGCCTGAAC | ATCACCAAAG | AACATCCAGC | GCCGGTTCTC | 600
| TTCCATGGCC | TGCAACATAT | CCTGTGGCTG | GCAGGTGAGG | GGGTAAACCA | GCCCACCGAG | 660
| AAGCATATTG | CCGATTTTCG | CTTCGGGGAG | CAGGCTATGA | CAGGCTTTAA | CTGCCCGCGC | 720
| ACTGGCAACC | AGTTGATGGT | GGATAGCCTG | ATAAACTTCC | GCCTCGCCAC | TCTCTTCTGC | 780
| CAGCCCCACG | CCCGTGAATG | GCGCGTGTAA | CGACATGTTG | ATTTCATTAA | ACGTCAGCCA | 840
| TAACGCCACT | TTATGTTGGT | AGCGAGTAAA | GACCGTGCGG | GCGTAATGTT | CGAAGTGATC | 900
| GATGACCGCT | CGATTAGCCA | ACCGCCGTAG | TTTTTCACCA | GCCCATATGG | CATTTCGTAA | 960
| TGGGATAACG | TTACCAGCGG | CTTGATCCCC | GCCTGCGCCA | TTTCATCAAA | CAGCCGATCG | 1020
| TAAAACGCTA | ACCCCGCTTC | ATTCGGTTCG | ACTTCGTCGC | CCTGAGGGAA | AATTCGCGCC | 1080
| CAGGCAATGG | AAATACGCAG | ACAGGTGAAG | CCCATCTCGG | CAAATAACGC | GATATCTTCC | 1140
| GGGTAACGGT | GATAAAAATC | GATGGCGACA | TCTTTGATAT | TCTCTTTCCC | CAGGATGCGC | 1200
| GGTTCCATTT | TTCCCATTAC | GCATGAGGCT | GTAAATCTGA | GGTCAGATC | CCTTTGCCAT | 1260
| CTTCCTGCCA | GGCACCTTCC | ACCTGATTGG | CAGCTGTTGC | GGCACCCCAA | AGAAATGTTT | 1320
| CTGGAAATGC | TTTCATAATT | AACTCCTTTT | ATCGTTAGCG | AATGATGGAT | AACAGCGGTT | 1380
| CACCTGCGCT | TATCTGCGCC | GTGCCGTGGG | GTAATACGTC | CGTAAAATCA | TCGCTATTAC | 1440
| TGATTAATAC | CGGCGTCGTC | AGATCAAATC | CGGCCTCGCG | AATAGCAGGG | ATATCAAAAG | 1500
| AAATCAGCCG | ATCGCCTGTA | TTGACCTTGT | CACCCACGTT | GACGTGAGCG | GAAAAGAATT | 1560
| TGCCGTCCAG | TTTTACGGTG | TCGATACCGA | CATGAATCAG | GATCTCCACA | CCATCATCTG | 1620

| | | | | | | |
|---|---|---|---|---|---|---|
| ACTCAATGCC | AATGGCGTGT | AATGTGGCGA | ACAACGAAGC | AATTCGACCC | GCAACCGGAG | 1680 |
| AACGCACTTC | ACCAACCGAG | GGCAGAATGG | CAATACCTTT | ACCCAACAGG | CCACTGGCAA | 1740 |
| ACGTGGTATC | AGCGACGTGA | ATGAGCGACA | CAATCTCTCC | CGTCATCGGT | GAACAGATAC | 1800 |
| CGCCCTGCTC | AGGTGGTGTA | ATAACCTCTG | GTGTTTTCTC | TTCGGGGCAC | CCTGCGCTGG | 1860 |
| CTGACGTTTA | GCGGTGATGA | AATGAAGCAT | CACCGTACCG | ACAAATGCGC | AACCGATGGC | 1920 |
| AATGACACCG | CCAATAACGC | TGGCCCAGAC | GGTGAAATCA | ATTCCCGTTG | ACGGGATGGT | 1980 |
| TTGCATGAAG | GTGAAAATAC | TTGGCAAACC | AAAGGAGTAG | ACTTTCGTTT | GCGCGTAGCC | 2040 |
| AATAATGGTG | GCCCCCAAAG | CCCCACTGAT | ACAGGCGATA | ACAAGGGGT | ACTTACGCGG | 2100 |
| CAGGTTGACG | CCATATACCG | CTGGTTCGGT | GATACCAAAC | AGACTCGTCA | ACGCCGCTGA | 2160 |
| TCCCGCCACC | ACTTTTTTCT | GCGCATCGCG | TTCGCAGAGG | AAGACGCCGA | GCGCCGCCCC | 2220 |
| GACCTGCGCC | ATAATGGCGG | GCATTAACAG | CGGGATCATG | GTGTCGTAGC | CCAGCACGGT | 2280 |
| GAAGTTATTG | ATACACACCG | GCACCAGGCC | CCAGTGCAGT | CCGAACATGA | CGAAGATTTG | 2340 |
| CCAGAAGCCG | CCCATTACCG | CGCCCGCAAA | TGCAGGAACC | GCCTGATAAA | GCCAGAGATA | 2400 |
| ACCGGCGGCA | ATCAGTTCGC | TTATCCAGGT | TGATAGCGGC | CCCACCAGCA | GAAAGGTGAC | 2460 |
| GGGTGTGATA | ACCATCAGAC | ATAGCAATGG | TGTGAAGAAA | TTTTGATTG | CCGACGGTAA | 2520 |
| CCACGCATTA | AGTCGGCGTT | CCAGAATGCT | GCACAACCAG | GCAGAAAAAA | TAATGGGAAT | 2580 |
| AACCGATGAC | GAGTAATTCA | ACAATGTGAC | CGGAATACCC | AGGAAATCCA | GCCCCAGCGC | 2640 |
| ATCCGCTTTT | GCGCGTTCTC | GAAAAGCAGT | ACAGAATTAA | TGGATGCACT | AACGCTCCAC | 2700 |
| CAATCACCAT | GGCAGTAAAT | GGATTATCGC | CGAAGCGTTT | CCCCGCGGTG | TATCCCAGGA | 2760 |
| TTATCGGGAA | GAACCAAAAC | AAGGCATCAC | TGGCGCTGAA | TAAAATTAAA | TAAGTACCAC | 2820 |
| TTTGTTCGGG | CGTCCACTGA | AAAGTGAGCG | CCAGAGCCAG | CATACCTTTC | AAGATCCCCG | 2880 |
| GTTGCCCGCC | ATCAAACCGA | TACAGAGGCG | TAAAAATACC | TGAAATAACA | TAAACAAAGC | 2940 |
| GGTTTAGACA | GATTACCTTT | ATCATACATT | TTCCGGTGCC | TGTTGCGCTT | TTTCGTCAAG | 3000 |
| GCCTGCCACA | CTGTTAACCG | CCAGGAAGAC | ATCGGCCACA | TGGTTACCTA | TGACCACCTG | 3060 |
| AAACTGGCCA | CCGCTTTCCA | CCACCATAAT | AATACCGGGG | GTCTTTTTCA | GTACCTCTGC | 3120 |
| TTGCGCTTTG | CTTTCATCCT | TAATTTAAA | AACGTAAATC | GCGTTGCGCA | ATGCATCAGA | 3180 |
| CTCACAATGT | TATCTGCGCC | CCCGACTCCT | GCGACTATTT | TTCTGGCTAA | CTCCGTCATA | 3240 |
| ACTTGCCCTC | TACGCTTTGC | GGCAAAACTC | CAAAAAAAA | CCTGAAAAAA | ACGGCCTGAC | 3300 |
| GTGAATCAAG | CAATTTTTTT | CAGGTTTTGC | CCGCTTAGTG | CGGTAACAAT | CCTTTACTCA | 3360 |
| GTAATAATAT | TTCAGTGTTC | TTTGCGCACG | CGCTCTATAT | TTATGGCTAA | AAACATAATC | 3420 |
| TCTGCGGGTG | AAATTTTACG | TTGATACTGC | AAACCAATAA | AAATGGCGAT | CCGTTCCGCA | 3480 |
| CATTGCCATG | CTTGCGGGTA | ATTTTGTTTT | ACTGCTTGTT | GTAATGATTC | ATCACTATCG | 3540 |
| TTAATTGAAG | CATGTTCAAG | AATACGCCAG | GATAAAAACT | TCAGATGTGT | AACCAGTCGC | 3600 |
| TGATAACTCA | AGCTT | | | | | 3615 |

(2) INFORMATION FOR SEQ ID NO:18:

(i) SEQUENCE CHARACTERISTICS:
        (A) LENGTH: 4954 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:

(A) ORGANISM: Escherichia coli
(B) STRAIN: Clinical Isolate EC-34

(xi) SEQUENCE DESCRIPTION: SEQ ID NO:18:

```
AAGCTTAACC GCTCTCATCT GTTGACCGCA CGGCATAGCT ATATTCTGCC GGTCCTGGGA        60
CGTAGCGAGA TTGACATGCA AAAAAACGGT GCGCAGGCGG TAACCGTTGA GGATTCAATG       120
TCGATGATTC ATGCCTCGCG TGGCGTGTTA AAACCCGCCG GTGTAATGCT GAAATCAGAG       180
TGTGCAGTGG TCGCGGGAAT CGCGCAGGCA GCACTACCCC AGAGCGTGGT AGCCTGGGAG       240
TATCTGGTGG AAGATTATGA TCGCATTCGC AATGACATTG AAGCTGTGCT GCCAGAGTTC       300
GCCGACTATA ACCAGCGCAT CCGTCATCCC GGTGGTTTTC ACCTGATAAA TGCAGCTGCT       360
GAAAGGCGCT GGATGACGCC GTCAGGTAAG GCTAATTTCA TTACCAGCAA AGGGCTGTTA       420
GAAGATCCCT CTTCAGCGTT TAACAGTAAG CTGGTCATGG CGACAGTACG CAGCCACGAT       480
CAGTACAACA CGACGATTTA TGGTATGGAT GATCGCTATC GAGGGGTATT CGGTCAACGA       540
GATGTGGTCT TTATGAGTGC TAAACAAGCT AAAATTTGCC GTGTAAAAAA CGGCGAAAGA       600
GTTAATCTTA TTGCGCTTAC GCCAGACGGT AAGCGCAGTC ACGCCGCATG GATAGATTAA       660
AAGTGGTCAT TTACCCTATG GCTGACCGCT CACTGGTGAC CTATTTTCCA GAATCGAATC       720
ACATGCTAAC ACTTGATAAC CACGATCCAT TAAGTGGCAT TCCTGGCTAT AAAAGTATTC       780
CGCTTGAATT AGAACCATCA AATTAATGTC TCTTCTCATT TCTTCTGCTG TCATCCGCAC       840
AGCAGAAGAA TTCCTCATTG ACTATTATTT CGCAATTTGC TCACATGGAT TAAATTAAAC       900
TACATACTAT AAGATATAAA CTTCTGCCTA CAGCTGTAAG AAACTCCGCT CAGTACTGAA       960
GCACCAGTCC TATTTCCTCT TTTCTCCAGC CTGTTATATT AAGCATACTG ATTAACGATT      1020
TTTAACGTTA TCCGCTAAAT AAACATATTT GAAATGCATG CGACCACAGT GAAAAACAAA      1080
ATCACGCAAA GAGACAACTA TAAAGAAATC ATGTCTGCAA TTGTGGGTGT CTTATTACTG      1140
ACACTTACGT GATAGCCATT TTTTCGGCAA TTGATCAGCT GAGTATTTCA GAAATGGGTC      1200
GCATTGCAAG AGATCTTACA CATTTCATTA TCAATAGTTT GCAAGGCTGT AAACAAACAG      1260
CAAATTATAA ATATGAAATG TTAAAAAAGT ATCGATAAAA ACTTTATTGT TTTAAGGAGA      1320
TAAAATGTCG CTCGTTTGTT CTGTTATATT TATTCATCAT GCCTTCAACG CTAACATTTT      1380
AGATAAAGAT TACGCCTTCT CTGACGGCGA GATCCTGATG GTAGATAACG CTGTTCGTAC      1440
GCATTTTGAA CCTTATGAGC GGCATTTTAA AGAGATCGGA TTTACTGAAA ATACCATTAA      1500
AAAATATCTA CAATGCACTA ACATCCAGAC AGTGACGGTG CCTGTTCCTG CGAAGTTTTT      1560
ACGTGCTTCA AATGTACCGA CTGGATTGCT TAATGAAATG ATTGCTTATC TCAACTCGGA      1620
AGAACGCAAT CATCATAATT TTTCAGAACT TTTGCTTTTT TCTTGCCTGT CTATTTTTGC      1680
CGCATGCAAA GGTTTCATTA CACTATTAAC TAACGGTGTG CTATCCGTTT CTGGGAAAGT      1740
GAGAAATATT GTCAACATGA AGCCGGCGCA CCCATGGAAG CTGAAAGATA TTTGTGACTG      1800
CCTGTACATC AGTGAAAGCC TGTTGAAGAA AAACTTAAGC AAGAGCAAAC GACATTCTCA      1860
CAGATTCTTT TAGATGCAAG AATGCAGCAC GCAAAAAATT TGATACGCGT AGAAGGTTCA      1920
GTCAATAAAA TTGCCGAACA ATGTGGTTAT GCCAGTACAT CTTATTTTAT TTATGCGTTC      1980
CGCAAACATT TCGGCAACAG TCCGAAGAGA GTTTCTAAGG AGTACCGTTG TCAAAGTCAC      2040
ACGGGTATGA ATACGGGCAA CACGATGAAT GCTTTAGCTA TTTGATTATT TGCTAACGAG      2100
TAGTCAACCA CACACGCTGC GTAAGAATTA AATGGGGCAG CCATTCCCTG CCCCGCGTTG      2160
TTTTTAGGCG ATATATTTAT TGAAATAAAT AAGTGACATC CATCACATAT TTATGCACTT      2220
GCATAACCTG TTGCATGATT ATTTATGATC TCAATTCTGC ATTTTGTCAG TAAAATGCAA      2280
```

```
TAATTTATTA  AATATCAATA  AATTAGTTGT  TTATCGGCGA  GAAATTACTT  AATAGAACAG    2340

AAAGTAATGT  CAACGCTTTA  TGGACTGTTT  TTTCCCTTTT  TTTAGCTAAA  TCTGCTATCT    2400

CTTTATGTGA  CTAACTTCAC  TTACATCCAC  TTATTTCTCT  TCGTAAAATT  ACTTTGGAAT    2460

TAAGTACAAT  AAGAAGAGGA  ACATTTATGA  AGTCTGCATT  AAAGAAAAGT  GTCGTAAGTA    2520

CCTCGATATC  TTTGATACTG  GCATCTGGTA  TGGCTGCATT  TGCTGCTCAT  GCGGCAGATG    2580

ATGTAAAGCT  GAAAGCAACC  AAAACAAACG  TTGCTTTCTC  AGACTTTACG  CCGACAGAAT    2640

ACAGTACCAA  AGGAAAGCCA  AATATTATCG  TACTGACCAT  GGATGATCTT  GGTTATGGAC    2700

AACTTCCTTT  TGATAAGGGA  TCTTTTGACC  CAAAAACAAT  GGAAAATCGT  GAAGTTGTCG    2760

ATACCTACAA  AATAGGGATA  GATAAAGCCA  TTGAAGCTGC  ACAAAAATCA  ACGCCGACGC    2820

TCCTTTCATT  AATGGATGAA  GGCGTACGTT  TTACTAACGG  CTATGTGGCA  CACGGTGTTT    2880

CCGGCCCCTC  CCGCGCCGCA  ATAATGACCG  GTCGAGCTCC  CGCCCGCTTT  GGTGTCTATT    2940

CCAATACCGA  TGCTCAGGAT  GGTATTCCGC  TAACAGAAAC  TTTCTTGCCT  GAATTATTCC    3000

AGAATCATGG  TTATTACACT  GCAGCAGTAG  GTAAATGGCA  CTTGTCAAAA  ATCAGTAATG    3060

TGCCGGTACC  GGAAGATAAA  CAAACGCGTG  ACTATCATGA  CACCTTCACC  ACATTTTCTG    3120

CGGAAGAATG  GCAACCTCAA  AACCGTGGCT  TTGATTACTT  TATGGGATTC  CACGCTGCAG    3180

GAACGGCATA  TTACAACTCC  CCTTCACTGT  TCAAAAATCG  TGAACGTGTC  CCCGCAAAAG    3240

GTTATATCAG  CGATCAGTTA  ACCGATGAGG  CAATTGGCGT  TGTTGATCGT  GCCAAAACAC    3300

TTGACCAGCC  TTTTATGCTT  TACCTGGCTT  ATAATGCTCC  GCACCTGCCA  AATGATAATC    3360

CTGCACCGGA  TCAATATCAG  AAGCAATTTA  ATACCGGTAG  TCAAACAGCA  GATAACTACT    3420

ACGCTTCCGT  TTATTCTGTT  GATCAGGGTG  TAAAACGCAT  TCTCGAACAA  CTGAAGAAAA    3480

ACGGACAGTA  TGACAATACA  ATTATTCTCT  TTACCTCCGA  TAATGGTGCG  GTTATCGATG    3540

GTCCTCTGCC  GCTGAACGGG  GCGCAAAAAG  GCTATAAGAG  TCAGACCTAT  CCTGGCGGTA    3600

CTCACACCCC  AATGTTTATG  TGGTGGAGAA  GGAAAACTTC  AACCCGGTAA  TTATGACAAG    3660

CTGATTTCCG  CAATGGATTT  CTACCCGACA  GCTCTTGATG  CAGCCGATAT  CAGCATTCCA    3720

AAAGACCTTA  AGCTGGATGG  CGTTTCCTTG  CTGCCCTGGT  TGCAAGATAA  GAAACAAGGC    3780

GAGCCACATA  AAAATCTGAC  CTGGATAACC  TCTTATTCTC  ACTGGTTTGA  CGAGGAAAAT    3840

ATTCCATTCT  GGGATAATTA  CCACAAATTT  GTTCGCCATA  CAGTCAGACG  ATTACCCGCA    3900

TAACCCCAAC  ACTGAGGACT  TAAGCCAATT  CTCTTATACG  GTGAGAAATA  ACGATTATTC    3960

GCTTGTCTAT  ACAGTAGAAA  ACAATCAGTT  AGGTCTCTAC  AAACTGACGG  ATCTACAGCA    4020

AAAAGATAAC  CTTGCCGCCG  CCAATCCGCA  GGTCGTTATA  GAGATGCAAG  GCGTGGTAAG    4080

AGAGTTTATC  GACAGCAGCC  AGCCACCGCT  TAGCGAGGTA  AATCAGGAGA  AGTTTAACAA    4140

TATCAAGAAA  GCACTAAGCG  AAGCGAAATA  ACTAAACCTT  CATGCGGCGG  ATTTTCCGC    4200

CGCCTTATTG  AGCGAGATAG  CGATGCACGT  TACAGCCAAG  CCCTCCAGTT  TTCAATGTAA    4260

TCTCAAATGT  GATTACTGTT  TTTACCTTGA  AAAAGAGTCG  CAGTTACTC  ATGAAAAATG    4320

GATGGATGAC  AGCACTTTGA  AAGAGTTCAT  CAAACAATAT  ATCGCAGCGT  CTGGCAATCA    4380

GGTCTATTTT  ACCTGGCAAG  GCGGTGAACC  CACTCTGGCT  GGCCTGGATT  TTTTCCGTAA    4440

AGTTATTCAC  TATCAACAAC  GCTATGCAGG  CCAAAAACGT  ATTTTTAATG  CATTACAAAC    4500

GAATGGCATT  TTATTGAATA  ATGAATGGTG  TGCCTTCTCA  AGAACATGA  ATTTCTGGTG    4560

GTATCTCGAT  CGATGGCCCC  CAGGAGTTAC  ATGACCGTTA  CAGACGCAGT  AATTCAGGTA    4620

ACGGTACTTT  TGCAAAAGTG  ATAGCAGCCA  TCGAGCGTCT  GAAATCATAT  CAAGTAGAGT    4680
```

```
TTAATACGTT  AACCGTCATT  AATAACGTTA  ATGTCCATTA  CCCTCTTGAG  GTTTATCATT      4740

TTTTAAAATC  TATCGGCAGT  AAACATATGC  AATTTATCGA  ATTGCTAGAA  ACCGGGACGC      4800

CGAATATTGA  TTTCAGTGGT  CATAGTGAGA  ACACATTCCG  TATCATTGAT  TTTTCTGTGC      4860

CTCCCACGGC  TTATGGCAAG  TTTATGTCAA  CCATTTTTAT  GCAATGGGTT  AAAAACGATG      4920

TGGGTGAAAT  TTTCATCCGT  CAGTTTGAAA  GCTT                                    4954
```

(2) INFORMATION FOR SEQ ID NO:19:

(i) SEQUENCE CHARACTERISTICS:
        (A) LENGTH: 3796 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Escherichia coli
        (B) STRAIN: Clinical Isolate EC- 39

(xi) SEQUENCE DESCRIPTION: SEQ ID NO:19:

```
AAGCTTAATC  GCGTGAATCA  GGAGTAAAAA  AATGACAACC  CAGACTGTCT  CTGGTCGCCG        60

TTATTTCACG  AAAGCGTGGC  TGATGGAGCA  GAAATCGCTT  ATCGCTCTGC  TGGTGCTGAT       120

CGCGATTGTC  TCGACGTTAA  GCCCGAACTT  TTTCACCATC  AATAACTTAT  TCAATATTCT       180

CCAGCAAACC  TCAGTGAACG  CCATTATGGC  GGTCGGGATG  ACGCTGGTGA  TCCTGACGTC       240

GGGCATCGAC  TTATCGGTAG  GTTCTCTGTT  GGCGCTGACC  GGCGCAGTTG  CTGCATCTAT       300

CGTCGGCATT  GAAGTCAATG  CGCTGGTGGC  TGTCGCTGCT  GCTCTCGCGT  TAGGTGCGCA       360

ATTGGTGCGG  TAACCGGGGT  GATTGTAGCG  AAAGGTCGCG  TCCAGGCGTT  TATCGCTACG       420

CTGGTTATGA  TGCTTTTACT  GCGCGGCGTG  ACCATGGTTT  ATACCAACGG  TAGCCCAGTG       480

AATACCGGCT  TTACTGAGAA  CGCCGATCTG  TTTGGCTGGT  TTGGTATTGG  TCGTCCGCTG       540

GGCGTACCGA  CGCCAGTCTG  GATCATGGGG  ATTGTCTTCC  TCGCGGCCTG  GTACATGCTG       600

CATCACACGC  GTCTGGGGCG  TTACATCTAC  GCGCTGGGCG  ACAACGAAGC  GACAACGCGT       660

CTTTCTGGTA  TCAACGTCAA  TAAAATCAAA  ATCATCGTCT  ATTCTCTTTG  TGGTCTGCTG       720

GCATCGCTGG  CGGGATCATA  GAAGTGGCGC  GTCTCTCCTC  CGCACAACCA  CGGCGGGGAC       780

TGGCTATGAG  CTGGATGCTA  TTGCTGCGGT  GGTTCTGGGC  GGTACGAGTC  TGGCGGGCGG       840

AAAAGGTCGC  ATTGTTGGGA  CGTTGATCGG  CGCATTAATT  CTTGGCTTCC  TTAATAATGG       900

ATTGAATTTG  TTAGGTGTTT  CCTCCTATTA  CCAGATGATC  GTCAAAGCGG  TGGTGATTTT       960

GCTGGCGGTG  CTGGTAGACA  ACAAAAAGCA  GTAATAACGA  CTACAGGCAC  ATCTTGAATA      1020

TGAACATGAA  AAAACTGGCT  ACCCTGGTTT  CCGCTGTTGC  GCTAAGCGCC  ACCGTCAGTG      1080

CGAATGCGAT  GGCAAAAGAC  ACCATCGCGC  TGGTGGTCTC  CACGCTTAAC  AACCCGTTCT      1140

TTGTATCGCT  GAAAGATGGC  GCGCAGAAAG  AGGCGGATAA  ACTTGGCTAT  AACCTGGTGC      1200

TGGACTCCCA  GAACAACCCG  GCGAAAGAGC  TGGCGAACGT  GCAGGACTTA  ACCGTTCGCG      1260

GCACAAAAAT  TCTGCTGATT  AACCCGACCG  ACTCCGACGC  AGTGGGTAAT  GCTGTGAAGA      1320

TGGCTAACCA  GGCGAACATC  CCGGTTATCA  CTCTTGACCG  CCAGGCAACG  AAAGGTGAAG      1380

TGGTGAGCCA  CATTGCTTCT  GATAACGTAC  TGGGCGGCAA  AATCGCTGGT  GATTACATCG      1440

CGAAGAAAGC  GGGTGAAGGT  GCCAAAGTTA  TCGAGCTGCA  AGGCATTGCT  GGTACATCCG      1500

CAGCCCGTGA  ACGTGGCGAA  GGCTTCCAGC  AGGCCGTTGC  TGCTCACAAG  TTTAATGTTC      1560
```

-continued

| | | | | | | |
|---|---|---|---|---|---|---|
| TTGCCAGCCA | GCCAGCAGAT | TTTGATCGCA | TTAAAGGTTT | GAACGTAATG | CAGAACCTGT | 1620 |
| TGACCGCTCA | TCCGGATGTT | CAGGCTGTAT | TCGCGCAGAA | TGATGAAATG | GCGCTGGGCG | 1680 |
| CGCTGCGCGC | ACTGCAAACT | GCCGGTAAAT | CGGATGTGAT | GGTCGTCGGA | TTTGACGGTA | 1740 |
| CACCGGATGG | CGAAAAAGCG | GTGAATGATG | GCAAACTAGC | AGCGACTATC | GCTCAGCTAC | 1800 |
| CCGATCAGAT | TGGCGCGAAA | GGCGTCGAAA | CCGCAGATAA | AGTGCTGAAA | GGCGAGAAAG | 1860 |
| TTCAGGCTAA | GTATCCGGTT | GATCTGAAAC | TGGTTGTTAA | GCAGTAGTTT | TAATCAGGTT | 1920 |
| GTATGACCTG | ATGGTGACAT | AAATACGTCA | TCGACAGATG | AACGTGTAAT | ATAAAGAAAA | 1980 |
| GCAGGGCACG | CGCCACCCTA | ACACGGTGGC | GCATTTTATG | GACATCCCGA | ATATGCAAAA | 2040 |
| CGCAGGCAGC | CTCGTTGTTC | TTGGCAGCAT | TAATGCTGAC | CACATTCTTA | ATCTTCAATC | 2100 |
| TTTTCCTACT | CCAGGCGAAA | CGTAACCGGT | AACCACTATC | AGGTTGCATT | TGGCGGCAAA | 2160 |
| GGCGCGAATC | AGGCTGTGGC | TGCTGGGCGT | AGCGGTGCGA | ATATCGCGTT | TATTGCCTGT | 2220 |
| ACGGGTGATG | ACAGCATTGG | TGAGAGCGTT | CGCCAGCAGC | TCGCCACTGA | TAACATTGAT | 2280 |
| ATTACTCCGG | TCAGCGTGAT | CAAAGGCGAA | TCAACAGGTG | TGGCGCTGAT | TTTTGTTAAT | 2340 |
| GGCGAAGGTG | AGAATGTCAT | CGGTATTCAT | GCCGGCGCTA | ATGCTGCCCT | TTCCCCGGCG | 2400 |
| CTGGTGGAAG | CGCAACGTGA | GCGTATTGCC | AACGCGTCAG | CATTATTAAT | GCAGCTGGAA | 2460 |
| TCACCACTCG | AAAGTGTGAT | GGCAGCGGCG | AAAATCGCCC | ATCAAAATAA | AAACTATCGT | 2520 |
| TCGCTTAACC | CGCTCCGGCT | CGCGAACTTC | CTGACGAACT | CTGCGCTGTG | GACATTATTA | 2580 |
| CGCCAAACGA | AACGGAAGCA | GAAAAGCTCA | CCGGTATTCG | TGTTGAAAAT | GATGAAGATG | 2640 |
| CAGCGAAGGC | GGCGCAGGTA | CTTCATGAAA | AAGGTATCCG | TACTGTACTG | ATTACTTTAG | 2700 |
| GAAGTCGTGG | TGTATGGGCT | AGCGTGAATG | GTGAAGGTCA | GCGCGTTCCT | GGATTCCGGG | 2760 |
| TGCAGGCTGT | CGATACCATT | GCTGCCGGAG | ATACCTTTAA | CGGTGCGTTA | ATCACGGCAT | 2820 |
| TGCTGGAAGA | AAAACCATTG | CCAGAGGCGA | TTCGTTTTGC | CCATGCTGCC | GCTGCGATTG | 2880 |
| CCGTAACACG | TAAAGGCGCA | CAACCTTCCG | TACCGTGGCG | TGAAGAGATC | GACGCATTTT | 2940 |
| TAGACAGGCA | GAGGTGACGC | TTGGCTACAA | TGAAAGATGT | TGCCCGCCTG | GCGGGCGTTT | 3000 |
| CTACCTCAAC | AGTTTCTCAC | GTTATCAATA | AGATCGCTT | CGTCAGTGAA | GCGATTACCG | 3060 |
| CAAAGTGAGC | GCGATTAAAG | ACTCAATTAC | GCGCCATCAG | CTCTGGCGCG | TAGCCTCAAA | 3120 |
| CTCAATCAAA | CACATACCAT | TGGCATGTTG | ATCACTGCCA | GTACCAATCC | TTTCTATTCA | 3180 |
| GAACTGGTGC | GTGTCGTTGA | ACGCAGCTGC | TTCAACGCG | GTTATAGTCT | CGTCCTTTGC | 3240 |
| AATACCGAAG | GCGATGAACA | GCGGATGAAT | CGCAATCTGG | AAACGCTGAT | GCAAAACGC | 3300 |
| GTTGATGGCT | TGCTGTTACT | GTGCACCGAA | ACGCATCAAC | CTTCGCGTGA | AATCATGCAA | 3360 |
| CGTTATCCGA | CAGTGCCTAC | TGTGATGATG | GACTGGGCTC | CGTTCGATGG | CGACAGCGAT | 3420 |
| CTTATTCAGG | ATAACTCGTT | GCTGGGCGGA | GACTTAGCAA | CGCAATATCT | GATCGATAAA | 3480 |
| GGTCATACCC | GTATCGCCTG | TATTACCGGC | CCGCTGGATA | AAACTCCGGC | GCGCTGCGGT | 3540 |
| TGGAAGGTTA | TCGGGCGGCG | ATGAAACGTG | CGGGTCTCAA | CATTCCTGAT | GGCTATGAAG | 3600 |
| TCACTGGTGA | TTTTGAATTT | AACGGCGGGT | TTGACGCTAT | GCGCCAACTG | CTATCACATC | 3660 |
| CGCTGCGTCC | TCAGGCCGTC | TTTACCGGAA | ATGACGCTAT | GGCTGTTGGC | GTTTACCAGG | 3720 |
| CGTTATATCA | GGCAGAGTTA | CAGGTTCCGC | AGGATATCGC | GGTGATTGGC | TATGACGATA | 3780 |
| TCGAACTGGC | AAGCTT | | | | | 3796 |

(2) INFORMATION FOR SEQ ID NO:20:

(i) SEQUENCE CHARACTERISTICS:

(A) LENGTH: 5541 base pairs
(B) TYPE: nucleic acid
(C) STRANDEDNESS: double
(D) TOPOLOGY: linear (i i) MOLECULE TYPE: Genomic DNA (v i) ORIGINAL SOURCE:
(A) ORGANISM: Escherichia coli
(B) STRAIN: Clinical Isolate EC- 625

(x i) SEQUENCE DESCRIPTION: SEQ ID NO:20:

| | | | | | | |
|---|---|---|---|---|---|---|
| AAGCTTAAGC | CTGCATTTGC | TCAATGAAGC | GCAGAATGAG | CTGGAACTGT | CAGAAGGCAG | 60 |
| CGACGATAAC | GAAGGTATTA | AGAACGTAC | CAGCTTCCGT | CTGGAGCGTC | GGGTCGCCGG | 120 |
| AGTGGGTCGT | CAAATGGGCC | GCGGTAACGG | CTATCTGGCA | ACCATCGGCG | CGATTTCTCC | 180 |
| GTTCGTTGGT | CTGTTTGGTA | CGGTCTGGGG | CATCATGAAC | AGCTTTATTG | GTATCGCGCA | 240 |
| AACGCAGACC | ACTAACCTGG | CAGTCGTTGC | GCCGGGTATC | GCAGAAGCTC | TGTTAGCAAC | 300 |
| GGCAATCGGC | CTCGTGGCAG | CGATTCCTGC | GGTCGTTATC | TATAACGTAT | TTGCACGCCA | 360 |
| GATTGGCGGC | TTTAAAGCGA | TGCTGGGTGA | TGTTGCAGCG | CAGGTATTGT | TGCTGCAAAG | 420 |
| CCGTGACCTG | GATCTGGAAG | CCAGCGCCGC | TGCGCATCCG | GTTCGTGTCG | CACAAAAATT | 480 |
| ACGCGCAGGA | TAATATCCGA | TGGCAATGCA | TCTTAACGAA | AACCTCGACG | ATAACGGCGA | 540 |
| AATGCATGAT | ATCAACGTGA | CGGCGTTTAT | CGACGTGATG | TTGGTTCTGC | TGATTATCTT | 600 |
| TATGGTGGCG | GCACCGTTAG | CGACGGTAGA | TGTGAAGGTG | AACTTGCCTG | CTTCTACCAG | 660 |
| CACGCCGCAG | CCGCGGCCGG | AAAAACCGGT | TTATCTGTCG | GTGAAGGCAG | ACAACTCGAT | 720 |
| GTTTATCGGT | AACGATCCGG | TCACCGATGA | AACAATGATT | ACGGCGTTGA | ATGCGTTAAC | 780 |
| CGAAGGCAAG | AAAGACACCA | CCATCTTCTT | CCGAGCGGAT | AAAACCGTCG | ATTACGAGAC | 840 |
| GTTGATGAAG | GTAATGGATA | CGCTGCATCA | GGCGGGTTAC | CTGAAGATAG | GTCTGGTCGG | 900 |
| CGAAGAAACC | GCCAAAGCGA | AGTAAAGTAG | AATTGCCTGA | TGCGCTACGC | TCATCAGGCC | 960 |
| TACAAAATCT | ATTGCAACAT | GTTGAATCTT | CGTGCGTTTG | TAGGCCGGAT | AAGGCGTTCA | 1020 |
| CGCGCATCCG | GCATTAGGTG | CTCAATGCCT | GATGCGCTAC | GTTTATCAGG | CCTACAAAAT | 1080 |
| CTATTGCAAC | ATGTTGAATC | TTCATGCGTT | TGTAGGCGGA | TAAGGCGTTT | CGCACATCA | 1140 |
| GGTAAGAGTG | AATTCACAAT | GATGCCCGGT | TGCTTTTCAC | AACCGGGCAT | TTTTTTAACC | 1200 |
| TAAATGCTCG | CCGCCGCACA | CACCGTGCAC | TTCTGCGGTG | ACGTAGCTCG | ACTCCTGACT | 1260 |
| TGCCAGATAA | ACATATACTG | GGGCCAGTTC | CGCCGGTTGC | CCCGCACGCT | TCATCGGCGT | 1320 |
| TTTCTGACCA | AACTGCGGGA | TCTTATCCTG | CGTTTGTCCG | CCGGAAATTT | GCAGTGCCGT | 1380 |
| CCAGATAGGG | CCTGGCGCGA | CAATATTCAC | CCGAATACCT | TTCTCCGCGA | CCTGTTTTGC | 1440 |
| CAGGCCACGG | CTGTAGTTCA | GAATCGCCGC | CTTCGTAGCC | GCATAGTCCA | GTAAATGCGG | 1500 |
| ACTTGGCTGG | TATGCCTGGA | TTGACGAAGT | GGTGATAATA | CTTGCACCTT | TCGGTAGCAG | 1560 |
| GGGGATCGCT | TCCTGGGTTA | GCCAGAACAG | CGCGAAAACG | TTAATGGCAA | AGGTCTTTTG | 1620 |
| AAACTGTTCG | CTGGTGAGGT | CTGCAATATC | AGGAATGGCA | ACCTGTTTCC | CGGCGACCAG | 1680 |
| CGCCATAATA | TCCAGCCCGC | CTAACGCCTT | GTGCGCTTCG | TGAACCAGCG | AACGGGCGAA | 1740 |
| TTTCTCATCG | CTTAAATCGC | CTGGCAGCAG | AACGGCTTTG | CGTCCGCATT | CTTCAATGAT | 1800 |
| CTTTTTCACA | TCCTGAGCGT | CTTCTTCTTC | CACGGGAAGA | TAACTGATCG | CCACGTCAGC | 1860 |
| CCCTTCACAC | GCGTAAGATG | GCGGCAGCGC | GACCGATTCC | GGAATCGCCC | CCTGTCACCA | 1920 |
| GTGCTTTACG | ATCTTTCAGG | CGACCGCTAC | CAACATAGGT | TTTCTCGCCG | CAATCCGGTA | 1980 |
| CCGGTGTCAT | CTTCGCCTGG | ATGCCTGGCG | TCGGTTGTTT | CTGTTTGGGA | TATTCACCAG | 2040 |

```
TGTAATACTG  CGTGGTCGGG  TCTTTTAAAT  GAGACATCGT  TTTTCTCCCT  TCAGGTTCAA   2100
CGTCCTTTAA  GGGTAGACGC  TCTCGATGCG  TTGATAAGGG  AACCAGGAAG  ATCCCTAACC   2160
CTCAGAATTA  TGCGACAAAG  GTTAACGGA   TATGTTGATT  TGCTGTTGCG  CGCTGTTTAC   2220
TCAATTGCGA  TATACTGTTG  CCCGTTTTAA  CTACACGACA  GGAATGTATG  GAACGTTTTC   2280
TTGAAAATGC  AATGTATGCT  TCTCGCTGGC  TGCTTGCCCC  CGTGTACTTT  GGCCTTTCGC   2340
TGGCGTTAGT  TGCCCTGGCG  CTGAAGTTCT  TCCAGGAGAT  TATTCACGTA  CTGCCGAATA   2400
TCTTCTCGAT  GGCGGAATCA  GATTGATCC   TCGTGTTGCT  GTCGCTGGTG  GATATGACAC   2460
TGGTTGGCGG  TTTACTGGTG  ATGGTGATGT  TTTCCGGTTA  TGAGAATTTC  GTCTCGCAGC   2520
TGGATATCTC  CGAGAACAAA  GAGAAGCTGA  ACTGGCTGGG  GAAAATGGAC  GCAACGTCGC   2580
TGAAAAACAA  AGTAGCAGCG  TCGATTGTGG  CAATTTCTTC  CATTCACTTA  CTGCGCGTCT   2640
TTATGGATGC  GAAAAATGTC  CCTGATAACA  AACTGATGTG  GTACGTCATT  ATCCATCTGA   2700
CGTTTGTGCT  CTCTGCATTT  GTGATGGGCT  ATCTTGACCG  ACTGACTCGT  CATAATCACT   2760
GATCTTATGC  GGGCGCGGTT  CTCGCGCCCG  TTATTAACAG  GTCATTTATC  GGAAGACGCC   2820
TGCCACAGAT  TCAGCTCGCC  ATCGGCGATA  TGCTGATCAA  TCTGCGCCAG  CTCCTCGGTG   2880
CTAAATGTCA  GATTATTCAG  CGCCTGCACG  TTCTCCTCAA  GTTGTCCGCG  CGGCTGGCAC   2940
CAATCAATAC  CGACGTCACG  CGATCATCTT  TCAGCAACCA  GCTTAACGCC  ATTTGCGCCA   3000
TTGATTGTCC  ACGCTGCTGT  GCCATTTCAT  TCAATAAGTG  TAGGCTGTTG  AGGTTGGCTT   3060
CGGTAAGCAT  TTTCGGCGTC  AGACCACGAA  CTTTATTCCC  TTCACGATGC  ATCCGTGAAT   3120
CTTGCGGAAT  GCCGTTGAGA  TATTTTCCGG  TCAGCAATCC  CTGAGCCAGA  GGAGTAAAGG   3180
CAATACAGCC  CACGCCGTTA  TTTTGCAGGG  TATCCAGCAG  GCCGCTTTTA  TCCACCCAGC   3240
GGTTCAGTAA  ATTGTACGAA  GGTTGATGAA  TTAACAGCGG  AATTTTCCAC  TCGCGCAGCA   3300
ACTCAACCAT  TTTTTGCGTC  CGCTCTGGCG  AGTAAGAGGA  GATCCCGACA  TAAAGCGCCT   3360
TACCGCTTTG  TACCGCATGA  GCCAGCGCAG  AGGCGGTTTC  TTCCATCGGC  GTATTTTCAT   3420
CGACGCGATG  AGAGTAAAAG  ATATCGACAT  ACTCAAGCCC  CATACGCTTC  AGGCTTTGGT   3480
CGAGGCTGGA  GAGCAGGTAT  TTACGTGAAC  CGCCAGAGCC  GTAAGGGCCG  GCCACATAT    3540
CGTAGCCAGC  CTTGGTAGAG  ATAATCAGTT  CATCGCGATA  AGCGGCAAAA  TCCTCCCGCA   3600
GCAGGCGACC  AAAGTTCTCT  TCTGCGCTTC  CTGGAGGCGG  CCCGTAATTG  TTGGCTAAAT   3660
CAAAGTGCGT  AATGCCTAAA  TCAAACGCTT  TACGCAGGAT  TGCACGCTGT  GATTCCAGCG   3720
CGTTAACGTG  ACCGAAATTG  TGCCATAAAC  CGAGCGATAA  CGCGGGCAGG  CGTAAACCAC   3780
TTTTTCCGCA  ATAGCGGTAC  TGCATCTGCC  CGTAACGTTC  GGGTTCGCTA  ACCAGACCAT   3840
GACCTCTCCT  TTCCACCGTT  CAATTTCGAA  ACAATGTTTC  TAGTTTAGCG  ATTCGCCAGC   3900
GCGTATCCCG  TAGTCTGGCT  CACAGAGTGA  CGAAAAATTG  GCAAAAACAC  GCGCTTATGC   3960
TTTGCTTAAA  AAAACACCAG  TTGAGGAGTG  CAACGATGCC  GCGTTTAACC  GCCAAAGATT   4020
TCCCACAAGA  GTTGTTGGAT  TACTACGACT  ATTACGCTCA  CGGGAAAATC  TCGAAACGTG   4080
AGTTCCTCAA  TCTTGCGGCG  AAGTATGCGG  TGGGCGGGAT  GACGGCATTA  GCGTTGTTTG   4140
ATTTGCTCAA  GCCAAATTAT  GCGCTGGCGA  CTCAGGTAGA  GTTTACCGAC  CTGGAGATTG   4200
TTGCTGAGTA  CATCACGTAT  CCTTCGCCAA  ATGGTCACGG  CGAGGTACGG  GGTTATCTGG   4260
TGAAACCCGC  AAAAATGAGC  GGCAAAACGC  CAACCGTGGT  GGTGGTGCAT  GAGAATCGTG   4320
GACTGAATCC  GTATATCGAA  GATGTGGCAC  GGCGAGTGGC  GAAGGCGGGG  TATATCGCCC   4380
TGGCACCTGA  CGGCTTAAGT  TCCGTTGGAG  GTTATCCGGG  AAATGATGAT  AAAGGTCGTG   4440
```

| | | | | | | |
|---|---|---|---|---|---|---|
| AGCTGCAACA | GACAGGTTGA | TCCAACCAAA | CTGATGAATG | ATTTCTTTGC | CGCAATTGAG | 4500 |
| TTTATGCAAC | GCTATCCGCA | AGCGACAGGC | AAAGTGGGTA | TTACCGGATT | TTGCTATGGC | 4560 |
| GGTGGCGTAT | CGAACGCGGC | GGCTGTCGCG | TATCCGGAAC | TGGCCTGCGC | GGTGCCGTTT | 4620 |
| TATGGTCGTC | AGGCACCCAC | TGCCGATGTG | GCGAAGATTG | AAGCGCCTTT | ACTACTCCAC | 4680 |
| TTCGCGGAAC | TGGACACCCG | AATCAACGAG | GGCTGGCCTG | CTTACGAGGC | GGCGTTGAAA | 4740 |
| GCCAATAATA | AGGTTTATGA | GGCGTATATC | TATCCGGGGG | TTAATCACGG | ATTCCATAAT | 4800 |
| GATTCCACGC | CCCGTTATGA | CAAATCTGCC | GCCGATCTTT | CCTGGCAAAG | GACACTGAAA | 4860 |
| TGGTTCGATA | AATATCTCTC | CTGATAGGTT | TATCTCTTAC | GGGATTACGT | CTTAAACAAG | 4920 |
| CATGAAAAAA | TAGCGTGCGC | AAAAGTCGTT | CTTTGCCTAA | AATATCGCTA | TATATAACAA | 4980 |
| TATATAGCGA | ATGAGGTGAA | CGATGAATAA | CCATTTTGGT | AAAGGCTTAA | TGGCGGGATT | 5040 |
| AAAAGCAACG | CATGCCGACA | GTGCGGTTAA | TGTGACAAAA | TACTGTGCCG | ATTATAAACG | 5100 |
| CGGTTTTGTA | TTAGGCTACT | CACACCGGAT | GTACGAAAAG | ACCGGAGATC | GCCAGCTTAG | 5160 |
| CGCCTGGGAA | GCGGGTATTC | TGACGCGCCG | CTATGGACTG | GATAAAGAGA | TGGTAATGGA | 5220 |
| TTTCTTTCGT | GAGAATAATT | CCTGTTCTAC | GTTGCGCTTT | TTTATGGCCG | GTTATCGCCT | 5280 |
| CGAAAATTGA | TCAAACATAC | GTATTATCTT | GCTTTAATTA | ATTACACTAA | TGCTTCTTCC | 5340 |
| CTTCGTTTTA | GCGCCCCGCC | GCAGTATCAT | GATATCGATA | ACCATAATAA | ATGTGTGGTA | 5400 |
| AATGGCGCAT | CGATCGCATT | ATTGATTTTG | CGATTGAGGC | AAAATATATG | CCAGGTCTTC | 5460 |
| GCAACGGAAT | AACTATAAAT | GACTGGAGAT | AACACCCTCA | TCCATTCTCA | CGGCATTAAC | 5520 |
| CGTCGTGATT | TCATGAAGCT | T | | | | 5541 |

( 2 ) INFORMATION FOR SEQ ID NO:21:

( i ) SEQUENCE CHARACTERISTICS:
        ( A ) LENGTH: 6317 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Enterobacter cloacae
        ( B ) STRAIN: Clinical Isolate ET- 12

( x i ) SEQUENCE DESCRIPTION: SEQ ID NO:21:

| | | | | | | |
|---|---|---|---|---|---|---|
| AAGCTTGCCC | GCATCATTCA | GGAGCAGGGG | CGTCGCGACC | AGTTAGGTGT | GAAGTTTGGC | 60 |
| AGCGGTGACA | GCCCGGACTG | CCGGGGGATC | ACGGTTCCGG | AACTGCAGAG | TATCGACTTC | 120 |
| GACAAAATCA | ACTTCTCTGA | CTTCTACGAG | GATTTGATGA | AGAACCAGAA | AATCCCCGAT | 180 |
| ACCAGCGCGC | AGGTCAAGCA | GATTAAGGAT | CGCATCGCCG | CGCAGGTGAA | CCAGCAGGGA | 240 |
| GGTGGCAAAT | GAAGCGTGTC | CTCTGTGGCC | TGCTTATGGC | GCTGGCGAGC | CATACGGCAC | 300 |
| TGGCCGATGA | GATTGTGACG | CCGGCTGAGC | CGTTCACCGG | CTGGTCCTGG | TACAACGAAC | 360 |
| CGAAAAAGCC | CCCTGAGCAG | CCCCGGAAAC | CGCAGCAGCC | AGCACCGCAG | CCATTCCGGA | 420 |
| TCTCAGCAAA | ATGTCCCCGA | TGGAGCAGGC | CAGGGTGCTG | AAAGGGTATA | CACAGGAGGC | 480 |
| GCTTAACCGC | GCCATCCTGT | ACCCCTCAAG | GGAAAACACG | GCGACGTTCC | TGCGCTGGCA | 540 |
| GAAGTTCTGG | ACGGACCGGG | CATCGATGTT | CAGCCAGTCC | TTTGCGGCGG | CGCAGCTGAG | 600 |
| CCATCCGGAC | CTCGACTACA | ACCTGGAGTA | TCCGCACTAC | AACAGCATGG | CGCCGTTTAT | 660 |
| GCAGACCCGT | GACCAGCAGA | CGCGGCAGAG | CGCCGTGGAG | CAGCTTGCGC | AGAGTACGGT | 720 |

```
CTGTTCTACT TCTACCGGGG CAGTGACCCG ATTGATGTGC AGATGGCGGG CGTGGTGGCT    780
GACTTTGCGA AAACCAACGG GATCTCACTC ATTCCGGTCT CGGTTGACGG ACAGGTGGCG    840
GCCACCCTGC CGCAAAGCCG TCCGGACACC GGACAGTCCC GGTCGATGAA TATCACGCAC    900
TTTCCGGCGC TCTTCCTGGT TGACCCGCGC AACCAGAACT ACCGTGCCCT GTCCTATGGC    960
TTCATGACCC AGGATGACCT GTCAAAACGA TTCCTGAACG TGGCCACCGG CTTTAAACCC   1020
AATTCCTGAG AGCCTTTTAT GACAAAAACA CTGTTTACCT CATCCGCGAT GCAGGGCGGG   1080
CTGCCCTGTA TTCCTTCGTC CTCGGCCCGG CACTGGTGCT GTATGTGTTT GTGATGCTGG   1140
CGGCATCAGA CGGCTCACTT TCCCGGCAAT TCCTGACGAC CTTTCATCAC CTGACTGAGG   1200
GTGCGCCTGC CGGCAAGGTG ATGGGATGTG TTAATGAACA TGAGATGGCA GGGCGTTTCT   1260
CGCCACCTGA ACCCGGAGAG TCGTTAAAGC CCGTGCCTTC CGTTTTAGAT AAAGCACCGC   1320
CTGAAGTGTT ATGTCAGCTC GGGCCCGTTG ACAGCGATTC GTGGGCGCGT ACGACAGATG   1380
CAACGTTGCT CAACACCTGG ATTATCTCGG TGATGTTTGG CTTTGGTGTG TGGTTTGTTT   1440
TATATGGCCT GTCCCGGGCC GCTCAGCGTC GCATTTCACC AGACACACAT TCTGTACTGG   1500
TACGGCAGAA CAAGGAGACA CAGGAATGAA ACCAACTCTT CTCGCAGGAC TGATTTTCTG   1560
GGGCATGATG GCGCGCCGTA CTGAGCGAGC TGATGACCTG GTCCGTGGAG CATACACAGC   1620
AGGGCCTGCT GTGGCTGTGC AATGGGATGT GGGCCGGGGC GGCTGGCATG GTGATTTATG   1680
CAGGTTATCG CTGGTACCGT GACGAAAGAG GGCAAACGCA TAAGGAAGGC GATCATGAAC   1740
ATTAAAACCG GACTCACGGC TCTGCTGATG TGCCTGCCCC TGCTGGCGAA CGCGGGGGCG   1800
CGCGAGGAGT TAATGGCGCT TGAAGCGACA AAAACAACCT CTGCTGACGC TGCAGCCATC   1860
ACCGCCTCCA CCATTCCGGT ACCTGCGCCG GCCAGCCTGA TGGCGCTGCC GGACGGACGT   1920
CGGGCTAACA TGAAAGATTA TGCCGTGGTG CTTTTTATGC AGGCACACTG CCAGTACAGC   1980
GCGAAGTTTG ACCCGCTGCT GAAGGGCTGG GCTGATGAGC ATTCTGTCAG GGTTATCCA    2040
TACACCCTGG ACGGCGGCGG TGATGTGTCT TACCGACGCC GATGATCCCG CGCAAGACGG   2100
ACCCGAATTC TCCCATTGCA GACGAGATTG TCACCTTCTT CGGAAACGGG CTGCCGATTG   2160
CGACACCAAC GGCCTTTATG GTCAACGTTA ACACCCTGAA AGCCTACCCG CTGACCCAGG   2220
GTGTGATGGA CATCCCCGCT CTTGAGAGCC GTATGGCCAG CCTGATTCAG GCTGACATGG   2280
ACAACGTCGA TCCGAAAACG CTGCCGCCCA TGCCGGCAAG TGCGCAGGTC ACCCCTCAGT   2340
AATACAAACG GACTACAAAA TGACGACAAA TACGTATGCG TTATCGCGTA CCGAGCGCGT   2400
GTGGCTGTTA TTCAGCGTGA CGCTGCTTGT GTCCGCAGCT TTCTATGGGG TACTGGCCCA   2460
CCGGGTGGTC AGCGTCTGAC CGTCAGACTG ACAACTGTTT GCAGGACTTT CCGGTGCTCC   2520
TGCTTATCTC GCTGAGTATC GGATTCTTTT TCACCGTCAC CGGGCTGTAC GTCTGCCGGC   2580
AGACCCTGGT CAGGAAACCC CGGGAGGAGA TTGCATGAGG CACATCAGAC TGAAGACGTT   2640
TATCCGAAAC CAGGCTATCG GGATACTGAA AGACAGTAGT GAGGATACGG AAACCCGAAA   2700
ATGGACGGAT TTGTTAACCC TGAAACTGTT TTTATGCCTT AATTTTTACC GCCGTAGTCG   2760
AAAGGGTATA CGTGAAGTGC GCCATCACAA CGCTCAGTGC GATCTCCGTT GACCGCTCCG   2820
AACAGTTTAC GCTCTCGCTT CTCATCCACT ATCCACAGTA CCTGTTGTGG GGCGTTATGG   2880
CCGCGATTAT CGCGCTCATT GCGGTGAATT TACTCGTCTG CGGCTGGTTC TGTCTGGCCA   2940
CATATCTTTG CCGCAAACTG AACCGGACTG ACATCCCGGC AGGCAAGGAT ATGCAAGCTG   3000
TGGAGGTGCC TAATGATTAA GGCGCTTATT ACGGCAGGGG TTGTGTTCTT CTCAGGTCTG   3060
GCAGCGCTGC CTGCTCAGGC GGACGTCAAT GGTGACTCAA CGGCTTCTTT GGCAAGCTGG   3120
```

```
GCTACAGCGG CAACGTCTCT CAGGCGCAGG CCTGGCAGGG GCAGGCGGCC GGGTATTTCT   3180
CCGGCGGGTC GGTCTACCTG CGAAACCCCG TCAAAAACGT TCAGCTGATC TCGATGCAGC   3240
TGCCGTCCCT GAACGCCGGC TGCGGCGGTA TCGATGCCTA CCTGGGGTCA TTCAGCATGA   3300
TCAGCGGTGA GGAAATTCAG CGATTCGTGA AGCAAATCAT GAGTAACGCG GCTGGCTATG   3360
CATTCGACCT GGCACTGCAG ACGATGGTCC CGGAGCTGAA GCAGGCGAAA GATTTCCTGC   3420
AGAAGCTGGC CAGTGATGTT AACTCCATGA ACATGAGTTC GTGCCAGGCC GCTCAGGGCA   3480
TCATAGGCGG GTTGTGGCCC GTAACGCAGG TGTCACAGCA GAAAATCTGC CAGGACATTG   3540
CCGGCGAAAC CAACATGTTT GCTGACTGGG CGGCCTCCCG CCAGGGCTGC ACCGTCGGAG   3600
GACAGGGGGA TAAAGTCACG GCCAAAGCCG GCGACGCAGA AAAAGACCCC AGGTACTGAA   3660
AAACAAAAAC CTTATCTGGG ACACGCTCAG TAAGAACGGG CTGCTTGGTA ACGATCGCGC   3720
CCTGAAGGAG CTGGTCATGA GTACTGTCGG CTCCATCATT TTCAACAAAA CCGGAGACGT   3780
GACATCCTGA CGCCGCTGGT CGATACCGCG ACCTGATTAA AGTTCTGATG CGCGGGGGAA   3840
CAGCGAAGGT CTACGGGTGC GATGAGGCAA CACTCTGTCT GGGGCCTGTC GTTACTAACC   3900
TGACGATTAC TGAGTCCAAC GCTCTGGTCA CACTGGTCAA AAAACTGATG CTCTCGATGC   3960
AGAACAAACT TGTCGATGAC AAACCGCTGA CCGATCAGGA AAAAGGCTTC GTGAACACCA   4020
CCTCTGTGCC GGTACTGAAA TACCTGACCA ACGCCCAGAG TATGGGGATG AGCGCCACGT   4080
ACCTCCTGCA GGTTTCCGAC TTCATCGCGC AGGACCTGAT GATCCAGTAC CTCCAGGAAC   4140
TGGTGAAACA GGCAAGCCTG TCTCTGGCTG GTAAGAACTT CCCGGAAGAG GCCGCTGCGA   4200
AGTGCGCGAC AACATCATTC ATGCCCAGGG ACTGCTGGCC GACATGAAGC TGCAGTCTGC   4260
GGCAGACCAG AACGCACTGG ACGGCATCGA CCGCAACATG CAGTACTGCA GCAGCAGGTG   4320
TCCACCATTG TTTCAGGCTC CTATCAAAGC AACTATCACT GGGGTGATCG CTGATGCTTG   4380
AGATATACAC CATTTATGGC GGGGGAATGT GGAAAAACGC GCTGGACGCC GTTGTCACCC   4440
TTGTCGGTCA GAATACCTTC CACACCTTAA TGCGTATTCG CCCGGCACCT TCGGGGTGCT   4500
GGCTGTATTG CTCACTTTCA TCAAACAACG TAACCCGATG GTCTTCGTCC AGTGGCTGGC   4560
GATCTTCATG ATCCTGACGA CCATCCTGCT GGTACCGAAA CGTTCAGTAC AGATAATTGA   4620
CCTCTCAGAC CCCGGCTGCG GTGTGGAAAA CCGATAATGT ACCGGTCGGT CTGGCTGCCA   4680
TCGCGTCACT GACGACCAGC ATCGGTTACA AAATGGCATC GGTGTACGAC ATGCTGATGG   4740
CCAGACCTGA CTCGGTAACC TACAGCAAGA CCGGTATGCT GTTTGGCTCG CAGATTGTGG   4800
CGGAAACCAG TGACTTCACC ACGCAAAACC CGGAACTGGC TCAGATGCTG CCGGACTACG   4860
TGGAAAACTG TGTGATCGGC GACATTCTGC TGAACGGTAA ATACACCATC AATCAGCTGC   4920
TCAATTCCAC TGACCCGCTG ACGTTGATAA CCAGTAACCC AAGCCCGCTG CGGGGCATCT   4980
TTAAGATGAC CTCCACCTCG CGCCAGTTCC TGACCTGTCA GCAGGCGGCA ACGGAGATTA   5040
AGACGCTGGC GAATACCGAC GTCAATCCGG GCAGTGCGAC GTTCACCTGG CTGACGCGGA   5100
AGGTATTCGG CAACAAGCTG AATGGTGCCT CGCTTCTGCC AACGCTATGG GTGAGAGCTA   5160
CGGATTCTTC TATGCCGGGG GAATGACGGC TGCGCAGATC ATGAAGAACA ACATCACGAA   5220
CAGTGCAGTT CGGCAGGGGA TTAAGGGTTT CGCCGCTCGC TCATCCGACA CGGCTAACCT   5280
GCTGAACCTG GCCACCGAGA ACGCTGCAAC CAAACAGCGT CTCAGCTGGG CTGCGGGTAA   5340
TGAGCTTGCC ACCCGAACTC TGCCGTTTGC ACAGTCCCTG CTGATGCTTA TCCTGGTGTG   5400
CCTGTTCCCG TTGATGATTG CGCTGGCCGC ATCAAATCAC ACTATGTTTG GGCTGAACAC   5460
CCTGAAAATA TACATTTCCG GTTTTATCTA TTTCCAGATG TGGCCGGTGA TGTTCGCCAT   5520
```

-continued

| | | | | | | |
|---|---|---|---|---|---|---|
| CCTTAACTAT | GCTGCCAACT | ACTGGCTGCA | GAGTCAGTCC | GGGGGCACGC | CTCTGGTGCT | 5580 |
| GGCCAACAAG | GATGTAGTGG | CACTGCAGCA | TTCGGACGTG | GCGAATCTGG | CAGGGTATCT | 5640 |
| GTCGTTGTCC | ATTCCGGTGC | TGTCGTTCGT | ATCTGACCAA | GGGGGCTGCG | GCGATGGGCT | 5700 |
| CTCAGGTGGC | AGGCAGTGTC | CTCAGTTCGG | GCGCCTTCAC | GTCGGCAGGT | GTGGCAGCAA | 5760 |
| CCACGGCGGA | CGGGAACTGG | TCGTTAACA | ACATGTCAAT | GGACAATGTC | AGCCAGAACA | 5820 |
| AGCTGGATAC | CAACCTGATG | CAGCGTCAGG | CCAGCAGACG | TGGCAGGCAG | ATAATGGTTC | 5880 |
| CACGCAGACG | CAGACGCCGG | TGGCCATACG | GTATCGACGG | CTCAGGCGCA | ATGTCGAATC | 5940 |
| TGCCGGTGAA | CATGAAGCTC | AGCCAGCTGG | CCAGCAGTGG | TTTCCAGGAG | TCTGCCCGCC | 6000 |
| AGTCGCAGGT | CCAGGCGCAG | ACGGCGCTCG | ATGGCTACAA | CCACAGTGTC | ACCAGTGGCT | 6060 |
| GGTCGCAGCT | CTCACAGCTG | TCTCACCAGA | CCGGTACCAG | CGACAGCCTG | ACCAGCGGCA | 6120 |
| GTGAAAACAG | CCAGGCCACT | AACTCAACGC | GCGGCGCGAG | CATGATGATG | TCGGCCGCTG | 6180 |
| AAAGCTATGC | GAAAGCTAAC | AATATCTCGA | CGCAGGAAGC | CTATAACAAG | CTGATGGATA | 6240 |
| TCAGTAATCA | GGGTTCTGTA | TCTGCAGGCA | TTAAAGGTAC | GGCCGGAGGG | GGACTTAATC | 6300 |
| TGGGCGTTGT | TAAGCTT | | | | | 6317 |

( 2 ) INFORMATION FOR SEQ ID NO:22:

( i ) SEQUENCE CHARACTERISTICS:
        ( A ) LENGTH: 6914 base pairs
        ( B ) TYPE: nucleic acid
        ( C ) STRANDEDNESS: double
        ( D ) TOPOLOGY: linear ( i i ) MOLECULE TYPE: Genomic DNA ( v i ) ORIGINAL SOURCE:
        ( A ) ORGANISM: Enterobacter cloacae
        ( B ) STRAIN: Clinical Isolate ET- 49

( x i ) SEQUENCE DESCRIPTION: SEQ ID NO:22:

| | | | | | | |
|---|---|---|---|---|---|---|
| AAGCTTTTCG | AGTTCGCCAT | CCGGCAACAG | CTCACTGAGC | TTTTACGCGC | CCAGGGTGCC | 60 |
| TTTGAACTCA | ATTCCCAGCT | CAGTAAGGCG | GTCCTGAATA | ATCTCTTTGC | GAGATTTTTC | 120 |
| ACTGGTACCG | GCATCAGGTG | TTGCAGGTTT | CAGCTCGCCA | CCAGCCTCGC | CCTTCATCAG | 180 |
| CCGGACGTTA | GACTTCAGCG | CCGGGTGAAG | ATCTTTCAAC | TCCACCACGT | CGCCAACCTT | 240 |
| TACGCCGAAC | CATGGGCGCA | CAACTTCGTA | TTTAGCCATG | CTGTTTCCTT | ACGCCAGGTT | 300 |
| AGCGCCGTAG | ACAACGCCAG | ACAGGCCTGA | TCGTCTGCAG | TAATTTGCAG | GCCTTCAGCA | 360 |
| GACATGATCT | GGAAGTTGTA | GTTAACGTTA | GGCAGTGGGC | GCGGCAGTGG | CACAACGCCA | 420 |
| ACAGCCATAC | CCACCAGTGG | GGAGATCACG | TCACGACGAC | GAACGTACGC | GATAAACTCG | 480 |
| TTACCGGTCA | GCGCGAAGTC | ATGCGGATTT | CTTTCACCGG | TGCGAATGGC | AGAACAGCCT | 540 |
| GCAGGAGAGT | GCCGCTCACC | ACACCATTAA | CTACGTATGG | CTGAGCCATA | TTTGCCCAGA | 600 |
| TCTCAGGGGA | AACCCACATC | ACATCATACT | GAGCTACTTT | GTTGGTGCGT | GCGGTGGTAC | 660 |
| CGAATGCTCC | TTTACCAAAG | AACTCAAAAT | ATTGAGTCGT | GGTTGCGCTG | GTCAGGTCGA | 720 |
| TGTTCGCACC | ACCAGCACCA | GAACCGAGGT | TAATCTTCTT | GGTGTTGCGG | TGGTTCTTGA | 780 |
| TGCCCTGCGC | CGGGTAGGAC | TGAACCTGAA | TTTTTGAATC | GCCGTTCAGG | TAGTAGTTGA | 840 |
| CGCGCTTCTG | GTTGAACTTG | CGCATCTTCG | CCATCTGCGA | ATCCAGAACC | AGATCAATGC | 900 |
| CTACAGAGTT | AAGGCCAGCA | GCATGACGCC | AGTTAACACC | GTAGCCAGCA | GTGAACACCG | 960 |
| GAATCGGGTC | GCCATCGCTC | GCGTAGTCAG | TGTGGTCGAA | GGAGAATGGC | GCCTGACCAT | 1020 |
| CGATGCTTAC | TGACACGTCG | TCAGCGATGT | CGCCGACCAC | GTTATACAGC | TTGGCGGTTT | 1080 |

-continued

```
TACCAACCGG CAGCACGGTC TGAACGCCGA TCAGGTCGTT TACGATTTCC ATGCCAACTT    1140
CCTGATCCCG CAGCTGCAGC ACCTGGTTGT CAATCTCAGC CCAGAAGTCA CGGGAGAAAC    1200
CGCCAACAGC GTTACAAGCC AGCATGTCAG GCGTCATCAT TGCGCGGTTA GCTGCAATGA    1260
TGGAATCGTT CTGTAGGTTC CACATGTTGC GGTTTGCCCA CAGCTCACTC CAGTGCCCGC    1320
CGAGGCGGGA GTTAGTCGCC AGCGTCTCTT TAGAGAAGTA CATATGTGTT TGTCCTTTTG    1380
TTACGCGCCA GCTGCGGCGA CAGTGCCAAC GCGCATACGC ACGCGAATGA AGTCAGTGGT    1440
GCTGGCCGCG ATGGTGTATT CATCCTGGCT GTAGCCGATC ACTGAATCAG TGTCGGATGT    1500
GGCAAGGGTA AACTGACCGG CAGTTCCCAG CTTGATCGGG CTGTCTTTTT TATACGCACC    1560
AGGCAGGCAG CGCAGCGCCA GCTCACGACC TTCTTCGACG TAGTTACCTA CTGCCGAATC    1620
CCCGGCAGGG ATTTCTTCGG TGATTGTCAG GCCCTGGTGA TAACCGACAT CGATGATGTA    1680
CAGGCGGCCG GTTAGCGCGG TGGCCTGAGC GAATTATCG  GATGAGTTGA TGGTTGCGGC    1740
GGTGCCAGGA AGCAACCCGG CGGCCGTTGT GCGGGTTTCG GTCTTGTACA GAGACTGACC    1800
GTCGATATTA ACGCGACGAT AACGTGGCAT TATTCCGGCT CCTTACTTGA AGTGTTCGTC    1860
TGCGGCTGGT GCGCCGGTTT CTTTGTGCTG CTGAGCATTG TTGGTGCCCA GCGACTTGAA    1920
CATCGCGTCC AGAGCTTCGC CTGACAGAGC GTTCGCGAGC GATATCGCCA TGGACCTTCG    1980
CAACCGCTTC GCGCTTTGCT TTCTCTTCGG CACGGGAGTT CGCGGTAAGG GTTTCCGCGA    2040
GTTGCTTCTG ATTGGCCTGC AGCGCATCAA CCTTTTCCGC GAGAGGCTTA ATAGCCGCTT    2100
CAGTATTGGT CGCAACAGCC TGGCCGATCA TGCTGCCGAT TTGTTCCAGT TCTTCTTTGG    2160
TTAAAGGCAT GTCGCCTCCG TTTTGTGGTT TGGTGCAGGC TGTTCCTGCG GTGTGAATAG    2220
AGCTTTGAAT TGTTAGCGAC GACTGCCACC CACGACTCCT GGCGCGCTAC TGCGGTTCCG    2280
GTATCGTCGA TTGTGATCTT CCCGCCATCA GCGAATACCG TAAACCTGAG CATCACCGCC    2340
ATTTCGCACG ATGACCACCT GCGAGTCAGT GAGTCAGCAA CCCAGGCATA TTCATCCGTG    2400
CCCGGCGCAA ACTTGGCTTT GGCTGCCCGA TCGAGACGCT GCTCGCGCTC CCGGTAGGAT    2460
TCACCCACCA GCGCGCCGGA GTTCGCTTTA AGCGGCTGCG CCAGATCGGC GTTTACCATC    2520
AGGCCAACGC CCTGCTCAGG GGTGGCGGCT CCGACTTCGT GCAGTAGGAT CGCGTCGTGG    2580
TCCATGCTGT GAATCTTCGC CACCCACTCG GCACCCGTAG CTCTCTGTTG TTCGTTAGGC    2640
TCAAGCTGGT CGAGGAAAGC GGCGACACTG GTATGAATCG GCGGAACGTC ATCGCCGCGC    2700
TCGATGGCTG CGACGCGCTC AAGTAGTTCT CGGCCACCTT CAGACTCACC GGCGCGGGCA    2760
ACATCAACCC ACTTTTCGAG GTAGATACGA TTACCGGACT TCTTAACGTT GCGGTTCCAC    2820
GCGCCGATAT GGCCTGCGTT AATCCCCTCC GGGGAGAAAG CAGACACGAA CTGACCATTA    2880
ACCTGAGGGT GGCCCAGCGG CGCCAGGGTA CCTTCCAGCC CCTTATAGTG GGCGTCGATT    2940
TGCTCTTGCG TGTACAAGCC GCCATTCATG ACGACGTTAG CTGGAAGTGT GTAGCTCGGC    3000
AGCACCAGGT GCTCACGCCC GTTGTATGTT TCGCGCCGGA TAGACTGGCT GTTCACCTTT    3060
GTGGTGATGT TGACCTGAAT ATGCTCACCA TGTTTCGGTG CCTGGATTGG ACGCTGTGCT    3120
TCGTGGTTTA CCTGGAATTT CATGAGTTAT TTCTCCGCCC AGGCGTAACC GCTCGCCTGC    3180
ATCGATTTAT ATTCCTGTTT GAGTTTCGTG ATGGTGTCCG GGTATTCCGG CTTGCCGTCC    3240
GCATCCACCA GCACCGACTG CTGGCTGCAT TTGCAGTTGA TGGAGTTGCC ATCTTTGCTG    3300
TACCAGTCAC GCACCTCTTC GTTGGTGTAG AGGTGGGCAT GGGCGCACTG CGTGGGTATG    3360
TCGCGTTGTC GGCGACAGAG CTGAGATGTG AACCAGCAGC GTTTTAAGGC CGAACAGGTC    3420
ATTCGCCTCT TGGTCTTCAT CCCACTTGGC CCGGCGCAGC GCGGTAGTCA CTTCAGTGCG    3480
```

-continued

| | | | | | | |
|---|---|---|---|---|---|---|
| TGCTATCCGG | TTAGCCCGGC | GTTTCTCGAT | GCCGGTCTGG | TCTGTCAGGT | TGCGGGCAAT | 3540 |
| GTCCAGAGGA | TTGAGCCCGC | GCCCAACACC | ATCAGTAAGA | CACGCGCCAT | GTCGCGCTTA | 3600 |
| ACGTCAGCCG | TCAGCCCCTT | CATTTCCTCA | AATACACGCG | CATGCACCAG | CGCCATGCGT | 3660 |
| TTCTGATACT | GGTCGCTTGC | GAGGATGGAG | GCCAGCGACT | CACGCCCGGC | TGCGTACACC | 3720 |
| GGGGATTGCT | GACTGAGGTT | GTAGAACGAC | TGCCCGGTCC | CTTTTTCCGA | AGCCAGATCG | 3780 |
| ATGTACTCGT | AAAACCACAG | GTCGTAATCG | CCACCTTCAA | GCAGTACCTG | ATCAACCAGG | 3840 |
| TAACTGGCAT | CGTTCAGGAT | GATGGAGAGT | AGCATTGGGT | TTAGCTGGTA | TTCGTATCTG | 3900 |
| GCGTTTACTG | CGAGGGAGGA | AGGTATTTTG | TTGAGTGCTG | ATTTGTACGC | CTTGCCAATC | 3960 |
| TTATTCATCC | GCCTGGCGAA | GTCTTTCATT | GCCCGGCGTT | CCAGCGCATC | GGCTCCGGTC | 4020 |
| GGATCCTGAT | AGTTACGCGG | CAGAATCGGT | GGCTTCGTCT | TCTTCGTCGC | CATCCTCTTC | 4080 |
| TCCTAATGGA | AATTCATCGA | CGTTTTCATA | ACCGGCAGCA | GTGCGGAATT | TCTTCACGAC | 4140 |
| TAAAGGCTGG | TTTTTCTCCG | CTCCCCTGGA | ACGTCTGGTT | AATCTCTGCC | ATGGTTTTGG | 4200 |
| CATTTGCGAG | TTTCTCAGTT | CCAGTCTGTT | CGTTGAGGTC | ATCCAGATA | ACCGTCTTCT | 4260 |
| CGCTGACTGC | ATCAATAATT | TTCAGGTCGA | TGAGCTTGTC | ACTGAAGTCT | TCAATTTCGA | 4320 |
| ATGACAGGTC | ACCGCGCCGT | GACTGGCAGC | GCGCGTTGAA | ATATTTCTGA | TCCTCGGTGC | 4380 |
| TTGCCCTTTC | ACCCGTCTGC | ATCCCAACCA | GAACCTTCAC | AGGGATATCA | ACAGATGCAG | 4440 |
| CGAAGGTTTG | CAGGTTGACG | TTATAGGTCG | CTGACGGATC | CGCTACAGCT | GTGACCAGTG | 4500 |
| GTGTGACTGT | AGCCCCTTGG | GTTGTCATCA | GAACATCGTT | ACCACGGTTC | ATTTCCCCGG | 4560 |
| CAACTTCGTT | AAACTTATCC | TGCAACTCGT | CCATGTCACG | CCATAAAGTG | ACGCGAGATT | 4620 |
| GTTGAAATCG | ATTTCCTTCT | CAAAGTTGAC | ATTAAGCTGC | CGCGCGGCGT | TCTTTAGGAA | 4680 |
| TGACTCACCA | GAACCACCCT | CGACCTTCTC | AAGGCTGACG | CAGGCGTTAT | AGCCAGGCTC | 4740 |
| AAGGAAGCCA | ATAGCATCAT | TAGAATAGTC | ACCAAGGATA | AAGACGCGAT | CGGGATGTAC | 4800 |
| GAAGCGCTGA | TTAGTTCCAC | CGCTTGGAAG | GCTCTCAACA | TATTTCCACT | GCTTTGGCTG | 4860 |
| CCCGTAGCCT | GCCGATTTCT | GGTCAGTTAC | CCACTCGCTG | ACTGTTAATG | ACCCAGCCCA | 4920 |
| TGCGATCGTA | ACCTTTTTTA | GTGACTTGCC | ACGAACAACA | GGCTGATCCC | ATGTTCTGGA | 4980 |
| ATCATTGATA | TGCAGCAGGA | TACCCGCATA | ACGTCCGACC | TGTCGGCGGC | GGTCTGCTTC | 5040 |
| AGCAAAAGCC | CGCCAAAGGC | GCTTTGTGAA | AACCTTTTTG | GTGTTCTTCT | CCCAGGCAGT | 5100 |
| TTCATCCTTA | CTCTCGTCGG | CATCATCACC | CTCGATGATT | TCCGGGTTGG | TCTGCCAGCA | 5160 |
| CTTGCCCACC | AGCTTCTCTA | CTGCGCCGTG | GGCTATTCCA | CCGCGACGAT | ACAGTGCGTA | 5220 |
| GAGGTTTTCG | TAAGTGACCT | GCTCAGGGAA | TCCATACTCG | CACCATGCGG | AATGGCGCTT | 5280 |
| ATTGTCCAGC | CCCATTGTAG | GCGCCAACAG | CCCCATACGG | GCACGGGCCA | TCCGCGCATC | 5340 |
| GTTCAACGCA | TGGTTGACGG | CGAGAGTTAA | TTTGTCAGTC | ATGGTTTGTC | CGTTGGTGGA | 5400 |
| TTTAAGGCAT | AAAAAAAGGC | CGCTTTGGCG | ACCTTGTGGC | TATTTAAAAA | GCTAAACTCT | 5460 |
| GTTAACGAA | ATAAACATAA | TCTGCTCAGG | CTTAACGCCA | TAATCACTTG | CCAACTTCTG | 5520 |
| AGTGCACTCA | ATTAAGACAG | TTGATGCAGA | TTTCGAAGAG | CTTGCACCAT | AAATTTCGAA | 5580 |
| GTTTTCAAAT | ACTCCGCCGT | TGGTGTGGTA | AATCTTATAT | GACATAAACC | AATCATTCAT | 5640 |
| AATATCTACT | CCCTTACAGA | ATTGAGTAGA | TATTATCGGC | AAGTGCATAT | GTTTCTTTAA | 5700 |
| ATTATCTCAA | CCTTTTCGGG | ATCATCATCC | CGGCCATCTG | GCCCTTACGT | TTAATGTGTC | 5760 |
| CGTCGAGGCT | GTAGCGAATA | CCGTCCCAGC | AGTGTTCGTA | ACCGTCTGCC | AGTTAGGCA | 5820 |
| ATACCTCGCC | GGTGATGCGG | TCCGTTTTGT | AGGACCACAT | GCGGGCCTCT | CTCGCCACAT | 5880 |

| | | | | | | |
|---|---|---|---|---|---|---|
| TCTTGCAGCG | AGGATGGATA | ATGATTTCGT | CAAAGCCGCG | AAGATGCGCG | ATACCGTCCT | 5940 |
| CAACACTCCC | CTGCCATTTC | TCGGCAGCCG | AGATGTTGAA | GCCCTGGCGC | TTGAGATAGC | 6000 |
| TGATAGTCTC | GGGTCGGGCG | GAGTCGGCCT | TGATGGGCCA | GTCACGCGAT | CCGGGGATTG | 6060 |
| TGTCGTATAG | CTCTGGCATA | TGGTCGAGCT | CTGTCTGCTG | ACCGTATGCC | TCGTATTCGA | 6120 |
| TGTACAGCCG | GTTGTGCAGG | ATGAACGAGC | GCACCAGCGT | GTTAGGGTCT | TTGGCGAAAC | 6180 |
| CGAAGTCAGC | ACCGAAGAAA | AGGCGATCGG | CCTCTTTCCA | TAGCTGGTCC | GAGAACTCAG | 6240 |
| CGATCCGGTA | TTTACCGGCC | AGCACCTGCT | TATCAGAGTT | TTCGAGGTAA | GCACCTTCCC | 6300 |
| AAACCCACGC | GTATGTTGCC | GGGTCAAGGC | GGCGCTGATC | GTTCTGTCGC | TCACCTTCCA | 6360 |
| GCACGTCGGG | GAACCATGGA | TTATCCGTGT | AGTTCATCTC | AACGTGATAC | AGTCGTCGCC | 6420 |
| AGCCTCTTTA | CGGAAACGCT | TATCCGTGCG | CTGCCGTCGC | GCTCCGGGTT | CCATGTCACC | 6480 |
| CAAATCTCTG | AACCTTCCTC | ACGAACGGTC | GGGCTCAGCT | TCTGCCAGGC | TATTTCGCTG | 6540 |
| ACTGATTCAG | CCTCATCAAC | CCAACAGAGC | AAGATGCGCG | CTTTCGACTT | GATGCTGTCG | 6600 |
| AGGTTATGCC | GCAGACCGCA | GAACACGTAG | TTAACGCTCT | TGTCGATGGT | GCGGATGTAC | 6660 |
| TTCTCGCCGA | TATCAAAGTT | GGAAGCCAGC | CAGGGAACAG | ACAGGATAGC | CTGTTTCACC | 6720 |
| TCCTGCATAC | TCGACTCTTC | CAGTGAGTTC | ATGAATTCAC | GCGCACAGAG | CACCACGCCG | 6780 |
| CTTTCACCGT | TCATCATCGA | CTGATACGCC | TTTACGGCTG | TCATCAGCGC | AAAAGTGCGC | 6840 |
| GTCTTGGCAC | TACCACGCCC | ACCATGCGAG | CACCGGTAAC | GCTTATTCTC | GGCGATGAAC | 6900 |
| AGTGGCGCAA | GCTT | | | | | 6914 |

(2) INFORMATION FOR SEQ ID NO:23:

(i) SEQUENCE CHARACTERISTICS:
        (A) LENGTH: 5975 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Klebsiella pneumoniae
        (B) STRAIN: Clinical Isolate KI-50

(xi) SEQUENCE DESCRIPTION: SEQ ID NO:23:

| | | | | | | |
|---|---|---|---|---|---|---|
| AAGCTTATTC | CACGCTGGAG | GCGTCCGGGA | TTATCGGCGT | CAACGCTATC | GCCGGCATCG | 60 |
| CCGGGACCAT | CATCGCCGGC | ATGCTCTCCG | ACCGCTTTTT | CAAACGCAAC | CGCAGCGTGA | 120 |
| TGGCCGGATT | CATCAGCCTG | CTGAACACCG | CCGGCTTCGC | CCTGATGCTC | TGGTCGCCGC | 180 |
| ACAATTACTA | CACTGATATT | CTGGCGATGA | TTATCTTCGG | GGCCACCATT | GGCGCTCTGA | 240 |
| CCTGCTTCCT | TGGCGGGCTG | ATCGCCGTCG | ATATCTCTTC | GCGCAAGGCC | GCCGGGGCCG | 300 |
| CGCTCGGCAC | CATCGGCATC | GCAGCTACGC | CGGCGCCGGC | CTGGGCGAGT | TTCTCACCGG | 360 |
| GTTCATTATT | GATAAAACGG | CTATCCTTGA | AAACGGCAAA | ACGCTGTATG | ATTTCAGCAC | 420 |
| GTTGGCGCTG | TTCTGGGTGG | GTACGGTCTG | GGTTCNGCGC | TACTCTGTTT | TACCACTGCC | 480 |
| GCCATCGTCG | CCCGGCGCCA | TGCCGTCGAA | CGGCAGACCT | CGTTCTCCTC | ATAACCGATT | 540 |
| AACGAATAAG | GAAGAAGATA | TGATGCCTGC | AAGACATCAG | GGGCTGTTAC | GCCTGTTTAT | 600 |
| CGCCTGCGCG | CTGCCGCTGC | TGGCGCTGCA | ATCTGCCGCC | GCCGCGGACT | GGCAGCTGGA | 660 |
| GAAAGTGGTC | GAGCTCAGCC | GCCACGGTAT | TCGTCCGCCG | ACGGCCGGCA | ACCGGGAAGC | 720 |
| CATCGAGGCC | GCCACCGGCC | GACCGTGGAC | CGAGTGGACC | ACCCATGACG | GGGAGCTCAC | 780 |

```
CGGCCATGGC TATGCCGCCG TGGTCAACAA AGGGCGTGCG GAAGGCCAGC ATTACCGCCA    840
GCTCGGCCTG CTGCAGGCCG GATGCCCGAC GGCGGAGTCG ATATACGTGC GCGCCAGCCC    900
GCTGCAGCGG ACGCGAGCGA CCGCCCAGGC GCTGGTGGAT GGCGCCTTCC CCGGCTGCGG    960
CGTCGCTATC CATTATGTCA GCGGGGATGC CGATCCCCTG TTTCAGACCG ACAAGTTCGC   1020
CGCCACGCAA ACCGACCCCG CCCGCCAGCT GGCGCGGTGA AGAGAAGGC CGGGGATCTG    1080
GCGCAGGTCG GCAGGCGCTG GCGCCGACCA TCCAGCTATT GAAACAGGCG GTTTGTCAGG   1140
CCGATAAGCC CTGCCCGATC TTCGATACCC CGTGGCAGGT CGAGCAGAGC AAAAGTGGGA   1200
AGACCACCAT TAGCGGACTG AGCGTGATGG CCAATATGGT GGAGACGCTG CGTCTCGGCT   1260
GGAGTGAAAA CCTGCCTCTC AGCCAGCTGG CGTGGGGCAA GATCACCCAG GCCAGGCAGA   1320
TCACCGCCCT GCTGCCGCTG TTAACGGAAA ACTACGATCT GAGTAACGAT GTGTTGTATA   1380
CCGCGCAAAA ACGCGGGTCG GTGCTGCTCA ACGCTATGCT CGACGGCGTC AAACCGGAGC   1440
GAATCGAACG TACGCTGGCT GCTGCTGGTG GCCATGACAC CAATATCGCC ATGGTGCGCA   1500
CGCTGATGAA CTTTAGCTGG CAGCTGCCGG GCTACAGCCG GGGAAATATC CCGCCGGGCA   1560
GCAGCCTGGT GCTGGAGCGC TGGCGCAACG CGAAGAGCGG AGAACGCTAT CTGCGGGTCT   1620
ATTTCCAGGC CCAGGGCCTC GACGACCTGC GTCGTCTGCA GACGCCGGAC GCGCAGACCC   1680
CGATGCTGCG TCAGGAGTGG CATCAGCCGG GCTGCCGTCA GACCGATGTC GGTACGCTGT   1740
GTCCCTTCCA GGCGGCTATT ACCGCCCTCG GTCAGCGTAT CGACCGATCA TCCGCCCCGG   1800
CGGTAGCATG GTCCTGCCGT AGCGGCGCGG TGTTTGTCCG GGCCCGGGAA AACCTTTTTT   1860
TCCAGGCCGG CACGACGTCC GTTATCCGTT GTCCGGCGCA AACGCCCCGG CGGCGACCTG   1920
CGCCGGGGTG ACACCCGCTG TCCAGCACCC AGCCGCTTAT CAGCCCAGCA GGCGTGACGT   1980
CGAACGCCGG ATTGTAAACG GTGGCCCCCG TCGGCGCCCA CTGTACCGCG CCGAAGCTGC   2040
CCGCCACTCC GGTCACTTCC GCCGCCGCGC GCTGCTCAAT GGGGATCGCC GCCCGTTCG    2100
GGCAATGGCG GTCGAGGGTG GTCTGCGGGG CAGCGACGTA AAACGGGATC TGGTGATAAT   2160
GGGCCAAAAC CGCCAGAGAA TAGGTGCCGA TTTTATTCGC CACGTCGCCG TTGGCGGCGA   2220
TACGGTCGGC GCCGACCCAC ACCGCATCCA CCTGCCCCTG CGCCATCAGG CTGGCGGCCA   2280
TTGAATCGGC GATCAGCTGA TAGGGCACGC CCAGCTCGCC CAGCTCCCAG GCGGTTAAAC   2340
GACCGCCCTG CAGCAGCGGC CGGGTTTCAT CAACCCATAC GTTGGTCACT TTTCCCTGCC   2400
GGTGCGCCAG CGCGATAACG CCGAGGGCGG TCCCTACCCC GGCGGTCGCC AGGCCACCGG   2460
TGTTGCAGTG GGTCAGCAGT CGACTGCCGG GCTTCACCAG CGCACTGCCC GCCTCAGCGA   2520
TGCGGTCGCA CAGCTGTTTA TCTTCTTCGA CCAGACGCAA GGCTTCCGCT TCCAGCGCCT   2580
GCGGGTAATC TCCGGGCCAG CGCTGCTTCA TGCGATCAGA TTATTCATCA GGTTGACCGC   2640
CGTCGGCCGC GCCGCGCGCA GTCTCCAGCG CCTGCTGGAG TGCATCCCGG TTCAGGCCGC   2700
GCTGGGCCAG CAGGGCCAGC AGCAGGCTGG CGGACAGGCC AATCAGCGGC GCGCCGCGCA   2760
CCCCGCAGGT ATGAATATGG TCCACCAGCA GCGCAACGTT ATCCGCCGCC AGCCAGCGTT   2820
TTTCCTGCGG CAAGGCCTGC TGGTCGAGAA TAAAAAGCTG ATTTTCACTC ACCCGCAGGC   2880
TGGTGGTCTG TAATGTCTGC ATGTCGTTAA ATCCCTGTTG CGTTGTTGTA TCACATTGTG   2940
TCAGGATGGA ATCCAGAAGT ATAGACGTCT GAACGGCTTA ATCAGAATTC GAGGATCGAG   3000
GCAATGTCGC AATACCATAC CTTCACCGCC CACGATGCCG TGGCTTACGC GCAGAGTTTC   3060
GCCGGCATCG ACANCCATCT GAGCTGGTCA GCGCGCAGGA AGTGGGCGAT GGCAACTCAA   3120
TCTGGTGTTT AAAGTGTTCG ATCGCCAGGG CGTCACGGGC GATCGTCAAA CAGGCTCTGC   3180
```

-continued

| | | | | | | |
|---|---|---|---|---|---|---|
| CCTACGTGCG | CTGCGTCGGC | GAATCCTGGC | CGCTGACCCT | CGACCGCGCC | CGTCTCGAAG | 3240 |
| CGCAGACCCT | GGTCGCCCAC | TATCAGCACA | GCCCGCAGCA | CACGGTAAAA | ATCCATCACT | 3300 |
| TTGATCCCGA | GCTGGCGGTG | ATGGTGATGG | AAGATCTTTC | CGACCACCGC | ATCTTGCGCG | 3360 |
| GAGAGCTTAT | CGCTAACGTC | TACTATCCCC | AGGCGGCCCG | CCAGCTTGGC | GACTATCTGG | 3420 |
| CGCAGGTGCT | GTTTCACACC | AGCGATTTCT | ACCTCCATCC | CCACGAGAAA | AAGGCGCAGG | 3480 |
| TGGCGCAGTT | TATTAACCCG | GCGATGTGCG | AGATCACCGA | GGATCTGTTC | TTTAACGACC | 3540 |
| CGTATCAGAT | CCACGAGCGC | AATAACTACC | CGGCGGAGCT | GGGAGGCCGA | TGTCGCCGCC | 3600 |
| CTGCGCGACG | ACGCTCAGCT | TAAGCTGGCG | GTGGCGGCGC | TGAAGCACCG | TTTCTTTGCC | 3660 |
| CATGCGGAAG | CGCTGCTGCA | CGGCGATATC | CACAGCGGGT | CGATCTTCGT | TGCCGAAGGC | 3720 |
| AGCCTGAAGG | CCATCGACGC | CGAGTTCGGC | TACTTCGGCC | CCATTGGCTT | CGATATCGGC | 3780 |
| ACCGCCATCG | GCAACCTGCT | GCTTAACTAC | TGCGGCCTGC | CGGGCCAGCT | CGGCATTCGC | 3840 |
| GATGCCGCCG | CCGCGCGCGA | GCAGCGGCTG | AACGACATCC | ACCAGCTGTG | GACCACCTTT | 3900 |
| GCCGAGCGCT | TCCAGGCGCT | GGCGGCGGAG | AAAACCCGCG | ACGCGGCGCT | GGCTTACCCC | 3960 |
| GGCTATGCCT | CCGCCTTTCT | GAAAAAGGTG | TGGGCGGACG | CGGTCGGCTT | CTGCGGCAGC | 4020 |
| GAACTGATCC | GCCGCAGCGT | CGGACTGTCG | CACGTCGCGG | ATATCGACAC | TATCCAGGAC | 4080 |
| GACGCCATGC | GTCATGAGTG | CCTGCGCCAC | GCCATTACCC | TGGGCAGAGC | GCTGATCGTG | 4140 |
| CTGGCCGAGC | GTATCGACAG | CGTCGACGAG | CTGCTGGCGN | GGGTACGCCA | GTACAGCTGA | 4200 |
| GTGCGCCTGT | TTCCCTCACC | CCAACCCTCT | CCCACAGGGA | GAGGGAGCAC | CCCCTAAAAA | 4260 |
| AGTGCCATTT | TCTGGGATTG | CCCGGCGNGN | TGCGCTTGCC | GGGCCTACAG | ATAGCCGCAT | 4320 |
| AACGGTTTGA | TCTTGCACTC | TTTCGTAGGC | CGGGTAAGGC | GAAAGCCGCC | ACCCGGCAGA | 4380 |
| CATGCGAGTA | CAATTTTGCA | TTTACCTTAC | CCTCACCCCA | GATACTCAAT | CACCGATAGC | 4440 |
| CCGCCGTTGT | AATCGGTGCT | GTAGATAATG | CCTTGCGCAT | CGACAAACAC | GTCACAGGAC | 4500 |
| TGGATCACCC | GCGGGCGGCC | GGGACGGGTA | TCCATCATTC | TCTCAGCGCA | GCCGGCACCA | 4560 |
| GCGCCCCGGT | CTCCAGCGGG | CGATACGGGT | TGGAAATGTC | GTAAGCCCGC | ACGCCGGCAT | 4620 |
| TCTGATACGT | GGCAAAAATC | AGCGTTGAGC | TGACAAAGCT | CCCCGGCCGG | TTCTCATGCA | 4680 |
| GGTTGTGCGG | ACCGAAATGC | GCCCCTTTCG | CCACGTAATC | CGCTTCATCC | GGCGGCGGGA | 4740 |
| AGGTGGCGAT | GCTCACCGGG | TTGGTTGGCT | CGCGGATATC | AAACAGCCAG | ATCAGCTTCT | 4800 |
| CGCCGTCCTC | CTGGTTATCG | AGCACCGCTT | CATCCAGCAC | CACCAGCAGA | TCGCGATCCG | 4860 |
| GCAGCGGCAG | CGCGGTATGC | GTTCCGCCGC | CGAACGGCGG | GCTCCAGTTG | CGATGGCTAA | 4920 |
| TCAGCCTCGG | CTGGGTACGG | TCTTTGACAT | CCAGCAGCGT | CAGGCCGCCG | TCGCGCCAGC | 4980 |
| TGCGTAGGCG | TATCCCCGGC | AATAATGGCG | TGATGCAGCG | CATAGCGTTT | GCCCTGCGGC | 5040 |
| CAGTCCGGTG | TTTCACCGCC | CGCCTGGTGC | ATCCCCGGCA | GCCACCAGCG | CCCGGCTACT | 5100 |
| TCGGGCTTAC | GCGGATCGGC | CAGATCGATG | GTCAGGAAGA | TGTAGTCGGT | AAAACCGTCG | 5160 |
| ATCAGCGCAG | ACACATACGC | CCAGCGCCCG | CCGACGTACC | AGATGCGGTG | AATACCGATG | 5220 |
| CCGTTAAGCG | ACAGGAAACT | GATTTCCCGC | GCTGCGCGGG | AGTGGAAATA | TCAAAGATGC | 5280 |
| GCAGCCCGGC | GCTCCAGCCC | CTGTCCTGCA | CATCGCTGAC | CGTGTCACCC | ACCGAGCGGG | 5340 |
| TGTAGTACAC | CTTCTCATCA | GCAAAACGGG | CGTCAGCAAA | CAGATCCCGG | GCGTTGATCA | 5400 |
| CCAGCAGCAG | ATCGTCATGC | GCCTGGAGTG | CACGTTCCAG | GTGCCCGGCG | GCGCGGCAAT | 5460 |
| ATAGTTGACG | GTGGTGGGCC | GGGTCGGATC | GCGAACATCG | ACCACGGAAA | AACCCTGCGA | 5520 |
| CACCATATGG | CCGATATAGG | CGAATCCGCG | GTGCACCATC | AGCTGCACGC | CGTCCGGACG | 5580 |

```
ACCGCCCTGA  TCGCTATGGC  CAATCAGCCG  CATATTGCGG  CTGTATTCGG  GGGAAGGTAA     5640

TGCTGACATA  GGGGATCCCT  CTCGCCCGGT  GGCATGGTTT  TCCCCCCTCT  CCTGCGGAGA     5700

GGGCCGGGGC  GAGGGCACCA  GGCCGCCGCC  CACCGCCACC  CGGCTTGATT  TTATTTGTTC     5760

TTCGCTTCCA  GCGTCGCGAA  CCACGGCGCG  ATAAAGTCTT  CGGTCTGGCC  CCAGCCAGGG     5820

ATAATTTTCC  CCAGCGACGC  CACGTTTACC  GCTCCCGGCT  GGGCCGCCAG  CAGCGCCTGG     5880

GGAATCGCTG  CCGCCTTGAA  GTCGTAGGTG  GCTGGCGTCG  GCTCGCCGGC  GATCTTGTTG     5940

GCGATCAGCC  GCACGTTGGT  CGCGCCGATA  AGCTT                                  5975
```

( 2 ) INFORMATION FOR SEQ ID NO:24:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "primer"

( x i ) SEQUENCE DESCRIPTION: SEQ ID NO:24:

```
CGACGTTGTA  AAACGACGGC  CAGT                                               24
```

( 2 ) INFORMATION FOR SEQ ID NO:25:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "primer"

( x i ) SEQUENCE DESCRIPTION: SEQ ID NO:25:

```
CAGGAAACAG  CTATGAC                                                        17
```